United States Patent
Gaweco et al.

(10) Patent No.: US 9,447,069 B2
(45) Date of Patent: Sep. 20, 2016

(54) ROR MODULATORS AND THEIR USES

(71) Applicants: Anderson Gaweco, New York, NY (US); Jefferson W. Tilley, North Caldwell, NJ (US); John Walker, St. Charles, MO (US); Samantha Palmer, Brooklyn, NY (US); James Blinn, Brooklyn, NY (US)

(72) Inventors: Anderson Gaweco, New York, NY (US); Jefferson W. Tilley, North Caldwell, NJ (US); John Walker, St. Charles, MO (US); Samantha Palmer, Brooklyn, NY (US); James Blinn, Brooklyn, NY (US)

(73) Assignee: INNOV17 LLC, Brooklyn, NY (US)

( * ) Notice: Subject to any disclaimer, the term of this patent is extended or adjusted under 35 U.S.C. 154(b) by 0 days.

(21) Appl. No.: 14/394,787

(22) PCT Filed: Apr. 30, 2013

(86) PCT No.: PCT/US2013/038867
§ 371 (c)(1),
(2) Date: Oct. 16, 2014

(87) PCT Pub. No.: WO2013/166015
PCT Pub. Date: Nov. 7, 2013

(65) Prior Publication Data
US 2015/0099779 A1    Apr. 9, 2015

Related U.S. Application Data

(60) Provisional application No. 61/736,895, filed on Dec. 13, 2012, provisional application No. 61/779,856, filed on Mar. 13, 2013, provisional application No. 61/640,401, filed on Apr. 30, 2012.

(51) Int. Cl.
| | | |
|---|---|---|
| *C07D 401/04* | (2006.01) | |
| *C07D 403/04* | (2006.01) | |
| *C07D 413/04* | (2006.01) | |
| *C07D 401/14* | (2006.01) | |
| *C07D 403/14* | (2006.01) | |

(52) U.S. Cl.
CPC ........... *C07D 401/04* (2013.01); *C07D 401/14* (2013.01); *C07D 403/04* (2013.01); *C07D 403/14* (2013.01); *C07D 413/04* (2013.01)

(58) Field of Classification Search
None
See application file for complete search history.

(56) References Cited

U.S. PATENT DOCUMENTS

| | | | |
|---|---|---|---|
| 7,879,893 B2 * | 2/2011 | Olsen et al. | 514/381 |
| 2003/0229120 A1 * | 12/2003 | Olsen | A61K 31/4192 514/314 |
| 2006/0122181 A1 * | 6/2006 | Ikemoto | A61K 31/381 514/235.2 |

* cited by examiner

*Primary Examiner* — Timothy R Rozof

(57) ABSTRACT

The invention relates to ROR modulators; compositions comprising an effective amount of a ROR modulator; and methods for treating or preventing diseases associated with ROR.

16 Claims, No Drawings ns), and for
ROR MODULATORS AND THEIR USES

PRIORITY

This application is a National Stage Application of PCT/US2013/038863 filed Apr. 30, 2013, which claims the priority benefit of U.S. provisional application Nos. 61/640,401, filed Apr. 30, 2012, 61/736,895, filed Dec. 13, 2012, and 61/779,856, filed Mar. 13, 2013. The entire disclosures of these applications are relied on for all purposes and are hereby incorporated by reference in their entirety.

FIELD OF THE INVENTION

The invention relates to Retinoic Acid Receptor-Related Orphan Receptor (ROR) regulated diseases and disorders. More particularly, the invention relates to ROR modulators; compositions comprising an effective amount of a ROR modulator; and methods for treating or preventing ROR regulated diseases and disorders.

BACKGROUND OF THE INVENTION

There are high unmet medical needs in the few established therapies for several autoimmune, inflammatory and metabolic diseases. Despite the diverse clinical manifestations of these diseases, Retinoic Acid Receptor-Related Orphan Receptors (RORs) regulate and contribute to the pathogenesis of these diseases through modulation of immune responses and lipid/glucose homeostasis. Only recently has the critical regulatory role of RORs been well-characterized and target validated in several animal models of some of these diseases. RORs are transcription factors which belong to the nuclear hormone receptor superfamily (Jetten (2009) *Nucl. Recept. Signal.*, 7:e003; Jetten et al. (2013) *Front Endocrinol. (Lausanne)*, 4:1; Jetten & Joo (2006) *Adv. Dev. Biol.*, 16:313-355). The ROR subfamily consists of three major isoforms: RORα (NR1F1), RORβ (NR1F2), and RORγ (NR1F3), encoded by the RORA, RORB and RORC genes, respectively. RORs are multidomain proteins that contain four principal domains typical of nuclear receptors: a highly variable N-terminal A/B domain, a highly conserved DNA-binding domain (DBD), a ligand binding domain (LBD) that contains the ligand-dependent activation function-2 (AF-2), and a hinge domain between the DBD and LBD. Each ROR gene through alternative splicing and promoter usage generates several ROR isoforms that differ only in their amino-terminus. In humans, there are four RORα isoforms (RORα1-4), one RORβ1 isoform, and two RORγ isoforms (RORγ1 and RORγ2 [RORγt]) that are expressed in a highly tissue-specific manner. RORα and RORγ play an important role in the regulation of lipid/glucose homeostasis, cellular metabolism, immune function and circadian rhythms, and have been implicated in the pathogenesis of several autoimmune, inflammatory and metabolic diseases (Burris et al. (2012) *Chem. Biol.*, 19:51-59; Burris et al. (2013) *Pharmacol. Rev.*, 65:710-778; Huh & Littman (2012) *Eur. J. Immunol.*, 42:2232-2237; Jetten (2009) *Nucl. Recept. Signal.*, 7:e003; Jetten et al. (2013) *Front Endocrinol. (Lausanne)*, 4:1). Synthetic ligands have been described that interact with the RORα and RORγ LBD functioning as a switch that induces a ROR LBD conformational change. Such change promotes the recruitment and displacement of regulatory coactivator and corepressor proteins and upon ROR DBD binding to the ROR responsive element of the target genes lead to the induction or inhibition of ROR-regulated gene transcriptional activity. Therefore, small molecule drugs that bind to the nuclear receptor LBDs such as ROR could elicit a variety of pharmacological responses, including activation (agonists), inactivation (antagonists or non-agonists), and for receptors that are constitutively active, ligands can downregulate the constitutive response (inverse agonists).

RORγt is the master regulator of human T Helper 17 ($T_H17$) cell differentiation, function and cytokine production (Ivanov et al. (2006) *Cell*, 126:1121-1133). The critical role of $T_H17$ cells in the pathogenesis of autoimmune and inflammatory diseases has been established and is conferred by the production of its signature proinflammatory cytokines IL-17A, IL-17F, IL-17AF, IL-21, IL-22 (Ghoreschi et al. (2010) *Nature*, 467:967-971; Lee et al. (2012) *Nat. Immunol.*, 13:991-999; Miossec et al. (2009) *N. Engl. J. Med.*, 361:888-898; Miossec & Kolls (2012) *Nat. Rev. Drug Discov.*, 11:763-776; Zepp et al. (2011) *Trends Immunol.*, 32:232-239). Although several transcription factors regulate $T_H17$, γ/δ T and innate lymphoid cells as important sources of $T_H17$ cytokines, these cells are distinguished by its specific regulation of RORγt for cytokine transcriptional output and effector functions and to a lesser extent by RORα in humans (Cua & Tato (2010) *Nat. Rev. Immunol.*, 10:479-489; Huh & Littman (2012) *Eur. J. Immunol.*, 42:2232-2237; Ivanov et al. (2006) *Cell*, 126:1121-1133; Spits & Di Santo (2011) *Nat. Immunol.*, 12:21-27; Sutton et al. (2012) *Eur. J. Immunol.*, 42:2221-2231). Also, in several autoimmune disease models, there is a relative imbalance of increased $T_H17$ cells over low numbers of immunosuppressive CD4$^+$CD25$^+$ Foxp3$^+$ regulatory T cells [$T_{Reg}$] (Edwards et al. (2011) *J. Neurol.*, 258:1518-1527; Littman & Rudensky (2010) *Cell*, 140:845-858). Targeting RORγt could have a broader antiinflammatory effect on the combined inhibition of all $T_H17$ cytokine production and inflammatory cellular function, and in the induction and expansion of suppressive $T_{Reg}$ cells, important in autoimmune and inflammatory disease resolution, and may also have therapeutic potential in metabolic diseases such as diet-induced insulin resistance known to be regulated by RORγ. Since both RORγ1 and RORγt [RORγ1] protein isoforms, contain identical LBDs, small molecule RORγ modulators that inhibit RORγt activity will also inhibit RORγ. RORα similarly plays an important regulatory role in the pathogenesis of autoimmune and inflammatory disorders, and also in metabolic diseases. RORα critically regulates lipid and glucose homeostasis and cellular metabolism that contribute to the development of metabolic diseases. The therapeutic benefits of inhibiting RORα for metabolic diseases is associated with diminished inflammation and downregulated expression of RORα target genes as seen in RORα-deficient mice. As ligand-dependent transcription factors, it is desirable to prepare compounds that modulate RORα and/or RORγ activity which can be used in the treatment of RORα- and/or RORγ-regulated autoimmune, inflammatory and metabolic diseases.

SUMMARY OF THE INVENTION

The invention is based in part on the discovery of ROR modulators which interact with RORα and/or RORγ and thereby inhibit or induce RORα and/or RORγ-activity, and RORα- and/or RORγ-regulated target gene and protein expression. The invention is also based on compositions comprising an effective amount of a ROR modulator; and methods for treating or preventing disorders regulated by RORα and/or RORγ, comprising the administration of an effective amount of a ROR modulator.

In one aspect, compounds of the Formula I are described:

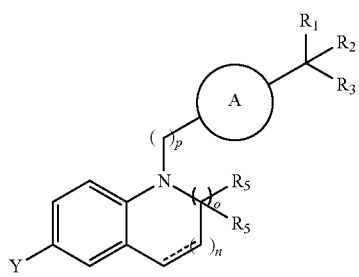

wherein

A is aryl or heteroaryl optionally substituted with C1-C4 alkyl, halogen, OH, CN, or $N(R_4)_2$;

$R_1$ is absent, H, OH, halogen, $N(R_4)_2$, or C1-C4 alkyl optionally substituted with halogen, OH, O-alkyl, CN, or $N(R_4)_2$;

$R_2$ and $R_3$ are independently selected from H, halogen, or C1-C4 alkyl optionally substituted with halogen, OH, CN, $N(R_4)_2$, or $R_2$ and $R_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or $N(R_4)_2$, or $R_2$ and $R_3$, can be taken together to form a carbonyl;

Each $R_4$ is independently H, alkyl, or aryl, or two $R_4$ can be taken together to form a 4-7 membered ring, optionally incorporating 0-3 N, O, S atoms; wherein the 4-7 membered ring is optionally substituted with C1-C4 alkyl, halogen, OH, CN, halogen, or $N(R_4)_2$;

$R_5$ is independently H or alkyl, or both $R_5$ can be taken together to form a carbonyl;

Y is 5-7 membered heteroaromatic ring linked via a carbon atom and optionally substituted;

n is 0, or 1;

o is 0 or 1;

p is 1 or 2; and wherein the symbol ═══ indicates a single or double bond;

or a pharmaceutically acceptable salt, hydrate, solvate, prodrug, and tautomer thereof.

In another aspect, compounds of the Formula Ia are described:

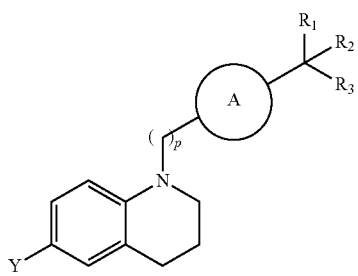

wherein

A is aryl or heteroaryl optionally substituted with C1-C4 alkyl, halogen, OH, CN, or $N(R_4)_2$;

$R_1$ is absent, H, OH, halogen, $N(R_4)_2$, or C1-C4 alkyl optionally substituted with halogen, OH, O-alkyl, CN, or $N(R_4)_2$;

$R_2$ and $R_3$ are independently selected from H, halogen, or C1-C4 alkyl optionally substituted with halogen, OH, CN, $N(R_4)_2$, or $R_2$ and $R_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or $N(R_4)_2$, or $R_2$ and $R_3$, can be taken together to form a carbonyl;

Each $R_4$ is independently H, alkyl, or aryl, or two $R_4$ can be taken together to form a 4-7 membered ring, optionally incorporating 0-3 N, O, S atoms; wherein the 4-7 membered ring is optionally substituted with C1-C4 alkyl, halogen, OH, CN, halogen, or $N(R_4)_2$;

Y is 5-7 membered heteroaryl linked via a carbon atom and optionally substituted; and p is 1 or 2;

or a pharmaceutically acceptable salt, hydrate, solvate, prodrug, and tautomer thereof.

In another aspect, compounds of the Formula Ib are described:

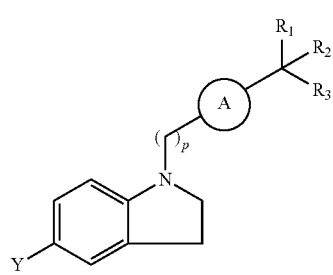

wherein

A is aryl or heteroaryl optionally substituted with C1-C4 alkyl, halogen, OH, CN, and $N(R_4)_2$;

$R_1$ is absent, H, OH, halogen, $N(R_4)_2$, or C1-C4 alkyl optionally substituted with halogen, OH, O-alkyl, CN, or $N(R_4)_2$;

$R_2$ and $R_3$ are independently selected from H, halogen, or C1-C4 alkyl optionally substituted with halogen, OH, CN, $N(R_4)_2$, or $R_2$ and $R_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or $N(R_4)_2$, or $R_2$ and $R_3$, can be taken together to form a carbonyl;

Each $R_4$ is independently H, alkyl, or aryl, or two $R_4$ can be taken together to form a 4-7 membered ring, optionally incorporating an 0-3 atoms; wherein the 4-7 membered ring is optionally substituted with C1-C4 alkyl, halogen, OH, CN, halogen, or $N(R_4)_2$;

Y is 5-7 membered heteroaryl linked via a carbon atom and optionally substituted; and p is 1 or 2;

or a pharmaceutically acceptable salt, hydrate, solvate, prodrug, and tautomer thereof.

In another aspect, compounds of the Formula Ic are described:

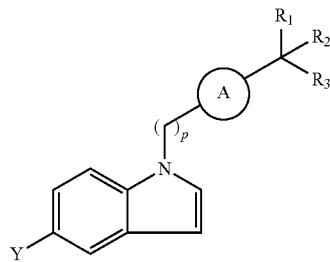

wherein
A is aryl or heteroaryl optionally substituted with C1-C4 alkyl, halogen, OH, CN, or $N(R_4)_2$;
$R_1$ is absent, H, OH, halogen, $N(R_4)_2$, or C1-C4 alkyl optionally substituted with halogen, OH, O-alkyl, CN, or $N(R_4)_2$;
$R_2$ and $R_3$ are independently selected from H, halogen, or C1-C4 alkyl optionally substituted with halogen, OH, CN, $N(R_4)_2$, or $R_2$ and $R_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or $N(R_4)_2$, or $R_2$ and $R_3$, can be taken together to form a carbonyl;
Each $R_4$ is independently H, alkyl, or aryl, or two $R_4$ can be taken together to form a 4-7 membered ring, optionally incorporating 0-3 N, O, S atoms; wherein the 4-7 membered ring is optionally substituted with C1-C4 alkyl, halogen, OH, CN, halogen, or $N(R_4)_2$;
Y is 5-7 membered heteroaryl linked via a carbon atom and optionally substituted; and
p is 1 or 2;
or a pharmaceutically acceptable salt, hydrate, solvate, prodrug, and tautomer thereof.

In another aspect, compounds of the Formula Id are described:

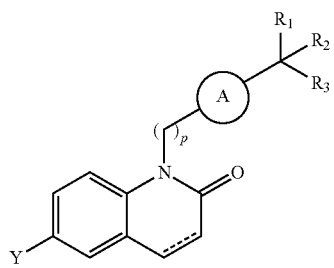

wherein
A is aryl or heteroaryl optionally substituted with C1-C4 alkyl, halogen, OH, CN, or $N(R_4)_2$;
$R_1$ is absent, H, OH, halogen, $N(R_4)_2$, or C1-C4 alkyl optionally substituted with halogen, OH, O-alkyl, CN, or $N(R_4)_2$;
$R_2$ and $R_3$ are independently selected from H, halogen or C1-C4 alkyl optionally substituted with halogen, OH, CN, $N(R_4)_2$, or $R_2$ and $R_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or $N(R_4)_2$, or $R_2$ and $R_3$, can be taken together to form a carbonyl;
Each $R_4$ is independently H, alkyl, or aryl, or two $R_4$ can be taken together to form a 4-7 membered ring, optionally incorporating an additional N, O, S atom; wherein the 4-7 membered ring is optionally substituted with C1-C4 alkyl, halogen, OH, CN, halogen, or $N(R_4)_2$;
Y is 5-7 membered heteroaryl linked via a carbon atom and optionally substituted;
p is 1 or 2; and
wherein the symbol ═══ indicates a single or double bond;
or a pharmaceutically acceptable salt, hydrate, solvate, prodrug, and tautomer thereof.

DETAILED DESCRIPTION OF THE INVENTION

The invention is based in part on the discovery of ROR modulators, which interact with RORα and/or RORγ and thereby inhibit or induce RORα and/or RORγ activity, and RORα- and/or RORγ-regulated target gene and protein expression. The invention is also based on compositions comprising an effective amount of a ROR modulator; and methods for treating or preventing disorders regulated by RORα and/or RORγ, comprising the administration of an effective amount of a ROR modulator.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The following definitions are used in connection with the ROR modulators:
"ROR" refers to RORα and/or RORγ isoforms
"RORα" refers to all isoforms encoded by the RORA gene
"RORγ" refers to all isoforms encoded by the RORC gene which include RORγ1 and RORγt [RORγ2].
"RORα modulator" refers to a chemical compound that modulates, either directly or indirectly, the activity of RORα. RORα modulators include antagonists/non-agonists, inverse agonists and agonists of RORα.
"RORγ modulator" refers to a chemical compound that modulates, either directly or indirectly, the activity of RORγ. RORγ modulators include antagonists/non-agonists, inverse agonists and agonists of RORγ.

The term "ROR modulator" includes any and all possible isomers, stereoisomers, enantiomers, diastereomers, tautomers, pharmaceutically acceptable salts, hydrates, solvates, and prodrugs of the ROR modulators described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

"$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl.

"$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl.

"$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl.

"$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The terms "monocyclic or bicyclic aryl," or an "monocyclic or bicyclic heteroaryl" as used herein include but are not limited to, indolyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benzotriazolyl, imidazopyridinyl, dihydropurinonyl, pyrrolopyrimidinyl, purinyl, pyrazolopyridinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, quinolonyl, isoquinolonyl, phthalazinyl, benzodioxyl, indolinyl, dihydroquinolinyl, tetrahydroquinolinyl, dihydroisoquinolyl, tetrahydroisoquinolinyl, benzoazepinyl, benzodiazepinyl, benzoxapinyl, benzoxazepinyl, phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, and triazinyl.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl. It is understood that any of the substitutable hydrogens on a cycloalkyl can be substituted with halogen, $C_1$-$C_3$ alkyl, hydroxyl, alkoxy and cyano groups.

The term "heterocycle" as used herein refers to a cyclic hydrocarbon containing 3-6 atoms wherein at least one of the atoms is an O, N, or S wherein a monocyclic heterocycle may contain up to two double bonds. Examples of heterocycles include, but are not limited to, aziridine, oxirane, thiirane, azetidine, oxetane, thietane, pyrrolidine, tetrahydrofuran, tetrahydrothiophene, piperidine, tetrahydropyran, thiane, imidazolidine, oxazolidine, thiazolidine, dioxolane, dithiolane, piperazine, oxazine, dithiane, and dioxane.

A "subject" is a mammal, e.g., a human, mouse, rat, guinea pig, dog, cat, horse, cow, pig, or non-human primate, such as a monkey, chimpanzee, baboon or rhesus monkey, and the terms "subject" and "patient" are used interchangeably herein.

The invention also includes pharmaceutical compositions comprising an effective amount of a ROR modulator and a pharmaceutically acceptable carrier. The invention includes a ROR modulator provided as a pharmaceutically acceptable prodrug, hydrate, salt, such as a pharmaceutically acceptable salt, enantiomers, stereoisomers, or mixtures thereof Representative "pharmaceutically acceptable salts" include, e.g., water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

An "effective amount" when used in connection with a ROR modulator is an amount effective for treating or preventing a ROR-regulated disease or disorder.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body.

The term "treating", with regard to a subject, refers to improving at least one symptom of the subject's disorder. Treating can be curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a compound or pharmaceutically acceptable salt of the compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a ROR modulator.

The term "optionally substituted," as used in this disclosure, means a suitable substituent can replace a hydrogen bound to a carbon, nitrogen, or oxygen. When a substituent is oxo (i.e., =O) then 2 hydrogens on the atom are replaced by a single O. Suitable substituents are selected from the following which include, but are not limited to, hydroxyl, halogen, perfluorinated $C_1$-$C_6$ alkyl, amine, —$C_1$-$C_{12}$ alkyl, —$C_2$-$C_{12}$ alkene, —$C_2$-$C_{12}$ alkyne, —($C_1$-$C_3$ alkyl)-(cycloalkyl), aryl, alkyl-aryl, —C(O)H, —C(O)OH, —C(O)alkyl, —C(O)—O-alkyl, —C(O)NH(alkyl), benzyl, —C(O)NH$_2$, —C(O)N(alkyl)$_2$, —NHC(O)H, —NHC(O)alkyl, —SO$_2$(alkyl), —SO$_2$NH$_2$, —SO$_2$NH(alkyl), —SO$_2$N(alkyl)$_2$, S, CN, and SCN. It will be understood by those skilled in the art, with respect to any group containing one or more substituents, that such groups are not intended to introduce any substitution or substitution patterns that are sterically impractical, synthetically non-feasible and/or inherently unstable. Furthermore, combinations of substituents and/or variables within any of the Formulae represented herein are permissible only if such combinations result in stable compounds or useful synthetic intermediates wherein stable implies a reasonable pharmologically relevant half-life at physiological conditions.

The following abbreviations are used herein and have the indicated definitions: ACTB is β-actin, AF-2 is activation function-2, AIBN is azobisisobutyronitrile, Boc and BOC are tert-butoxycarbonyl, Boc$_2$O is di-tert-butyl dicarbonate, BSA is bovine serum albumin, CD is cluster of differentiation, CDI is 1,1'-carbonyldiimidazole, DBD is DNA-binding domain, DCC is N,N'-dicyclohexylcarbodiimide, DIEA and DIPEA is N,N-diisopropylethylamine, DMAP is 4-dimethylaminopyridine, DMEM is Dulbecco's Modified Eagle Medium, DMF is N,N-dimethylformamide, DMSO is dimethyl sulfoxide, DOSS is sodium dioctyl sulfosuccinate, EC$_{50}$ is half maximal effective concentration, EDC and EDCI are 1-ethyl-3-(3-dimethylaminopropyl)carbodiimide hydrochloride, ELISA is enzyme-linked immunosorbent assay, EtOAc is ethyl acetate, FBS is fetal bovine serum, FOXP3 is forkhead box P3, G-CSF is granulocyte colony-stimulating factor, h is hour, HATU is 2-(7-aza-1H-benzotriazole-1-yl)-1,1,3,3-tetramethyluronium hexafluorophosphate, HIV is human immunodeficiency virus, HOBt is 1-Hydroxybenzotriazole, HPMC is hydroxypropyl methylcellulose, HPRT1 is hypoxanthine phosphoribosyltransferase 1, IC$_{50}$ is half maximal inhibitory concentration, IFN-γ is interferon gamma, IL is interleukin, IL-23R is interleukin 23 receptor, LAH is lithium aluminum hydride, LBD is ligand binding domain, MIQE is minimum information for publication of quantitative real-time PCR experiments, MTBE is methyl tert-butyl ether, NBS is N-bromosuccinnide, NMP is N-methyl-2-pyrrolidone, oxone is potassium peroxymonosulfate, PBMCs is peripheral blood mononuclear cells, PCR is polymerase chain reaction, Pd/C is palladium on carbon, PGK1 is phosphoglycerate kinase, PPIA is peptidylprolyl isomerase A, REST is Relative Expression Software Tool, RORα is retinoic acid receptor-related orphan receptor alpha, RORγ is retinoic acid receptor-related orphan receptor gamma, TBAB is tetrabutylammonium bromide, TBP is terminal binding protein, TFA is trifluoroacetic acid, TFRC is transferrin receptor, TGF-β1 is transforming growth factor beta 1, T$_H$17 is T helper 17 cell, TGPS is tocopherol propylene glycol succinate, THF is tetrohydrofuran, TLC is thin layer chromatography, TR-FRET is time-resolved fluorescence resonance energy transfer and μM is micromolar.

Compounds

In one aspect, compounds of the Formula I are described:

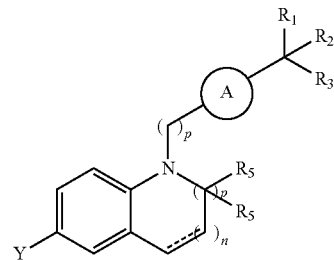

I wherein
A is aryl or heteroaryl optionally substituted with C1-C4 alkyl, halogen, OH, CN, or N(R$_4$)$_2$;
R$_1$ is absent, H, OH, halogen, N(R$_4$)$_2$, or C1-C4 alkyl optionally substituted with halogen, OH, O-alkyl, CN, or N(R$_4$)$_2$;
R$_2$ and R$_3$ are independently selected from H, halogen, or C1-C4 alkyl optionally substituted with halogen, OH, CN, N(R$_4$)$_2$, or R$_2$ and R$_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or N(R$_4$)$_2$, or R$_2$ and R$_3$, can be taken together to form a carbonyl;
Each R$_4$ is independently H, alkyl, or aryl, or two R$_4$ can be taken together to form a 4-7 membered ring, optionally incorporating 0-3 N, O, S atoms; wherein the 4-7 membered ring is optionally substituted with C1-C4 alkyl, halogen, OH, CN, halogen, or N(R$_4$)$_2$;
R$_5$ is independently H, or alkyl, or both R$_5$ can be taken together to form a carbonyl;
Y is 5-7 membered heteroaromatic ring linked via a carbon atom and optionally substituted;
n is 0, or 1;
o is 0 or 1;
p is 1 or 2; and
wherein the symbol ≡≡≡ indicates a single or double bond.
or a pharmaceutically acceptable salt, hydrate, solvate, prodrug, and tautomer thereof.

In some embodiments, Y is selected from thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, and triazinyl. In some embodiments, Y can be optionally substituted.

In another aspect, compounds of the Formula Ia are described:

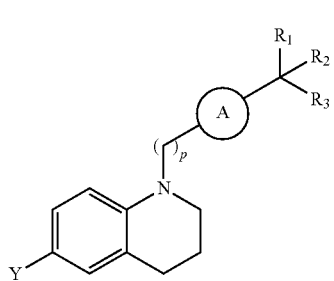

Ia wherein
A is aryl or heteroaryl optionally substituted with C1-C4 alkyl, halogen, OH, CN, or N(R$_4$)$_2$;
R$_1$ is absent, H, OH, halogen, N(R$_4$)$_2$, or C1-C4 alkyl optionally substituted with halogen, OH, O-alkyl, CN, or N(R$_4$)$_2$;
R$_2$ and R$_3$ are independently selected from H, halogen, or C1-C4 alkyl optionally substituted with halogen, OH, CN, N(R$_4$)$_2$, or R$_2$ and R$_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or N(R$_4$)$_2$, or R$_2$ and R$_3$, can be taken together to form a carbonyl;
Each R$_4$ is independently H, alkyl, or aryl, or two R$_4$ can be taken together to form a 4-7 membered ring, optionally incorporating 0-3 N, O, S atoms; wherein the 4-7 membered ring is optionally substituted with C1-C4 alkyl, halogen, OH, CN, halogen, or N(R$_4$)$_2$;
Y is 5-7 membered heteroaryl linked via a carbon atom and optionally substituted; and
p is 1 or 2;
or a pharmaceutically acceptable salt, hydrate, solvate, prodrug, and tautomer thereof.

In another aspect, compounds of the Formula Ib are described:

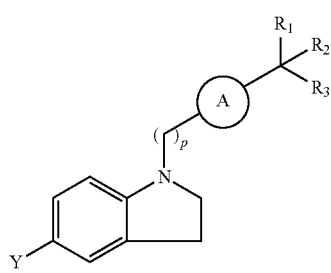

Ib wherein
A is aryl or heteroaryl optionally substituted with C1-C4 alkyl, halogen, OH, CN, or N(R$_4$)$_2$;
R$_1$ is absent, H, OH, halogen, N(R$_4$)$_2$, or C1-C4 alkyl optionally substituted with halogen, OH, O-alkyl, CN, or N(R$_4$)$_2$;
R$_2$ and R$_3$ are independently selected from H, halogen, or C1-C4 alkyl optionally substituted with halogen, OH, CN, N(R$_4$)$_2$, or R$_2$ and R$_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or N(R$_4$)$_2$, or R$_2$ and R$_3$, can be taken together to form a carbonyl;
Each R$_4$ is independently H, alkyl, or aryl, or two R$_4$ can be taken together to form a 4-7 membered ring, optionally incorporating an 0-3 atoms; wherein the 4-7 membered ring is optionally substituted with C1-C4 alkyl, halogen, OH, CN, halogen, or N(R$_4$)$_2$;
Y is 5-7 membered heteroaryl linked via a carbon atom and optionally substituted; and
p is 1 or 2;
or a pharmaceutically acceptable salt, hydrate, solvate, prodrug, and tautomer thereof.

In another aspect, compounds of the Formula Ic are described:

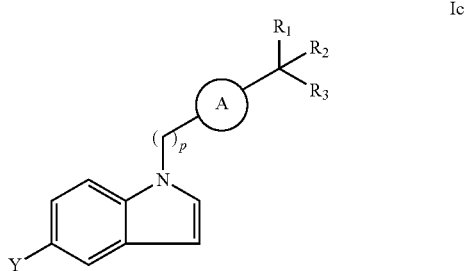

Ic wherein
A is aryl or heteroaryl optionally substituted with C1-C4 alkyl, halogen, OH, CN, and N(R$_4$)$_2$;
R$_1$ is absent, H, OH, halogen, N(R$_4$)$_2$, or C1-C4 alkyl optionally substituted with halogen, OH, O-alkyl, CN, or N(R$_4$)$_2$;
R$_2$ and R$_3$ are independently selected from H, halogen, or C1-C4 alkyl optionally substituted with halogen, OH, CN, N(R$_4$)$_2$, or R$_2$ and R$_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or N(R$_4$)$_2$, or R$_2$ and R$_3$, can be taken together to form a carbonyl;
Each R$_4$ is independently H, alkyl, or aryl, or two R$_4$ can be taken together to form a 4-7 membered ring, optionally incorporating 0-3 N, O, S atoms; wherein the 4-7 membered ring is optionally substituted with C1-C4 alkyl, halogen, OH, CN, halogen, or N(R$_4$)$_2$;
Y is 5-7 membered heteroaryl linked via a carbon atom and optionally substituted; and
p is 1 or 2;
or a pharmaceutically acceptable salt, hydrate, solvate, prodrug, and tautomer thereof.

In another aspect, compounds of the Formula Id are described:

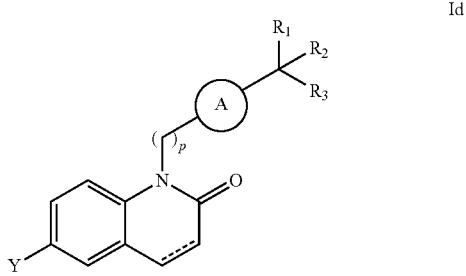

Id wherein
A is aryl or heteroaryl optionally substituted with C1-C4 alkyl, halogen, OH, CN, and N(R$_4$)$_2$;
R$_1$ is absent, H, OH, halogen, N(R$_4$)$_2$, or C1-C4 alkyl optionally substituted with halogen, OH, O-alkyl, CN, or N(R$_4$)$_2$;
R$_2$ and R$_3$ are independently selected from H, halogen, or C1-C4 alkyl optionally substituted with halogen, OH, CN, N(R$_4$)$_2$, or R$_2$ and R$_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or $N(R_4)_2$, or $R_2$ and $R_3$, can be taken together to form a carbonyl;

Each $R_4$ is independently H, alkyl, or aryl, or two $R_4$ can be taken together to form a 4-7 membered ring, optionally incorporating an additional N, O, S atom; wherein the 4-7 membered ring is optionally substituted with C1-C4 alkyl, halogen, OH, CN, halogen, or $N(R_4)_2$;

Y is 5-7 membered heteroaryl linked via a carbon atom and optionally substituted;

p is 1 or 2; and wherein the symbol ═ indicates a single or double bond;

or a pharmaceutically acceptable salt, hydrate, solvate, prodrug, and tautomer thereof.

In one embodiment, suitable compounds of the invention include:

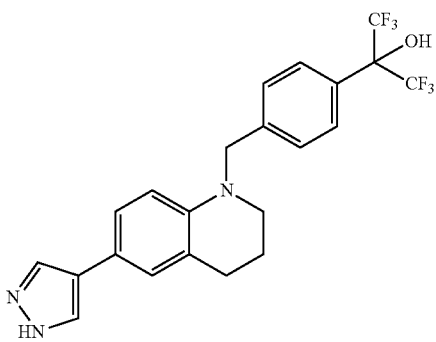

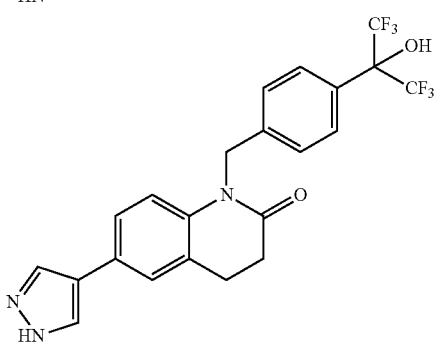

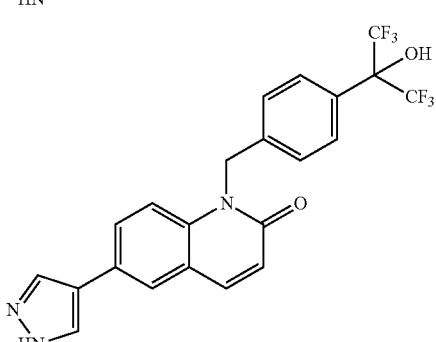

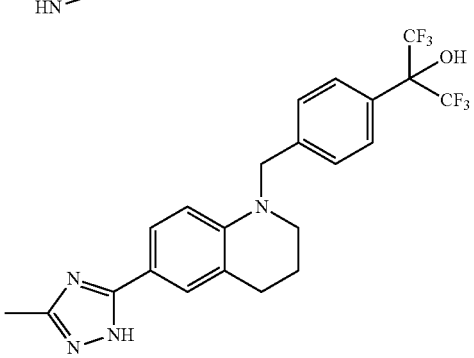

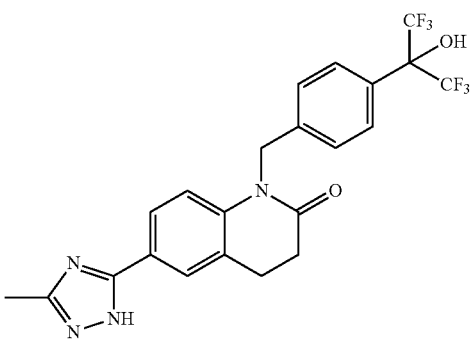

15
-continued
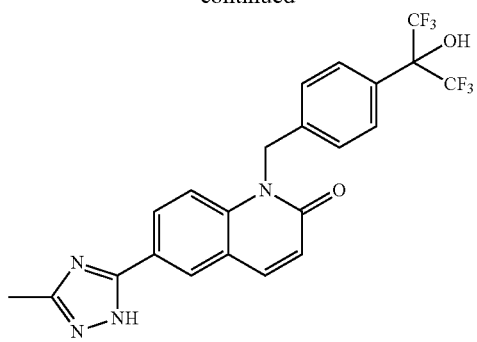
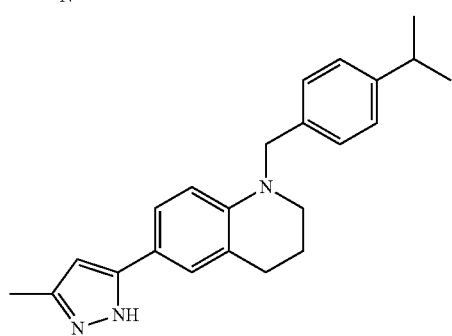
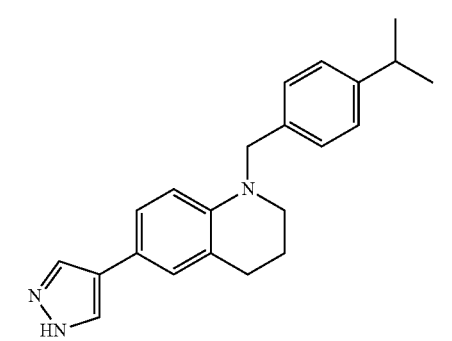
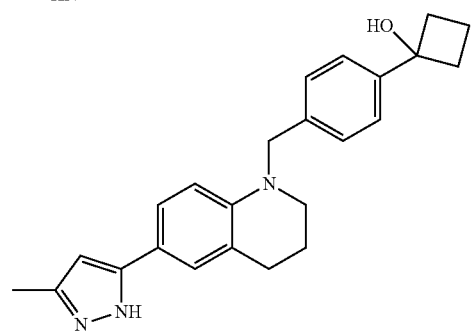
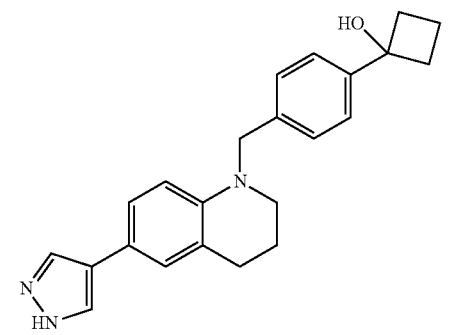
16
-continued
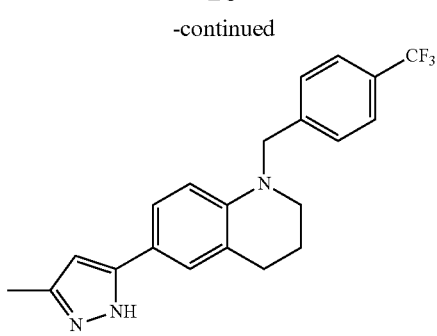
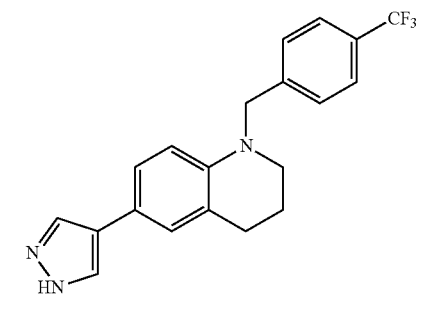
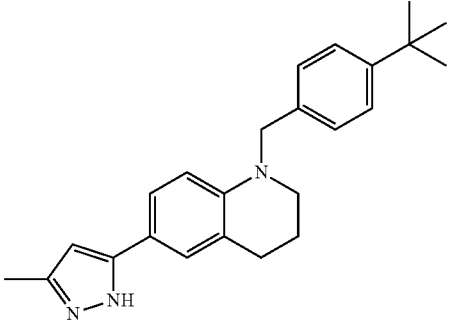
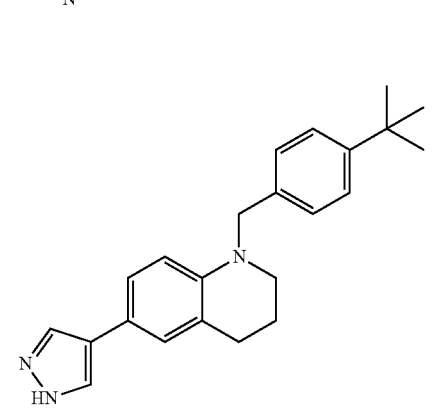
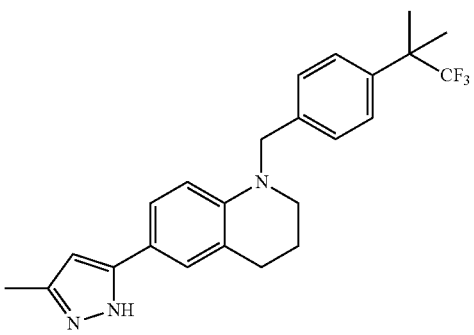

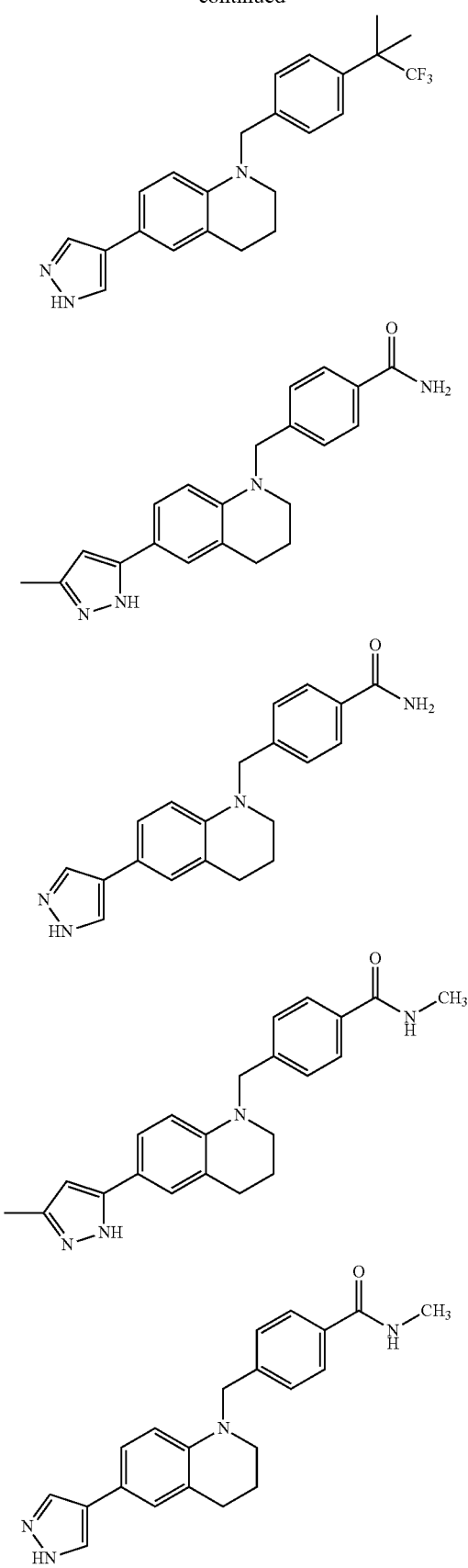
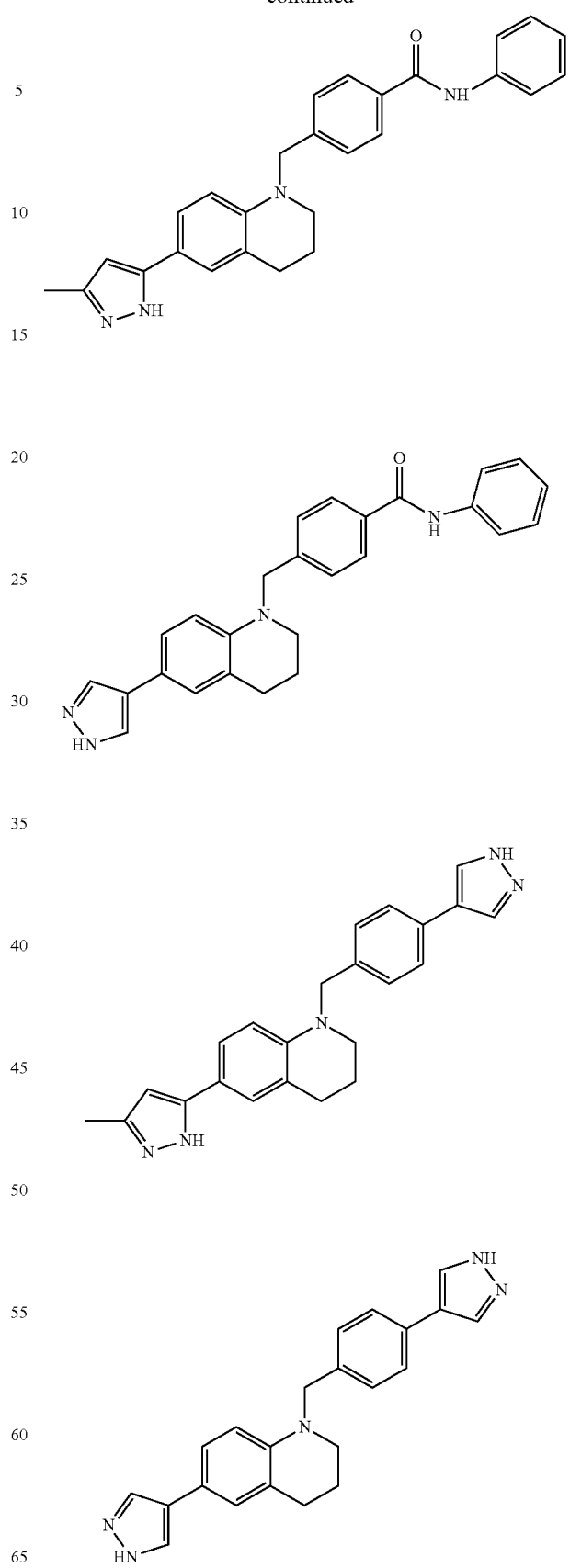

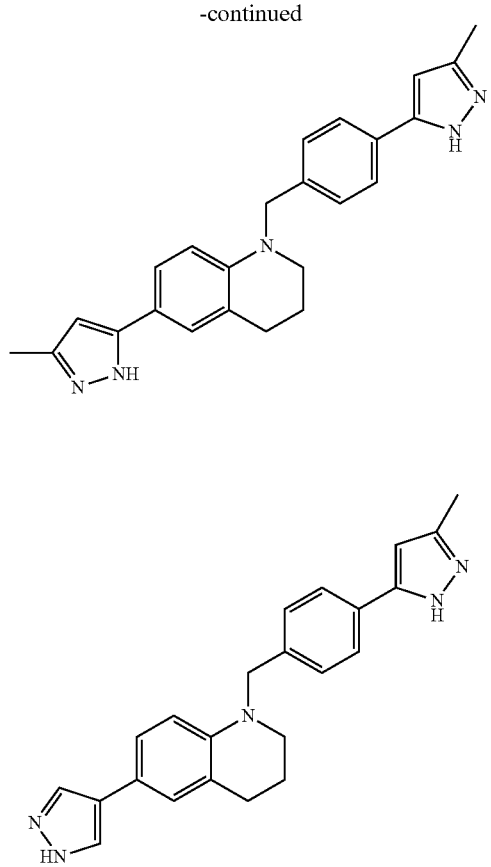
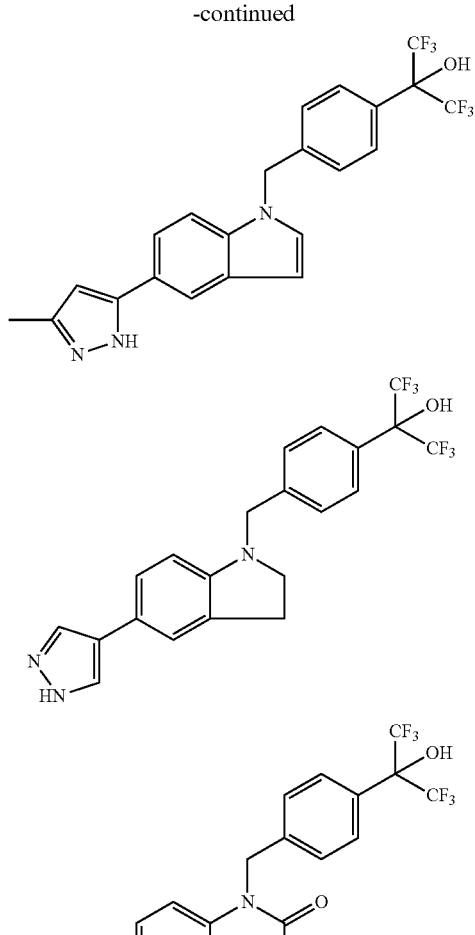
In another embodiment, suitable compounds of the invention also include:
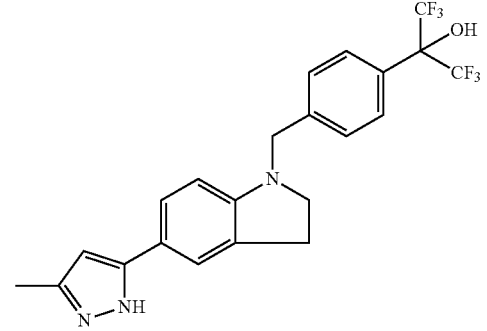
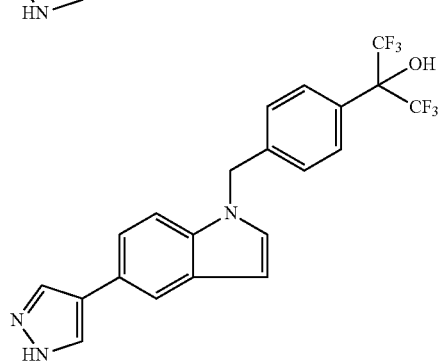
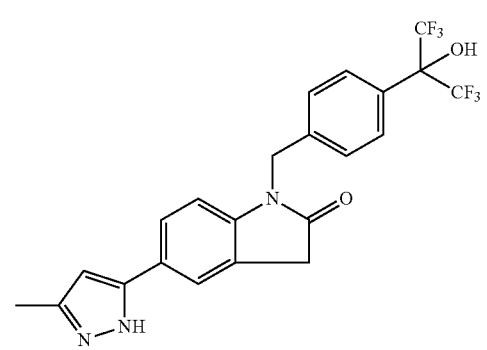
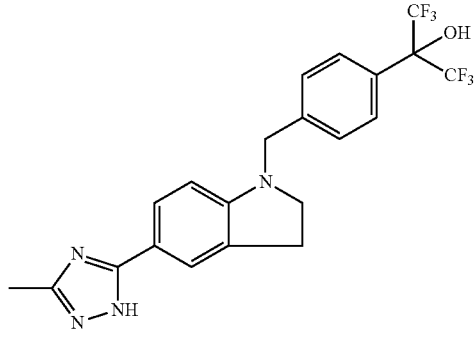

-continued
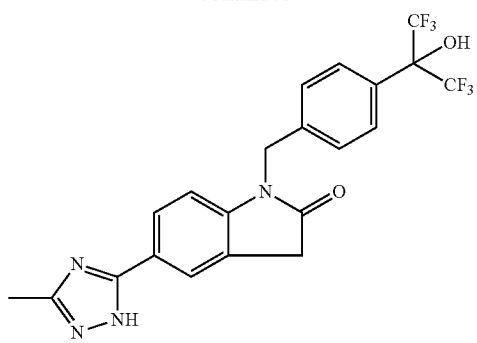
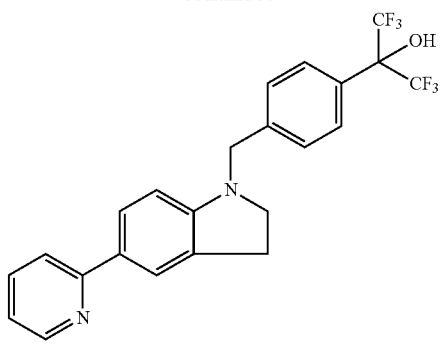
In yet another embodiment, suitable compounds of the invention may also include:
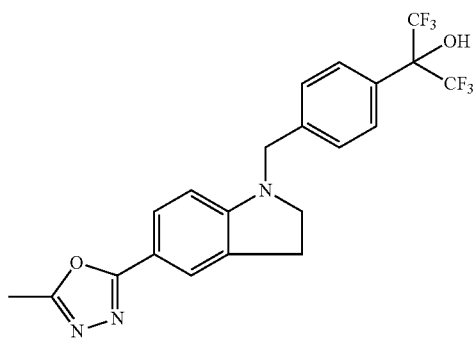
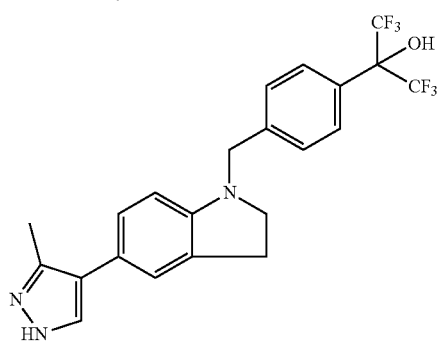
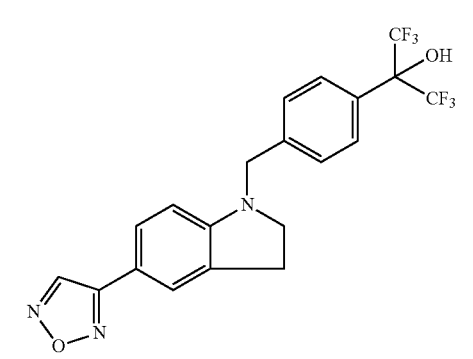
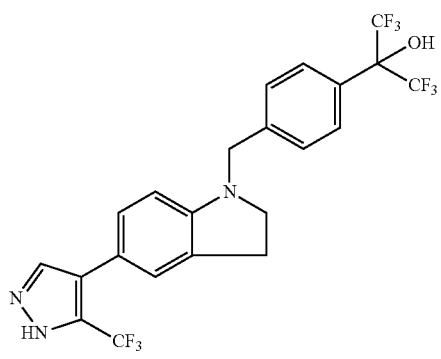

-continued
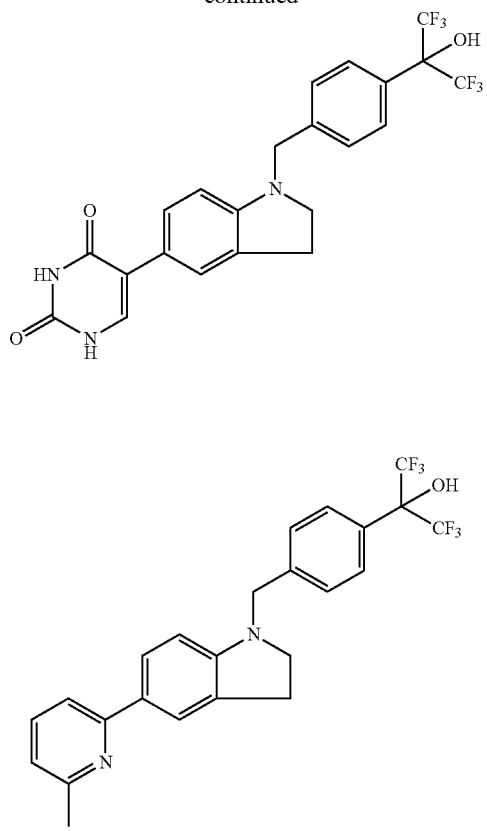
In other embodiments, the invention also include:
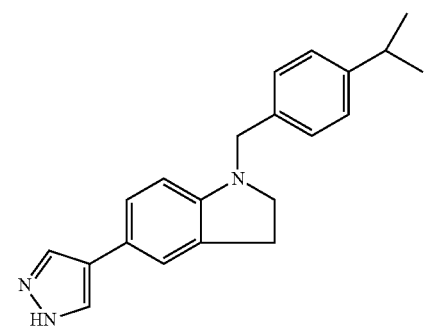
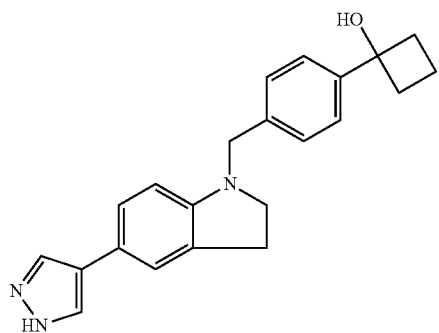
-continued
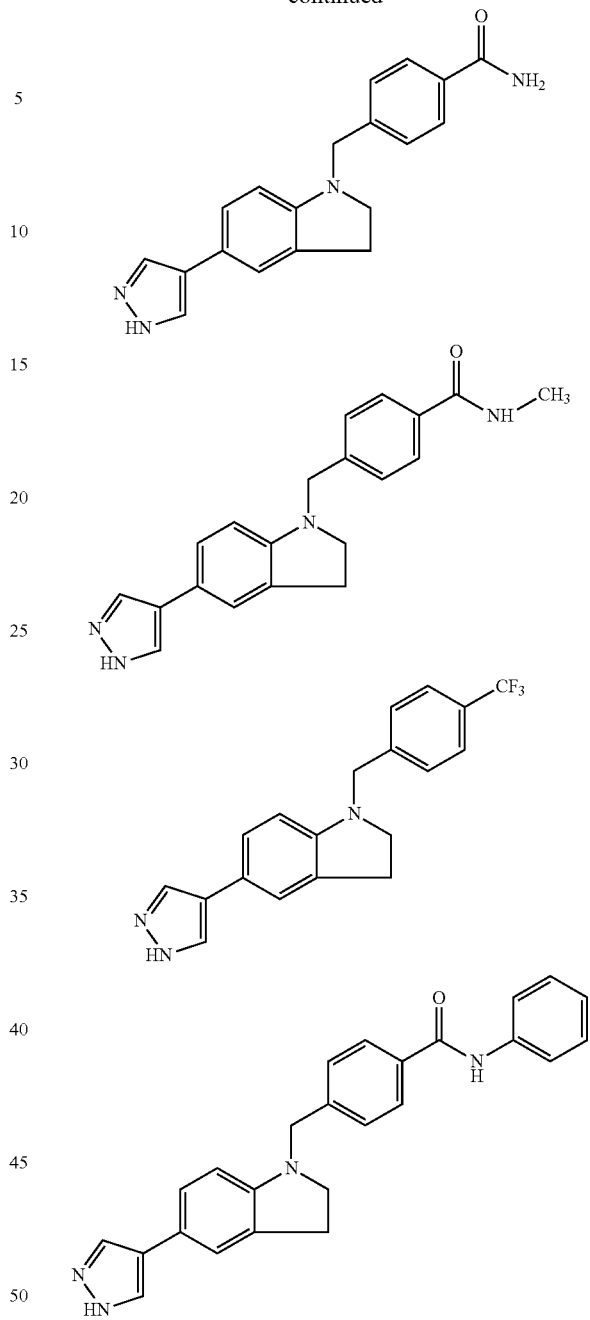

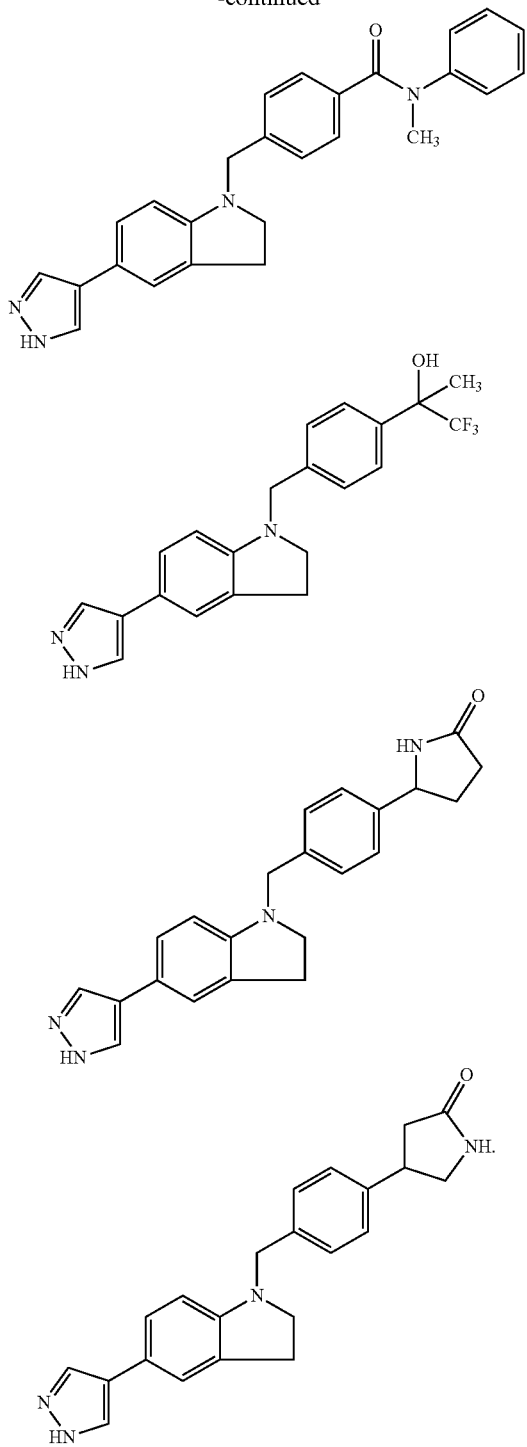

In another aspect, methods of inhibiting, preventing or treating a disease, or symptoms of a disease, regulated by RORα and/or RORγ, is provided, which comprises administering to a subject in need thereof, a therapeutically-effective amount of a ROR modulator. In some embodiments, the disease regulated by RORα and/or RORγ is selected from Autoimmune, Inflammatory and Metabolic Diseases, including but not limited to angina pectoris, myocardial infarction, atherosclerosis, cystic fibrosis, gastritis, autoimmune myositis, giant cell arteritis, Wegener's granulomatosis, asthma, chronic obstructive pulmonary disease, rheumatoid arthritis, juvenile rheumatoid arthritis, allergen-induced lung inflammation, allergy, psoriasis, psoriatic arthritis, colitis, inflammatory bowel disease, Crohn's disease, ulcerative colitis, Sjogren's syndrome, dry eye, optic neuritis, neuromyelitis optica, myasthenia gravis, Guillain-Barre syndrome, Graves disease, multiple sclerosis, autoimmune uveitis, ankylosing spondylitis, organ transplant rejection, polymyalgia rheumatic, systemic lupus erythematosus, cutaneous lupus, lupus nephritis, glomerulonephritis, diabetes mellitus type 1, pulmonary inflammation, macular degeneration, obesity, non-alcoholic fatty liver disease, steatohepatitis, insulin resistance, diabetes mellitus type 2, glucose intolerance, and metabolic syndrome; and Other Diseases, including but not limited to multiple myeloma, bone disease associated with multiple myeloma, gastric cancer and colon cancer.

Also described are methods of modulating RORα and/or RORγ activity as an agonist, inverse agonist or antagonist/non-agonist in a subject which comprises administering to a subject in need thereof a pharmaceutically effective amount of a ROR modulator.

Also described are methods of inducing or inhibiting RORα- and/or RORγ-regulated target gene expression and protein production in a subject which comprises administering to a subject in need thereof a pharmaceutically effective amount of a ROR modulator.

Also described are methods of regulating corepressor and/or coactivator protein interaction with RORα and/or RORγ LBD in a subject which comprises administering to a subject in need thereof a pharmaceutically effective amount of a ROR modulator.

Also described are methods of reducing the amount of RORα- and/or RORγ-regulated production of $T_H17$ cytokines IL-17A, IL-17F, IL-17AF, IL-21, and/or IL-22 in a subject which comprises administering to a subject in need thereof a pharmaceutically effective amount of a ROR modulator.

Also described are methods of inducing or inhibiting, either directly or indirectly, RORα- and/or RORγ-regulated cell proliferation or activation in a subject which comprises administering to a subject in need thereof a pharmaceutically effective amount of a ROR modulator.

The ROR modulators can each be administered in amounts that are sufficient to treat or prevent but are not limited to Autoimmune, Inflammatory and Metabolic Diseases, or prevent the development thereof in subjects.

The invention also includes pharmaceutical compositions useful for treating or preventing a ROR regulated disease, or for inhibiting a ROR regulated disease, or more than one of these activities. The compositions can be suitable for internal use and comprise an effective amount of a ROR modulator and a pharmaceutically acceptable carrier. The ROR modulators are especially useful in that they demonstrate very low systemic toxicity or no systemic toxicity.

Administration of the ROR modulators can be accomplished via any mode of administration for therapeutic agents. These modes include systemic or local administration such as oral, nasal, parenteral (intravenous), intramuscular, intrathecal, intra-vitreal, transdermal, subcutaneous, vaginal, buccal, rectal, topical administration modes or as a drug-eluting stent.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, intrathecal, intra-vitreal injection, subcutaneous or intramuscular form, all using forms well known to those skilled in the pharmaceutical arts.

Illustrative pharmaceutical compositions are tablets and gelatin capsules comprising a ROR modulator and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as *acacia*, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the ROR modulator is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the ROR modulators.

The ROR modulators can be also formulated as a suppository that can be prepared from fatty emulsions or suspensions; using polyalkylene glycols such as propylene glycol, as the carrier.

In further embodiments, the pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, delayed release formulations, extended release formulations, pulsatile release formulations, multiparticulate formulations, and mixed immediate and controlled release formulations The ROR modulators can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564, the contents of which are herein incorporated by reference in their entirety.

ROR modulators can also be delivered by the use of monoclonal antibodies as individual carriers to which the ROR modulators are coupled. The ROR modulators can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxide-polylysine substituted with palmitoyl residues. Furthermore, the ROR modulators can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, ROR modulators are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 80%, from about 5% to about 60%, or from about 1% to about 20% of the ROR modulator by weight or volume.

The dosage regimen utilizing the ROR modulator is selected in accordance with a variety of factors including type, species, age, weight, sex, race, diet, and medical condition of the patient; the severity of the condition to be treated; the route of administration; the renal or hepatic function of the patient; and the particular ROR modulator employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 0.1 mg to about 5000 mg of the active ingredient per unit dose which could be administered. In one embodiment, the compositions are in the form of a tablet that can be scored. Appropriate dosages of the ROR modulators can be determined as set forth in Goodman, L. S.; Gilman, A. The Pharmacological Basis of Therapeutics, 5th ed.; MacMillan: New York, 1975, pp. 201-226, the contents of which are hereby incorporated by reference.

ROR modulators can be administered in a single daily dose, or the total daily dosage can be administered in divided doses of two, three or four times daily. Furthermore, ROR modulators can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Other illustrative topical preparations include creams, ointments, lotions, aerosol sprays and gels, wherein the concentration of the ROR modulator ranges from about 0.1% to about 15%, w/w or w/v.

The ROR modulators can also each be administered in amounts that are sufficient to treat or prevent ROR-associated diseases. These diseases include, but are not limited to, Autoimmune, Inflammatory and Metabolic diseases, either individually or in combination with one or more agents and or methods for treating and preventing these ROR-regulated diseases.

Compounds according to the present invention may be administered in combination with the following non-limiting examples of therapeutic agents and methods for treating and preventing these ROR-regulated diseases in any combination that may include, but are not limited to any of the following: glucocorticoids, nonsteroidal antiinflammatory drugs (NSAIDs) (non-limiting examples include acetominophen, aspirin, capsaicin, diclofenac, diclofenac/misoprostol, efenamic acid, etodolac, felbinac, fenoprofen, flurbiprofen, ketoprofen, ibuprofen, indomethacin, ketorolac, loxoprofen, meclofenamate, meloxicam, nabumetone, naproxen, nimesulide, oxaprozin, piroxicam, sulindac, tolmetin), cyclooxygenase (COX)-2 inhibitors (non-limiting examples include celecoxib, valdecoxib, etoricoxib, lumiracoxib, parecoxib), licofelone (ML3000), disease-modifying antirheumatic drugs (DMARDs), methotrexate, chloroquine, hydroxychloroquine, cyclophosphamide (Cytoxan), inosine monophosphate dehydrogenase (IMPDH) inhibitors (a non-limiting example is mycophenolate mofetil [Cellcept, Myfortic]), sirolimus, everolimus (rapamycin), purine nucleoside phosphorylase inhibitors, de novo purine synthesis inhibitors (non-limiting examples include polygentamate derivatives of methotrexate, antifolate compounds), dihydroorotate dehydrogenase inhibitors (malononitrilamides), prostaglandins PGE2 inhibitors, P2X7 receptor inhibitors, proteinase-activated receptor 2 (PAR-2) inhibitors, inhibitors of activated Complement (non-limiting examples include Eculizumab, Pexelizumab), complement C3/C5 convertase inhibitors (a non-limiting example is Nafamostat mesilate), active convertase inhibitors, complement C5aR antagonists, EP4 agonists, prostaglandin-I2 analogs (non-limiting examples include iloprost, cicaprost, treprostinil), Sulphasalazine (SASP), 5-aminosalicylic acid (5-ASA), immunomodulator drugs (non-limiting examples include azathioprine (AZA), 6-mercaptopurine (6-MP), methotrexate (MTX)), calcineurin inhibitors (non-limiting examples include cyclosporine, voclosporine, tacrolimus), interleukin-10 (AG011), placenta-derived cells (PDA001), mucosal addressin cell adhesion molecule (MAdCAM) inhibitors (PF-00547659), GLP-2 agonists (non-limiting examples include ZP1848, ALX-0600), anti-CD3, CCR9 inhibitors, lenalidomide (Revlimid), recombinant human interleukin-11, CXCR2 Antagonists (a non-limiting example is SB-656933), glucagon-like peptide-2 (GLP-2) analogue (Teduglutide), insulin-like growth factor-1 (IGF-1) (Increlex), synthetic guanylhydrazone semapimod (CPSI-2364), intracellular adhesion molecule-1 (ICAM-1) inhibitor (alicaforsen), stem cell therapeutics (a non-limiting example is Prochymal), activated protein C (aPC), vitamin D analogs (a non-limiting example is calcipotriene), retinoids (a non-limiting example is tazarotene), phototherapy (non-limiting examples include broadband ultraviolet B light, narrow band ultraviolet B light, psoralen plus ultraviolet A light), methotrexate, cyclosporine, acitretin, CCR6 inhibitors, CCL20 inhibitors, deoxyspergualin, alkylate deoxyribonucleic acid (DNA) agents, tumor necrosis factor (TNF)-alpha inhibitors (non-limiting examples include etanercept, infliximab, adalimumab, certolizumab pegol (Cimzia), golimumab (CNTO-148), inhibitors of TNF-alpha converting enzyme, Janus kinase (JAK) 1, 2 and/or 3 inhibitors (non-limiting examples include Tofacitinib (Xeljanz), INCB-28050, Ruxolitinib), spleen tyrosine kinase (SYK) inhibitors (a non-limiting example is R-788), caspase inhibitor, chemokine receptor antagonists, protein kinase C (pkc) inhibitors (a non-limiting example is Enzastaurin), p38 mitogen-activated protein kinase (MAPK) inhibitors, caspase inhibitors, NF-κB modulators, B cell inhibitors, Hydroxychloroquine, B-lymphocyte stimulator (BLyS) inhibitors (a non-limiting example is belimumab (Benlysta)), membrane-bound and soluble B-cell activating factor inhibitors (a non-limiting example is LY2127399), inhibitors that antagonize the binding of BLyS and APRIL (a proliferation-inducing ligand) cytokines to B cells in order to prevent B-cell maturation and autoantibody production (a non-limiting example is Atacicept), anti-CD19, CD20 inhibitors (non-limiting examples include Rituximab, Ocrelizumab, Ofatumumab), CD22 inhibitors (a non-limiting example is Epratuzumab), T cell inhibitors (non-limiting examples include Alefacept (Amevive), IPP-201101), interferon inhibitors (non-limiting examples include MEDI-545, rontalizumab, fontalizumab), toll-like receptor inhibitors, prasterone, estrogen receptor antagonist (fulvestrant), cytotoxic T-lymphocyte-associated antigen 4 (CTLA-4)-Ig (a non-limiting example is Abatacept (Orencia)), v-set domain containing T cell activation inhibitor 1 (VTCN1; B7-H4) agonists (AMP-110), interleukin-1 receptor antagonists (AMG 108, Anakinra [Kineret]), interleukin-1 beta antagonists (non-limiting examples include canakinumab, Xoma 052), soluble IL-1 receptors (a non-limiting example is rilonacept), interleukin-2R antagonists (non-limiting examples include basiliximab (Simulect), daclizumab (Zenapax), interleukin-6 receptor antagonists (non-limiting examples include Tocilizumab [Actemra]), calcipotriene/betamethasone (Taclonex), fumarate (Panaclar/BG-12), interleukin-15 inhibitors, interleukin-17 and interleukin-17 receptor inhibitors (non-limiting examples include Secukinumab, Brodalumab, Ixekizumab, RG7624), DHODH inhibitors (a non-limiting example is Vidofludimus), interleukin-18 inhibitors, T helper (Th) 17 cell inhibitors, interleukin 12/interleukin 23 inhibitors (non-limiting examples include Ustekinumab [CNTO-1275], briakinumab [ABT-874]), interleukin-22 inhibitors, interleukin-23 inhibitors (a non-limiting example is ustekinumab), interleukin-12 inhibitors (a non-limiting example is ustekinumab), alpha interferons, beta interferons [Interferon beta-1a (Avonex, Rebif), Interferon beta-1b (Betaseron/Betaferon), Glatiramer acetate (Copaxone), selective adhesion molecule inhibitors, integrin antagonists (Natalizumab [Tysabri], vedolizumab), sphingosine 1-phosphate receptor (S1P-R) agonists (a non-limiting example is Fingolimod [Gilenya]), fumarate derivative immunomodulators (a non-limiting example is BG-12 [Tecfidera]), laquinimod, anti-LFA-1 (a non-limiting example is Efalizumab [Raptiva]), MBP-8298, cladribin (a non-limiting example is Mylinax), Novantrone, isoxanol dihydroorotate dehydrogenase (DHODH) and tyrosine kinase inhibitor (a non-limiting example is teriflunomide [HMR-1726]), Revimmune (cyclophosphamide), Fampridine SR (4-aminopyridine), Panaclar (dimethylfumarate), MBP8298 (dirucotide, synthetic peptide version of a portion of human myelin basic protein), Campath (alemtuzumab), anti-CD52, Cladribine, purine analogs, Fingolimod (sphingosine 1-phosphate receptor agonists), Laquinimod, Teriflunomide, de novo pyrimidine synthesis inhibitors (non-limiting examples include brequinar, leflunomide [Arava]), active metabolites of leflunomide, photodynamic therapy [PDT] with verteporfin, Anti-angiogenic factors non-limiting examples include vascular endothelial growth factor A (VEGFA) inhibitors (non-limiting examples include pegaptanib sodium, ranibizumab, bevacizumab), CCR3 inhibitors, anti-CD48, beta 2-agonists, leukotriene modifiers, phosphodiesterase (PDE) inhibitors (non-limiting examples include tetomilast, ibudilast), selective phosphodiesterase-4 (PDE-4) inhibitors (non-limiting examples include rolipram, roflumilast, piclamilast, pentoxifylline), inhibitors targeting IgE (Omalizumab), Th2 cytokine inhibitors (non-limiting examples include suplatast tosilate, sIL-4R, IL-5 inhibitors), Macrolides, Ketolide, adenosine A2B antagonists, kappa B kinase 2 inhibitors, prostanoid and F2-isoprostane antagonists, Nitric oxide donors, inducible nitric oxide synthase inhibitors, toll-like receptor modulators, Lorcaserin, phentermine, topiramate, bupropion, naltrexone, Anti-CD3, Antithymocyte globulin, serine protease inhibitors (a non-limiting example is alpha-1 antitrypsin AAT), tyrosine kinase inhibitors, platelet-derived growth factor receptor (PDGFR) inhibitors, insulin, Antigen-Specific Tolerance inducting agents to Type 1 Diabetes (non-limiting examples include Glutamate Decarboxylase 65 and Heat Shock Protein treatments), cannabinoid receptor 1 (CB1) antagonists, long-acting glucagon-like peptide 1 (GLP1) analogues, dipeptidyl peptidase 4 (DPP4) inhibitors, vasoactive intestinal peptide-pituitary adenylate cyclase-activating polypeptide receptor 2 (VPAC2) agonists, Glucokinase activators, Glucagon receptor antagonists, Cytosolic phosphoenolpyruvate carboxykinase (PEPCK) inhibitors, sodium-glucose co-transporter 2 (SGLT2) inhibitors, salsalate, IκB kinase-β (IKKβ)-inhibitors, nuclear factor kappa B inhibitors, interleukin-1 (IL-1) receptor antagonists, IL-1 beta-specific antibody, sirtuin 1 (SIRT1) activators, selective peroxisome proliferator-activated receptor (PPAR) modulators (SPPARMs), 11β-hydroxysteroid dehydrogenase type 1 (11βHSD1) inhibitors, PPARγ ligands (non-limiting examples include rosiglitazone, pioglitazone, troglitazone), thiazolidinediones, glitazones, Warfarin, coumadin, pradaxa (non-limiting examples include dabigatran etexilate mesylate), anti-thrombotics, Statins, hydroxy-methylglutaryl-coenzyme A reductase (HMG-CoA reductase) inhibitors, ezetimibe, fenofibrates, niacin, amlodipine, Vascular cell-adhesion molecule (VCAM) antagonists, Thromboxane A2 antagonists, prostaglandin D2 receptor 1 antagonists, G-protein-coupled receptor (GPCR) modulators, cannabinoid receptor 1 (also known as CNR1) CB1 receptor antagonists (Rimonabant), cholesteryl ester transfer protein (CETP) inhibitors (JTT-705), chemokine (C-C motif) receptor 2 (CCR2) antagonists, Phospholipase A2 inhibitors, peroxisome proliferator-activated receptor (PPAR) agonists, leucovorin [folinic acid], 5-FU, oxaliplatin, irinotecan, capecitabine, oxaliplatin, bevacizumab, cetuximab, Panitumumab, doxorubicin, mitomycin C (FAM) and combinations thereof, among others.

Methods of Making

Methods for Making the RORα; RORγ and RORα/RORγ Modulators

Examples of synthetic pathways useful for making ROR modulators of the present invention are set forth in the Examples below and generalized herein.

The starting materials I to III shown in scheme 1 wherein Q is a group capable of participating in a transition metal catalyzed cross coupling reaction, such as a chloride, bromide, iodide or triflate, are commercially available or readily prepared from commercially available compounds. In some cases, it may be desirable to convert Q to a boronic acid derivative prior to the coupling reaction with Het-W.

Alkylation can be accomplished by standard methods, such as treatment of the quinoline derivatives with NaH or $K_2CO_3$ followed by a benzyl halide such as a substituted benzyl bromide. In some cases, it may be desirable to incorporate a protecting group on the functionality on the benzyl group. This can be chosen such that it can be later removed, once the key steps, coupling and or alkylation are complete. The use and selection of protecting groups is well documented in the organic synthesis literature. A particularly useful guide in this process is *Greene's Protective Groups in Organic Synthesis* by Peter G. M. Wuts and T. W. Greene, 4th ed., Wiley, 2007.

The resulting benzylamines may then be coupled to the heteroaromatic derivatives Het-W in which Het is a 5-7-membered heteroaromatic compound, which may incorporate a protecting group as appropriate, and W is a functional group capable of participating in a transition metal catalyzed cross-coupling reaction such as a Suzuki reaction. Skilled organic chemists will understand how to select the particular choice of X and Y for a given desired transformation and incorporate the appropriate protection/deprotection methods, where needed. See for example: N. Kudo et al., *Angew. Chem. Int. Ed.,* 2006, 45, 1282-1284 and Dvorak, C. A.; et al., *Journal of Organic Chemistry* 2005, 70, 4188-4190; Barder, T. E., et al. *J. Am. Chem. Soc.* 2005, 127, 4685-4696.

Carrying out the coupling reaction will then lead to the target compounds VII to IX, after protecting group removal, if necessary.

Scheme 1

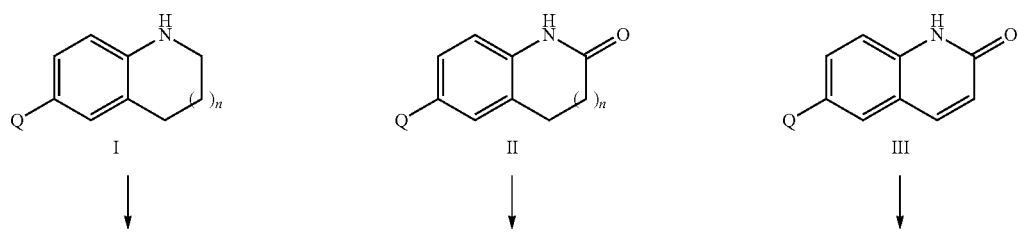

I  II  III

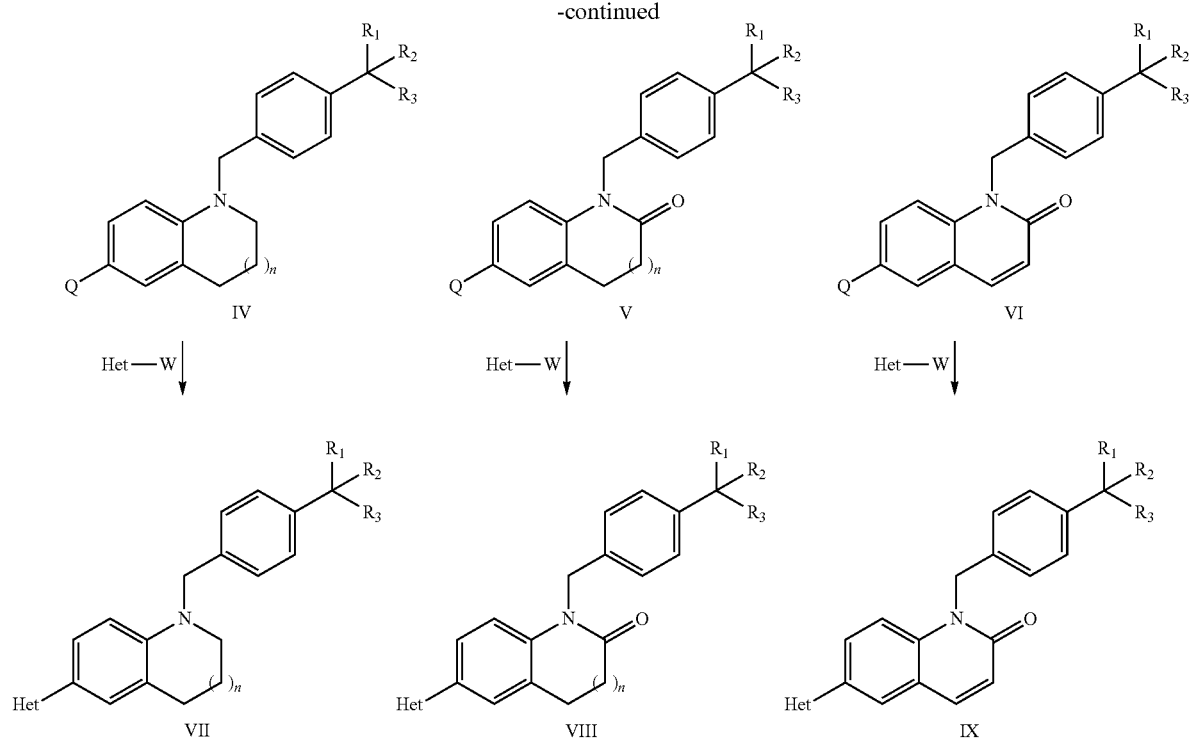

A process for the preparation of heteroaryl derivatives for which the starting materials not are commercially available or readily synthesized may also be prepared starting with the 4-substituted anilines X and XI, wherein Q'=a heteroaromatic derivative as illustrated in Scheme 2.

Where Q' is stable to acidic conditions, the aniline may be acylated with an acryloyl derivative followed by cyclization in the presence of a strong acid, such as $H_2SO_4$ to give compounds of formula XIII or XIV. These compounds can be converted to compound XII by a series of reductions and the products can be alkylated to give XV-XVII as described above. If protecting groups are employed, they can be inserted and removed at appropriate points.

Alternatively, an alkyl alcohol can be added ortho to the aniline nitrogen atom using techniques well known in organic synthesis, for example using an organometallic coupling reaction with an alkenyl or alkynyl alcohol, followed by reduction, if necessary. These alkyl alcohols can then undergo oxidatetive cyclization in the presence of Rh complexes to give compounds of formula XIII which can then be further elaborated to compounds of the invention using standard techniques. See for example Fuita, K.-i., et al., *Organic Lett.* 2004 6, 2785.

Scheme 2

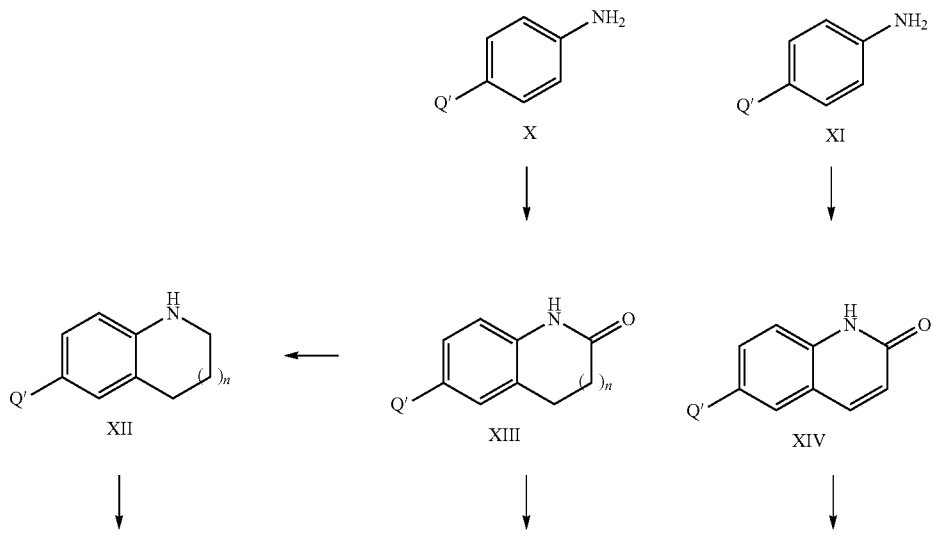

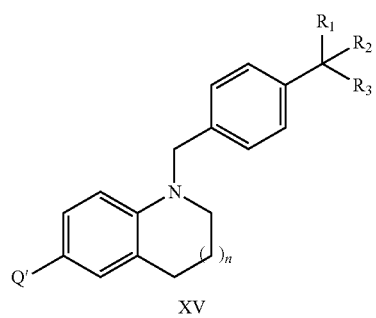
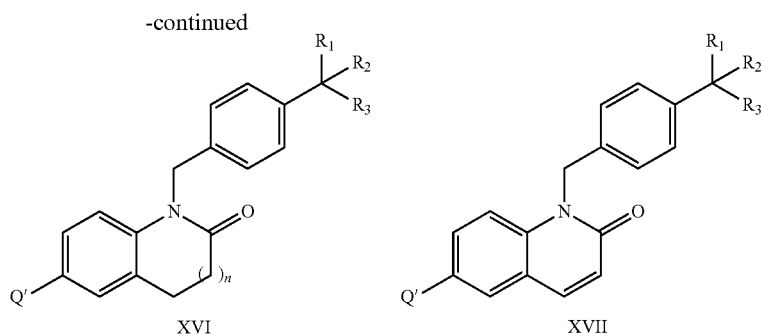

Procedures suitable for indole and indoline derivatives are shown in Scheme 3. An indole derivative of formula XVIII in which Q'=a heteroaromatic species, suitably protected, is alkylated with a benzyl halide in the presence of a base, for example NaH or $K_2CO_3$, to provide a N-benzyl indole of formula XXI, which can be deprotected as appropriate.

Alternatively, an indole derivative of formula XIX, in which Q" is a leaving group suitable for use in a Suzuki reaction or other organo metallic coupling reaction may be alkylated with a substituted benzyl halide, incorporating protecting group as necessary, in the presence of a suitable base, for example NaH to give a N-benzyl derivative XXII. Suzuki or other suitable coupling with a heterocyclic partner as described above then can give the heterocyclic substituted indole derivative, which can be deprotected, if necessary.

Alternatively, an indole of formula XIX may be reduced by treatment with a suitable reducing agent, for example, in the case where Q" is a halogen atom, sodium cyanoborohydride in the presence of acetic acid, to give an indoline derivative XX. In some cases, it may be appropriate to convert the Q" group to a different leaving group, for example from a halide to a borate ester. Such transformations are well presented in the chemistry literature. A coupling reaction with a suitably functionalized heteroaromatic species can then furnish the target compound of the invention XXIV, after deprotection, if necessary. In some cases, it may be feasible to start indoline syntheses with an indoline derivative already incorporating a heteroaromatic ring, such as XXV. In this case an alkylation as described above for XVIII with a benzyl halide can furnish a compound of formula XXIV directly or after deprotection, as appropriate.

Scheme 3

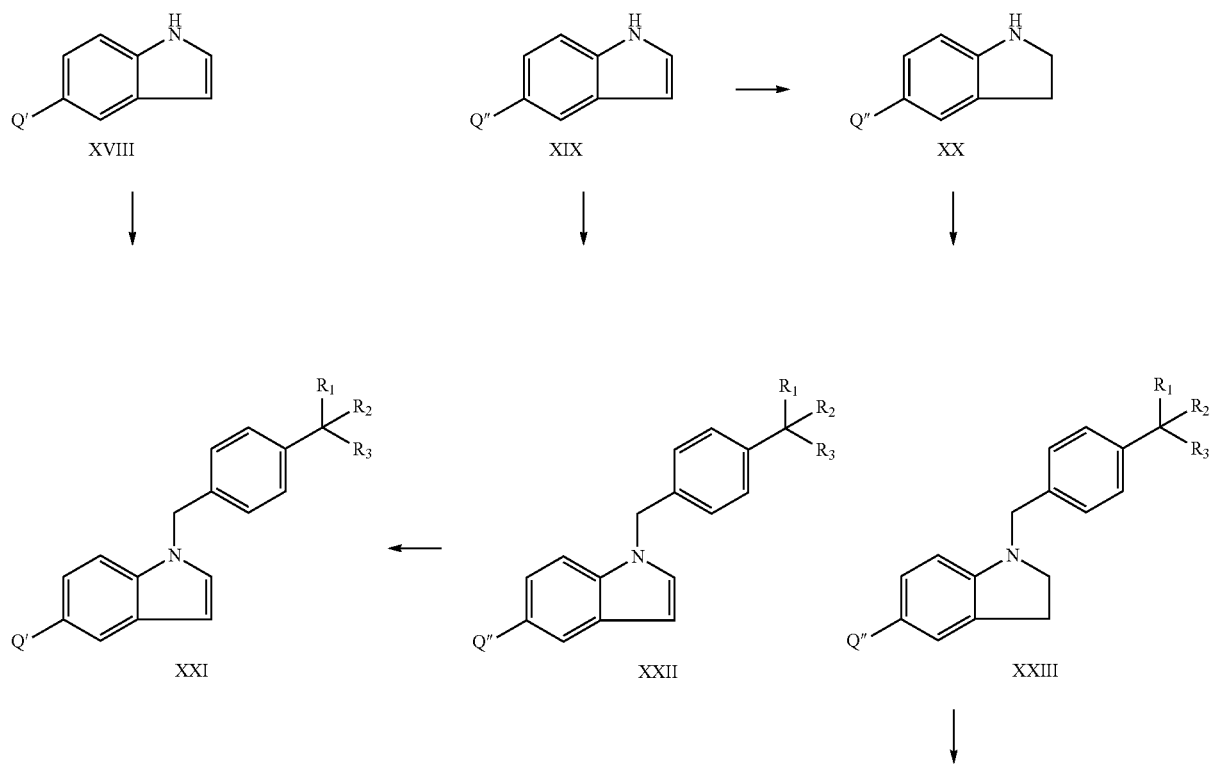

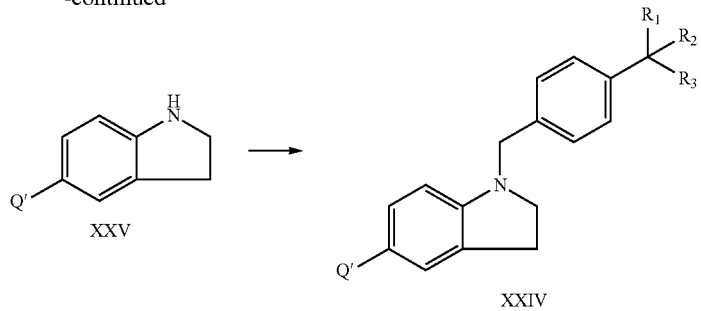

Alternative sequences are also envisioned, in which Q" is a nitrile or converted to a nitrile. Subsequent reactions lead to 1,2,4-triazoles, oxadiazoles and tetrazoles can be carried followed well established literature precedent. Q" can also be or be converted to an alkyne following established chemistry which in turn can be reacted with a substituted azide to give 1,2,3-triazole derivatives.

In some cases, it may be desirable to construct the heteroaromatic species from a carbonyl derivative such as XXVI, XXVII or XXVIII, Y=H, OH, $NHR_4$, or $OR_5$, wherein $R_4$ is H, lower alkyl or $OR_6$, wherein $R_6$ is H or lower alkyl and $R_5$ is lower alkyl or another substituent suitable for the displacement chemistry associated with the intended heterocycle construction. Such intermediates can be alkylated as above with the appropriate benzyl derivatives to give the benyzlated derivatives XXIX, XXX and XXXI, followed by elaboration of the carbonyl derivative to the desired heterocyclic derivative, XXXII, XXXIII, and XXXIV using the chemistry appropriate to the target heterocycle. In general, the sequence of steps necessary to carry out these transformations is well established in the chemistry literature. The sequence of the steps may be altered to suit the particular selection of target, available starting materials and experimental convenience.

In many cases, it may be more desirable to start with a functionalized bycilic core such as IV, V, VI, XIX or XX that can be converted to a carbonyl containing compound such as XXIX, XXX, or XXXI using standard organometallic catalyzed acylation reactions.

Scheme 4

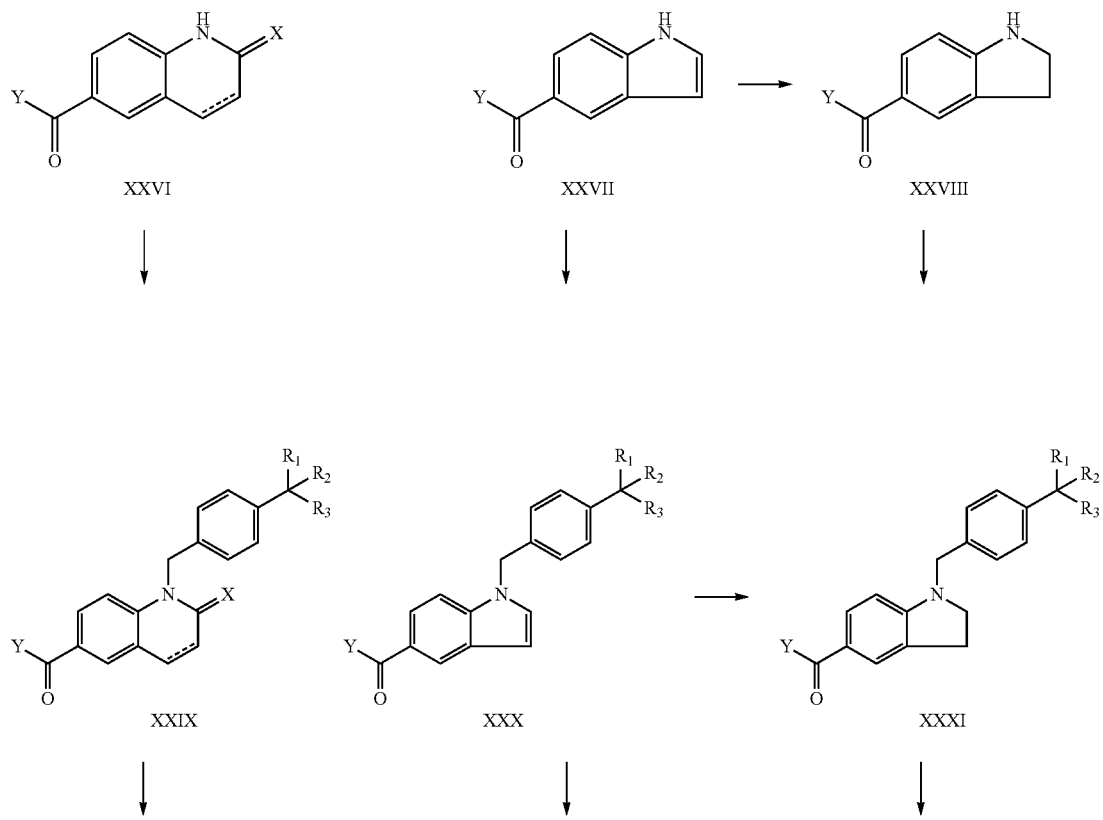

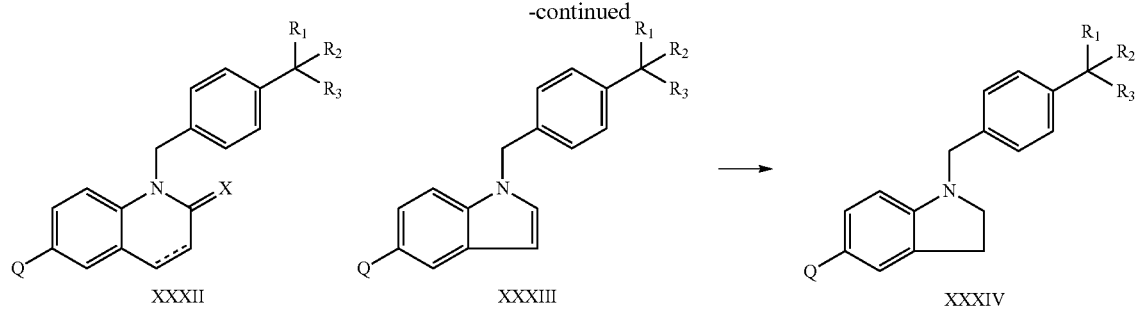

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compounds

The following non-limiting compound examples serve to illustrate further embodiments of the ROR modulators. It is to be understood that any embodiments listed in the Examples section are embodiments of the ROR modulators and, as such, are suitable for use in the methods and compositions described above.

The present invention is not to be limited in scope by the specific embodiments disclosed in the examples, which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

Preparation of 2-(4-(bromomethyl)phenyl)-1,1,1,3,3,3-hexafluoropropan-2-ol

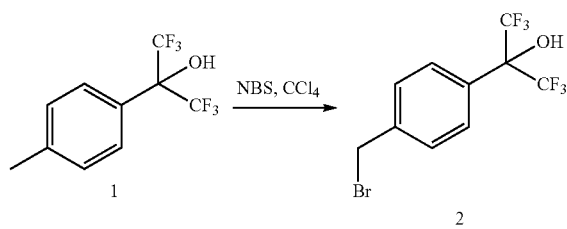 [SMILES: Cc1ccc(C(O)(C(F)(F)F)C(F)(F)F)cc1 ; OC(c1ccc(CBr)cc1)(C(F)(F)F)C(F)(F)F]

To a stirred solution of 2-(4-methylphenyl)-1,1,1,3,3,3-trifluoropropan-2-ol, 1 (100.0 g, 380 mmol) in CCl$_4$ (750 mL) was added NBS (68.6 g, 380 mmol) in portions and AIBN (0.63 g, 0.01 eq.) at RT. The resulting reaction mixture was heated to 80° C. and stirred for 2 h. The progress of the reaction was monitored by TLC (TLC system: 10% EtOAc/Pet ether, R$_f$ value: 0.35).

After completion of the reaction, the reaction mixture was concentrated under reduced pressure to afford the crude product. The crude product was diluted with water and extracted with dichloromethane (2×500 mL). The combined organic layers were washed with water, then brine, dried over anhydrous sodium sulfate and the solvent was removed under reduced pressure to afford crude 2-(4-(bromomethyl)phenyl)-1,1,1,3,3,3-hexafluoropropan-2-ol. The crude product was purified over silica gel (100-200 mesh) column chromatography eluting with pet ether to give 2-(4-(bromomethyl)phenyl)-1,1,1,3,3,3-hexafluoropropan-2-ol, 2 as a mixture of mono- and di-bromo derivatives. $^1$HNMR (400 MHz, CDCl3) δ: 7.75-7.64 (m, 2 H), 7.48 (d, 2 H, J=8.4 Hz), 4.5 (s, 2 H), 4.14-4.09 (m, 1 H).

Example 1

Preparation of 1,1,1,3,3,3-hexafluoro-2-(4-((6-(3-methyl-1H-pyrazol-5-yl)-3,4-dihydroquinolin-1(2H)-yl)methyl)phenyl)propan-2-ol Reaction Step 1

Preparation of 6-bromo-1,2,3,4-tetrahydroquinoline, 4

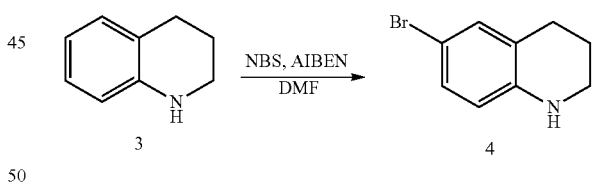

To a stirred solution of 1,2,3,4-tertrahydroquinoline, 3 (10.0 g, 75 mmol) in DMF (100 mL) was added NBS (17.4 g, 98 mmol) in portions at 0° C. and the mixture was stirred for 2 h. The progress of the reaction was monitored by TLC (TLC system: 10% EtOAc/Pet ether, R$_f$ value: 0.5).

After completion of the reaction, the reaction was quenched with water and extracted with ethyl acetate (2×200 mL). The combined organic layers were dried over anhydrous sodium sulfate and the solvent was removed under reduced pressure to afford crude product. The crude product was purified over silica gel (100-200 mesh) column chromatography by eluting with 3% EtOAc/Pet ether to give 6-bromo-1,2,3,4-tetrahydroquinoline, 4 as a light yellow liquid. $^1$HNMR (400 MHz, CDCl$_3$) δ: 7.05-7.01 (m, 2 H), 6.36 (d, 1 H, J=8.8 Hz), 3.29-3.27 (m, 2 H), 2.72 (t, 2 H, J=6 Hz), 1.94-1.89 (m, 2 H).

Reaction Step 2

Preparation of 2-(4-((6-bromo-3,4-dihydroquinolin-1(2H)-yl)methyl)phenyl)-1,1,1,3,3,3-hexafluoropropan-2-ol, 5

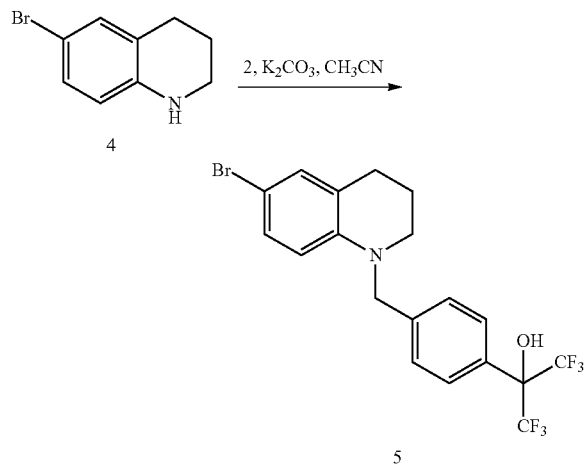

To a stirred solution of 6-bromo-1,2,3,4-tetrahydroquinoline, 4 (4.0 g, 18 mmol) in acetonitrile (100 mL) was added $K_2CO_3$ (7.8 g, 56 mmol), the mixture was cooled to 0° C. and stirred for 10 min. 2-(4-(bromomethyl)phenyl)-1,1,1,3,3,3-hexafluoropropan-2-ol, 2 (6.3 g, 1.0 eq.) was added dropwise and the reaction mixture was heated to 80° C. for 20 h. The progress of the reaction was monitored by TLC (TLC system: 10% EtOAc/Pet ether, $R_f$ value: 0.45). At the end of this period, 30% the starting compound 4 was present.

After 70% completion of reaction, the reaction mixture was filtered and the filtrate was concentrated under reduced pressure. The crude product was diluted with water and extracted with ethyl acetate (2×100 mL). The combined organic layers were dried over anhydrous sodium sulfate and the solvent was removed under reduced pressure. The crude product was purified over silica gel (100-200 mesh) column chromatography eluting with 2% EtOAc/Pet ether to give 2-(4-((6-bromo-3,4-dihydroquinolin-1(2H)-yl)methyl)phenyl)-1,1,1,3,3,3-hexafluoropropan-2-ol, 5 as a white solid. $^1$HNMR (400 MHz, $CDCl_3$) δ: 7.65 (d, 2 H, J=8.0 Hz), 7.30 (d, 2 H, J=8.0 Hz), 7.07 (s, 1 H), 7.03 (dd, 1 H, $J_1$=8.8, $J_2$=2.0 Hz), 6.29 (d, 1 H, J=8.8 Hz), 4.47 (s, 2 H), 3.36 (t, 2 h, J=5.6 Hz), 2.79 (t, 2 H, J=6.4 Hz), 2.01 (m, 2 H).

Reaction Step 3

Preparation of 1-(4-(1,1,1,3,3,3-hexafluoro-2-hydroxypropan-2-yl)benzyl)-1,2,3,4-tetrahydroquinoline-6-carbaldehyde, 6

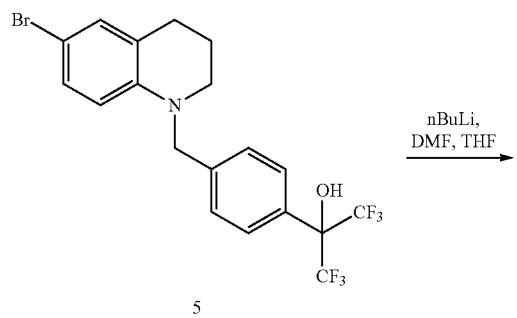

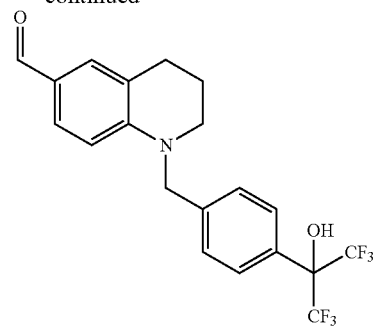

To a stirred solution of 2-(4-((6-bromo-3,4-dihydroquinolin-1(2H)-yl)methyl)phenyl)-1,1,1,3,3,3-hexafluoropropan-2-ol, 5 (0.2 g, 0.42 mmol) in THF (10 mL) was added a 1M solution of n-BuLi in hexanes (0.85 mL, 0.85 mmol) at −78° C. and the mixture was stirred for 10 min. DMF (0.59 mL, 1.8 eq.) was added dropwise at −78° C. and the reaction mixture slowly allowed to warm to RT and stir for 1 h. The progress of the reaction was monitored by TLC (20% EtOAc/Pet ether, $R_f$ value: 0.1)

After completion of the reaction, the reaction mixture was quenched with saturated ammonium chloride solution and extracted with ethyl acetate (2×50 mL). The combined organic layers were dried over anhydrous sodium sulfate and the solvent was removed under reduced pressure. The crude product was purified by silica gel (100-200 mesh) column chromatography eluting with 12-14% EtOAc/Pet ether to give 1-(4-(1,1,1,3,3,3-hexafluoro-2-hydroxypropan-2-yl)benzyl)-1,2,3,4-tetrahydroquinoline-6-carbaldehyde, 6 as a yellow oil. $^1$HNMR (400 MHz, $CDCl_3$) δ: 7.68 (d, 2 H, J=8.4 Hz), 7.28 (s, 1 H), 7.23 (d, 2 H, J=8 Hz), 6.41 (d, 1 H, J=8.4 Hz), 4.51 (s, 2 H), 3.51 (s, 1 H) 3.46 (t, 2 H, J=6 Hz), 2.81 (t, 2 H, J=6 H), 2.03 (t, 2 H, J=5.2 Hz).

Reaction Step 4

Preparation of (E)-4-(1-(4-(1,1,1,3,3,3-hexafluoro-2-hydroxypropan-2-yl)benzyl)-1,2,3,4-tetrahydroquinolin-6-yl)but-3-en-2-one, 7

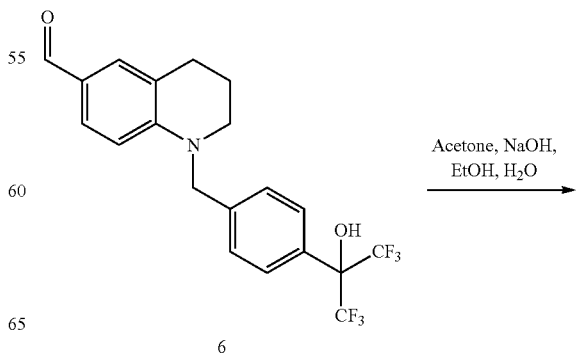

43

-continued

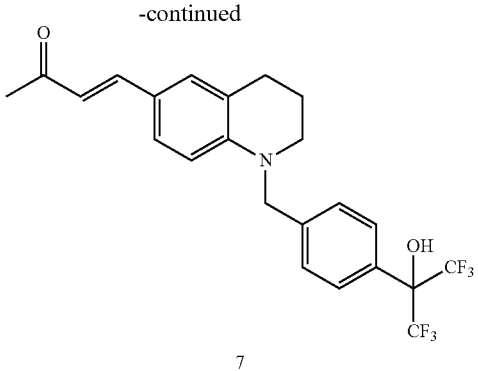

7

A stirred solution of acetone (0.10 mL, 1.4 mmol), NaOH (0.2 g, 5.0 mmol) and water (4 mL) was cooled to 0° C. 1-(4-(1,1,1,3,3,3-Hexafluoro-2-hydroxypropan-2-yl)benzyl)-1,2,3,4-tetrahydroquinoline-6-carbaldehyde, 6 (0.2 g, 0.48 mmol) dissolved in ethanol (5 mL), was added at 0° C. and the mixture was stirred for 10 min. The resulting reaction mixture was allowed to warm to RT and stir for 8 h. The progress of the reaction was monitored by TLC (TLC system: 50% EtOAc/Pet ether, $R_f$ value: 0.25).

After completion of the reaction, the reaction mixture was diluted with ethyl acetate and washed with water. The organic layer was dried over anhydrous sodium sulfate and the solvent was removed under reduced pressure to give crude (E)-4-(1-(4-(1,1,1,3,3,3-hexafluoro-2-hydroxypropan-2-yl)benzyl)-1,2,3,4-tetrahydroquinolin-6-yl)but-3-en-2-one, 7 as a yellow liquid. LC-MS: 96.7% at 215 nm (m/z 418 [M+H]).

Reaction Step 5

Preparation of 1,1,1,3,3,3-hexafluoro-2-(4-((6-(3-methyl-1H-pyrazol-5-yl)-3,4-dihydroquinolin-1(2H)-yl)methyl)phenyl)propan-2-ol, 8

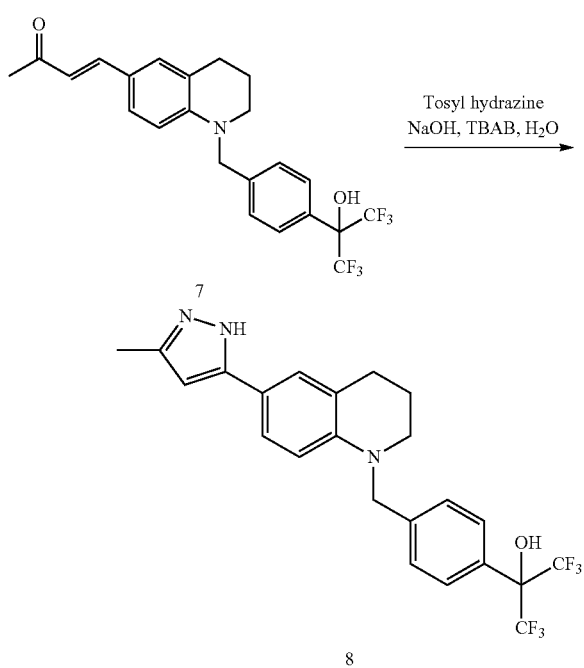

44

To a solution of (E)-4-(1-(4-(1,1,1,3,3,3-hexafluoro-2-hydroxypropan-2-yl)benzyl)-1,2,3,4-tetrahydroquinolin-6-yl)but-3-en-2-one, 7 (0.45 g, 0.98 mmol) in water (10 mL), NaOH (0.06 g, 1.5 mmol), TBAB (0.475 g, 1.5 mmol), tosyl hydrazine (0.22 g, 3.0 mmol) were added at RT. The resulting reaction mixture was heated to 85° C. for 12 h. The progress of the reaction was monitored by TLC, (TLC system: 50% EtOAc/Pet ether, $R_f$ value: 0.5)

After completion of the reaction, the reaction mixture was diluted with water and extracted with ethyl acetate (2×30 mL). The combined organic layers were dried over anhydrous sodium sulfate and the solvent was removed under reduced pressure. The crude product was purified by preparative HPLC followed by preparative TLC; to afford 1,1,1,3,3,3-hexafluoro-2-(4-((6-(3-methyl-1H-pyrazol-5-yl)-3,4-dihydroquinolin-1(2H)-yl)methyl)phenyl)propan-2-ol, 8 as an off white solid. $^1$H NMR (400 MHz, DMSO-$d_6$) δ:12.5 (br, s, 1 H), 8.63 (s, 1 H), 7.63 (d, 2 H, J=8 Hz), 7.39 (d, 2 H, J=8.4 Hz), 7.29 (s, 1 H), 7.22 (d, 1 H, J=8.4 Hz), 6.43 (d, 1 H, J=8.8 Hz), 6.17 (s, 1 H), 4.56 (s, 2 H), 3.40 (t, 2 H, J=5.2 Hz), 2.78 (t, 2 H, J=6 Hz), 2.17 (s, 3 H), 1.97 (t, 2 H, J=5.6 Hz). LC-MS: 95.94% at 215 nm and 95.36% at 254 nm (m/z=470.1, [M+H]$^+$).

Example 2

Preparation of 2-(4-((6-(1H-pyrazol-4-yl)-3,4-dihydroquinolin-1(2H)-yl)methyl)phenyl)-1,1,1,3,3,3-hexafluoropropan-2-ol Reaction Step 1

Preparation of tert-butyl 4-(4,4,5,5-tetramethyl-1,3,2-dioxaborolan-2-yl)-1H-pyrazole-1-carboxylate, 10

To a stirred solution of 4-(4,4,5,5-tetramethyl-1,3,2-dioxaborolan-2-yl)-1H-pyrazole, 9 (2.0 g, 10 mmol) in DMF (50 mL) was added DMAP (3.14 g, 25 mmol), the mixture was cooled to 0° C. and stirred for 10 min. (Boc)$_2$O (2.9 mL, 13 mmol) was added dropwise and the mixture was stirred for 15 min at same temperature. The resulting reaction mixture was allowed to warm to RT and stir overnight. The progress of the reaction was monitored by TLC (TLC system: 50% EtOAc/Pet ether, $R_f$ value: 0.8)

After completion of the reaction, the reaction mixture was diluted with ice cold water and extracted with ethyl acetate (2×100 mL). The combined organic layers were dried over anhydrous sodium sulfate and the solvent was removed under reduced pressure. The crude product was purified over silica gel (100-200 mesh) column chromatography eluting with 10% EtOAc/Pet ether to give tert-butyl 4-(4,4,5,5-tetramethyl-1,3,2-dioxaborolan-2-yl)-1H-pyrazole-1-carboxylate, 10 as a white solid.

Reaction Steps 2 and 3

Preparation of 2-(4-((6-(1H-pyrazol-4-yl)-3,4-dihydroquinolin-1 (2H)-yl)methyl)phenyl)-1,1,1,3,3,3-hexafluoropropan-2-ol, 11

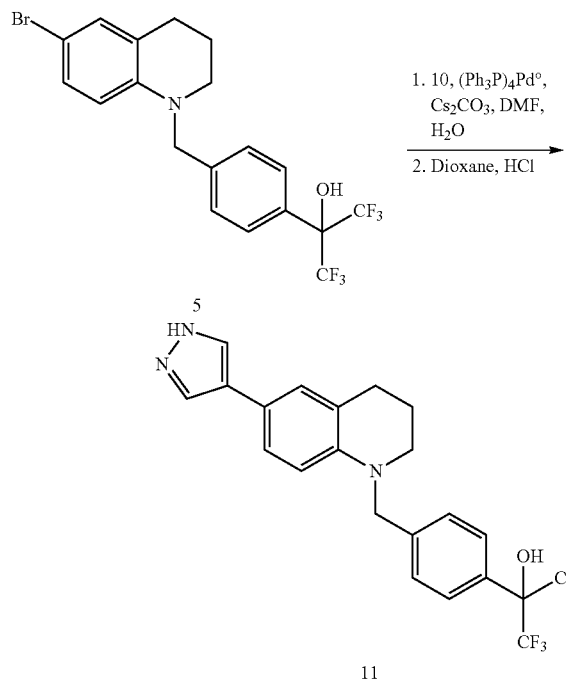

To a stirred solution of 2-(4-((6-bromo-3,4-dihydroquinolin-1(2H)-yl)methyl)phenyl)-1,1,1,3,3,3-hexafluoropropan-2-ol 5 (0.8 g, 1.7 mmol) and tert-butyl 4-(4,4,5,5-tetramethyl-1,3,2-dioxaborolan-2-yl)-1H-pyrazole-1-carboxylate 10 (0.65 g, 2.2 mmol) in DMF (30 mL) and water (3 mL) was added $Cs_2CO_3$ (1.67 g, 5.1 mmol) the solution was deoxygenated by the passage of argon for 2 h. Tetrakis-triphenylphosphine palladium (0.2 g, 0.17 mmol) was added and the mixture was heated to 80° C. and stirred overnight. The progress of the reaction was monitored by TLC (TLC system: 50% EtOAc/Pet ether, $R_f$ value: 0.2).

By LC-MS 50% de-Boc product was observed. The reaction mass was filtered through a celite bed and concentrated. The crude product was treated with 2M HCl in dioxane and stirred for 2 h.

After completion of reaction, the reaction mixture was concentrated under reduced pressure, the residue was diluted with ethyl acetate and washed with saturated $NaHCO_3$ solution. The organic layer was dried over anhydrous sodium sulfate and the solvent was removed under reduced pressure to afford crude product. The crude product was purified by preparative TLC and to give 2-(4-((6-(1H-pyrazol-4-yl)-3,4-dihydroquinolin-1(2H)-yl)methyl)phenyl)-1,1,1,3,3,3-hexafluoropropan-2-ol, 11 as an off-white solid. $^1$H NMR (400 MHz, DMSO-$d_6$) δ: 12.68 (s, 1 H), 8.62 (s, 1 H), 7.79 (br, s, 2 H), 7.63 (d, 2 H, J=8.4 Hz), 7.39 (d, 2 H, J=8.4 Hz), 7.15 (s, 1 H), 7.09 (dd, 1 H, $J_1$=8.4, $J_2$=2.4 Hz), 6.41 (d, 2 H, J=8.4 Hz), 4.54 (s, 2 H), 3.38 (t, 2 H, J=5.6 Hz), 2.77 (t, 2 H, J=6 Hz), 1.98-1.94 (m, 2H). LC-MS: 97.22% at 215 nm and 95.73% at 254 nm (m/z=456.1, [M+H]$^+$).

Example 3

Preparation of 1,1,1,3,3,3-hexafluoro-2-(4-((6-(3-methyl-1H-1,2,4-triazol-5-yl)-3,4-dihydroquinolin-1 (2H)-yl)methyl)phenyl)propan-2-ol Reaction Step 1

Preparation of 6-bromo-3,4-dihydroquinolin-2(1H)-one, 13

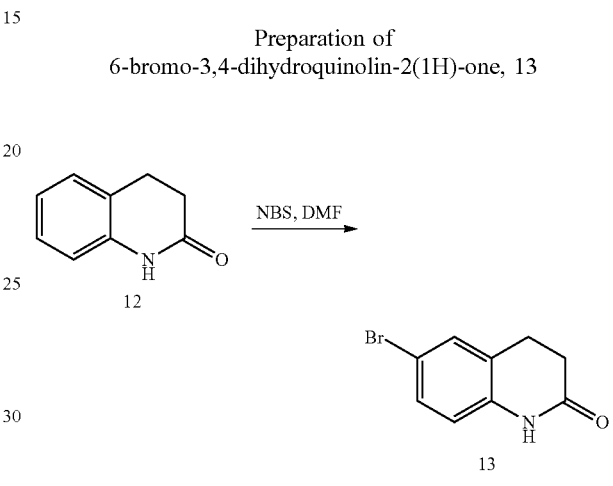

3,4-Dihydroquinolin-2(1H)-one, 12 (25.0 g, 170 mmol) in DMF (50 mL) was added to a stirred solution of NBS (33.2 g, 186 mmol) in DMF (250 mL) at 0° C. and the mixture was stirred for 1 h. The progress of the reaction was monitored by TLC (TLC system: 50% EtOAc/Pet ether, $R_f$ value: 0.35).

After completion of the reaction, the reaction mixture was quenched with water and then solid formed. The solid was filtered and dried under vacuum to afford the crude product. The crude product was purified over silica gel (100-200 mesh) column chromatography eluting with 3% EtOAc/Pet ether to give 6-bromo-3,4-dihydroquinolin-2(1H)-one, 13 as a white solid. $^1$H NMR (400 MHz, CDCl$_3$) δ: 8.73 (s, 1 H), 7.28 (dd, 2 H, $J_1$=10.8, $J_2$=2.4 Hz), 6.69 (d, 1 H, J=8.0 Hz), 2.95 (t, 2 H, J=7.2 Hz), 2.65-2.61 (m, 2 H); LC-MS: 96.7% at 215 nm (m/z 418 [M+H]).

Reaction Step 2

Preparation of 6-bromo-1-(4-(1,1,1,3,3,3-hexafluoro-2-hydroxypropan-2-yl)benzyl)-3,4-dihydroquinolin-2(1H)-one, 14

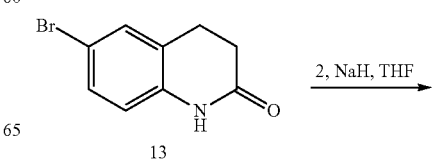

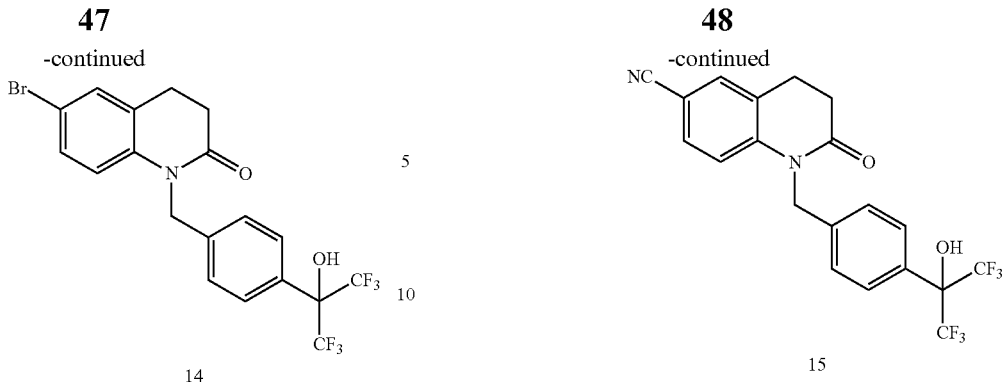

A solution of 6-bromo-3,4-dihydroquinolin-2(1H)-one, 13 (10.0 g, 44 mmol) in THF (25 mL) was added to stirred solution of 60% NaH (3.53 g, 88 mmol) in THF (100 mL) at 0° C. and the mixture was stirred for 30 min. A solution of 2-(4-(bromomethyl)phenyl)-1,1,1,3,3,3-hexafluoropropan-2-ol (2) (18.4 g, 55.3 mmol) in THF (25 mL) was added and slowly heated to 65° C. overnight. The progress of the reaction was monitored by TLC (TLC system: 30% EtOAc/Pet ether, $R_f$ value: 0.45).

After completion of the reaction, the reaction mixture was poured into ice cold water and extracted with ethyl acetate (2×200 mL). The combined organic layers were dried over anhydrous sodium sulfate and the solvent was removed under reduced pressure. The crude product was washed with pet ether followed by dichloromethane to afford 6-bromo-1-(4-(1,1,1,3,3,3-hexafluoro-2-hydroxypropan-2-yl)benzyl)-3,4-dihydroquinolin-2(1H)-one, 14. $^1$H NMR (400 MHz, DMSO-$d_6$) δ: 8.65 (s, 1 H), 7.61 (d, 2 H, J=8.4 Hz), 7.47 (d, 1 H, J=2.0 Hz), 7.35-7.30 (m, 3 H), 6.85 (d, 1 H, J=8.4 Hz), 5.17 (s, 2 H), 2.98 (t, 2 H, J=6.8 Hz), 2.71 (m, 2 H).

Reaction Step 3

Preparation of 1-(4-(1,1,1,3,3,3-hexafluoro-2-hydroxypropan-2-yl)benzyl)-2-oxo-1,2,3,4-tetrahydroquinoline-6-carbonitrile, 15

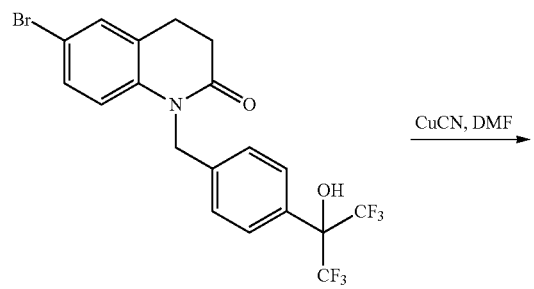

To a stirred solution of 6-bromo-1-(4-(1,1,1,3,3,3-hexafluoro-2-hydroxypropan-2-yl)benzyl)-3,4-dihydroquinolin-2(1H)-one 14 (2.0 g, 4.0 mmol) in DMF (10 mL) was added CuCN (1.2 g, 12.0 mmol) in a sealed tube. The resulting reaction mixture was heated to 150° C. for 2 h. The progress of the reaction was monitored by TLC (TLC system: 30% EtOAc/Pet ether, $R_f$ value: 0.4).

After completion of reaction, the reaction mixture was cooled to RT, quenched with aq. ammonia and extracted with ethyl acetate (2×50 mL). The combined organic layers were dried over anhydrous sodium sulfate and the solvent was removed under reduced pressure. The crude product was purified over silica gel (100-200 mesh) column chromatography eluting with 10% EtOAc/Pet ether to give 1-(4-(1,1,1,3,3,3-hexafluoro-2-hydroxypropan-2-yl)benzyl)-2-oxo-1,2,3,4-tetrahydroquinoline-6-carbonitrile, 15 that was used directly in the next step.

Reaction Step 4

Preparation of 1-(4-(1,1,1,3,3,3-hexafluoro-2-hydroxypropan-2-yl)benzyl)-6-(3-methyl-1H-1,2,4-triazol-5-yl)-3,4-dihydroquinolin-2(1H)-one, 16

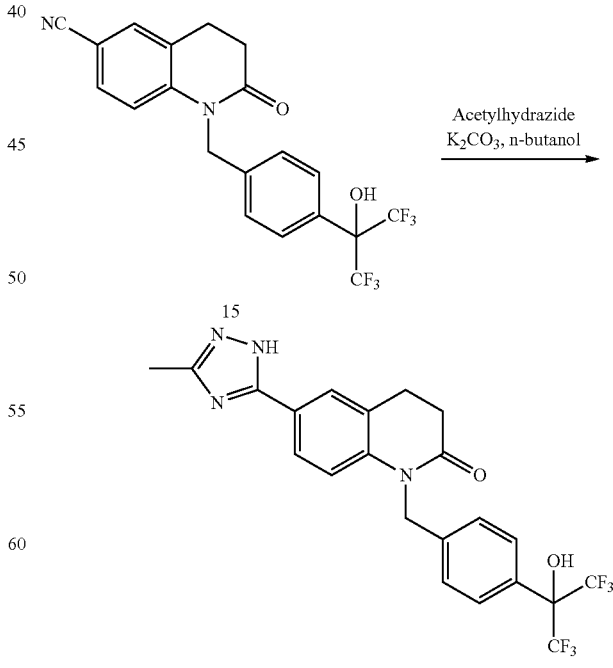

To a stirred solution of 1-(4-(1,1,1,3,3,3-hexafluoro-2-hydroxypropan-2-yl)benzyl)-2-oxo-1,2,3,4-tetrahydroquinoline-6-carbonitrile, 15 (0.3 g, 0.70 mmol) in n-butanol (100 mL) was added K$_2$CO$_3$ (0.96 g, 7.0 mmol) and acetylhydrazide (0.33 g, 7.3 mmol) at RT. The resulting reaction mixture was heated to 140° C. and stirred for 40 h. The progress of the reaction was monitored by TLC (TLC system: 5% MeOH/dichloromethane (KMnO4 active), R$_f$ value: 0.5).

After completion of reaction, the reaction mixture was cooled to RT and concentrated under reduced pressure. The crude product was diluted with water and extracted with ethyl acetate (2×50 mL). The combined organic layers were dried over anhydrous sodium sulfate and the solvent was removed under reduced pressure. The crude product was purified over silica gel (100-200 mesh) column chromatography eluting with 70% EtOAc/Pet ether to give 1-(4-(1,1,1,3,3,3-hexafluoro-2-hydroxypropan-2-yl)benzyl)-6-(3-methyl-1H-1,2,4-triazol-5-yl)-3,4-dihydroquinolin-2(1H)-one, 16 as an off white solid. $^1$H NMR (400 MHz, DMSO-d$_6$) δ: 13.56 (s, 1 H), 8.65 (s, 1 H), 7.84 (s, 1H), 7.71 (d, 1 H, J=8.0 Hz), 7.62 (d, 2 H, J=8.0 Hz), 7.37 (d, 2 H, J=8.4 Hz), 6.97 (d, 1 H, J=8.4 Hz), 5.21 (s, 2 H), 3.03 (t, 2 H, J=7.6 Hz), 2.74 (t, 2 H, J=7.6 Hz), 2.37 (s, 3 H). LC-MS: 96.79% at 215 nm and 92.43% at 254 nm (m/z=485.1, [M+H]$^+$).

Reaction Step 5

Preparation of 1,1,1,3,3,3-hexafluoro-2-(4-((6-(3-methyl-1H-1,2,4-triazol-5-yl)-3,4-dihydroquinolin-1(2H)-yl)methyl)phenyl)propan-2-ol, 17

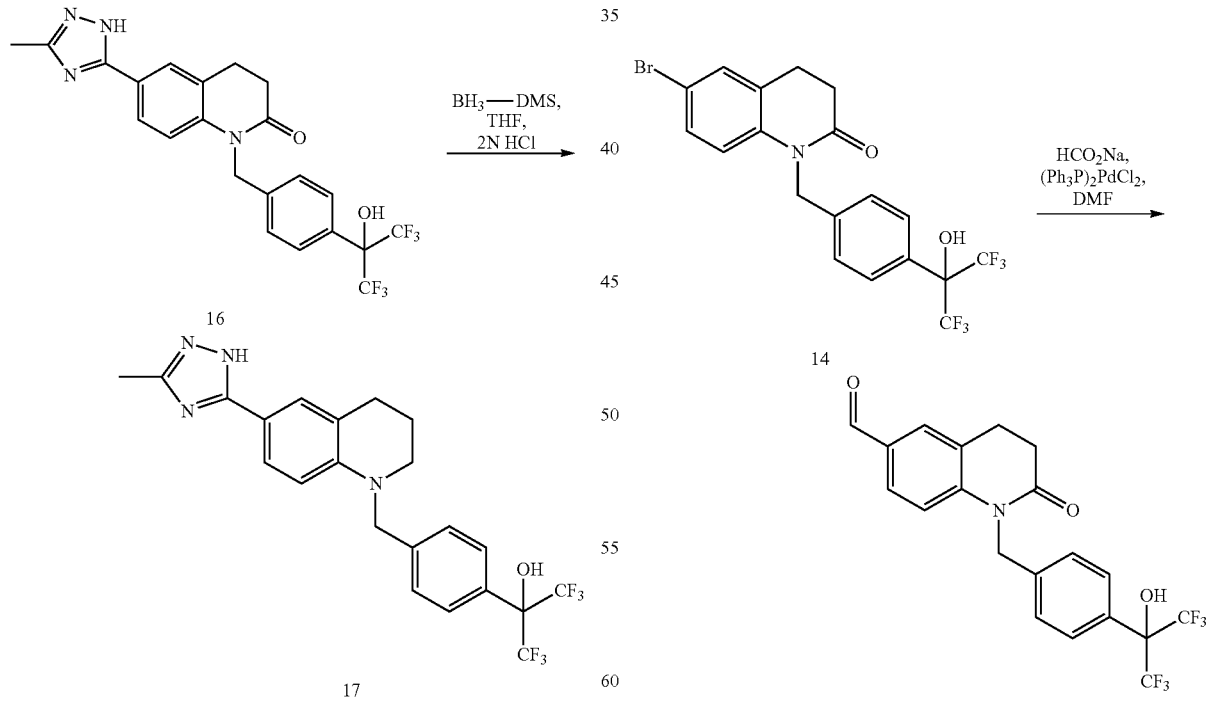

To a stirred solution of 1-(4-(1,1,1,3,3,3-hexafluoro-2-hydroxypropan-2-yl)benzyl)-6-(3-methyl-1H-1,2,4-triazol-5-yl)-3,4-dihydroquinolin-2(1H)-one, 16 (0.14 g, 0.20 mmol) in THF (20 mL) was added BH$_3$-DMS (2M) (0.31 mL, 0.6 mmol) at 0° C. and the mixture was stirred for 10 min. The resulting reaction mixture was heated to reflux and was stirred for 2 h. The reaction mixture was quenched with methanol and concentrated under reduced pressure. 2N HCl (10 mL) was added to crude product and the mixture heated to 100° C. for 1 h. The progress of the reaction was monitored by TLC (TLC system: 50% EtOAc/Pet ether, R$_f$ value: 0.5).

After completion of reaction, the reaction mixture was cooled to RT, the pH was adjusted to 10 with NaHCO$_3$ solution, and it was extracted with ethyl acetate (2×50 mL). The combined organic layers were dried over anhydrous sodium sulfate and the solvent was removed under reduced pressure. The crude product was purified by preparative HPLC to afford 1,1,1,3,3,3-hexafluoro-2-(4-((6-(3-methyl-1H-1,2,4-triazol-5-yl)-3,4-dihydroquinolin-1(2H)-yl)methyl)phenyl)propan-2-ol, 17 as a brown semi-solid. $^1$H NMR (400 MHz, DMSO-d$_6$) δ: 7.67-7.62 (m, 3 H), 7.51 (s, 1 H), 7.34-7.31 (m, 3 H), 6.49 (d, 1 H, J=8.8 Hz), 4.57 (s, 2 H), 3.49 (s, 1 H), 3.42 (t, 2 H, J=6 Hz), 2.88 (t, 2 H, J=6 Hz), 2.47 (s, 3 H), 2.10-2.00 (m, 3 H). LC-MS: 95.06% at 215 nm and 95.17% at 254 nm (m/z=471.1, [M+H]$^+$).

Example 4

Preparation of 1-(4-(1,1,1,3,3,3-hexafluoro-2-hydroxypropan-2-yl)benzyl)-6-(3-methyl-1H-pyrazol-5-yl)-3,4-dihydroquinolin-2(1H)-one Reaction Step 1

Preparation of 1-(4-(1,1,1,3,3,3-hexafluoro-2-hydroxypropan-2-yl)benzyl)-2-oxo-1,2,3,4-tetrahydroquinoline-6-carbaldehyde, 18

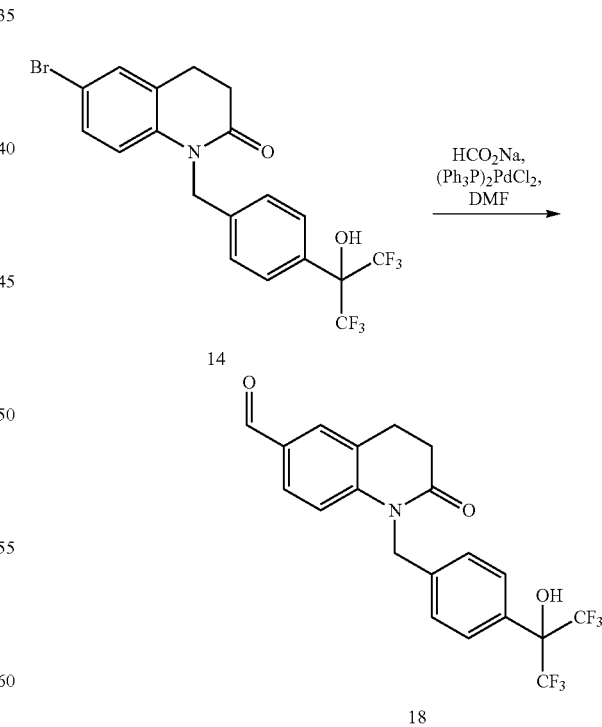

In a steel bomb a mixture of 6-bromo-1-(4-(1,1,1,3,3,3-hexafluoro-2-hydroxypropan-2-yl)benzyl)-3,4-dihydroquinolin-2(1H)-one, 14 (1.0 g, 2.1 mmol) sodium formate (0.09 g, 1.3 mmol) and PdCl$_2$P(Ph$_3$)$_2$ (0.12 g, 0.17 mmol) in DMF (10 mL) was deoxygenated with argon for 20 min and then CO gas was introduced into the bomb, the bomb was sealed. The pressure adjusted to 250 psi and the temperature raised to 100° C. The reaction mixture was stirred for 30 h at 100° C. The progress of the reaction was monitored by TLC (TLC system: 50% EtOAc/Pet ether, $R_f$ value: 0.4).

After completion of the reaction, the reaction mixture was diluted with water and extracted with ethyl acetate (2×80 mL). The combined organic layers were washed with brine, dried over anhydrous sodium sulfate and the solvent was removed under reduced pressure. The crude product was purified over silica gel (100-200 mesh) column chromatography eluting with 25% EtOAc/Pet ether to give 1-(4-(1,1,1,3,3,3-hexafluoro-2-hydroxypropan-2-yl)benzyl)-2-oxo-1,2,3,4-tetrahydroquinoline-6-carbaldehyde, 18 as a colorless liquid which was used directly in the next step.

Reaction Step 2

Preparation of (E)-1-(4-(1,1,1,3,3,3-hexafluoro-2-hydroxypropan-2-yl)benzyl)-6-(3-oxobut-1-en-1-yl)-3,4-dihydroquinolin-2(1H)-one, 19

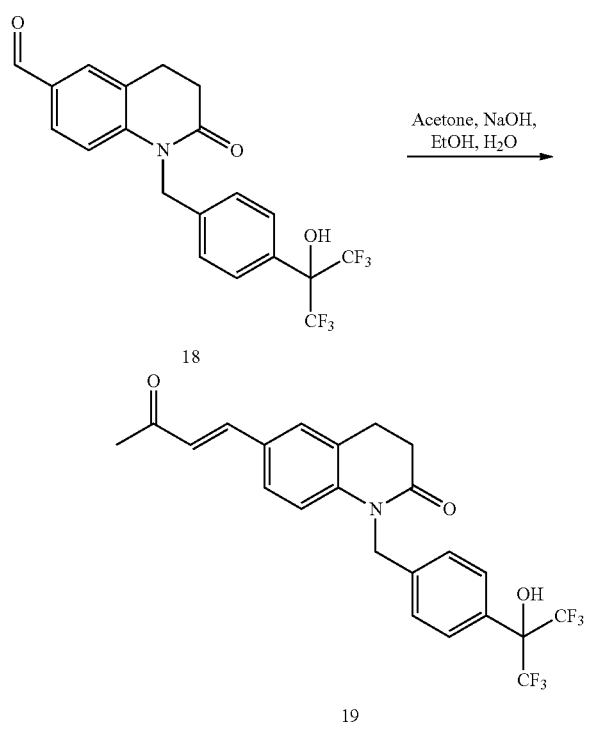

To a stirred solution of acetone (0.2 g, 2.7 mmol) and NaOH (0.1 g, 2.5 mmol) in water (4 mL) was added 1-(4-(1,1,1,3,3,3-hexafluoro-2-hydroxypropan-2-yl)benzyl)-2-oxo-1,2,3,4-tetrahydroquinoline-6-carbaldehyde, 18 (0.1 g, 0.23 mmol) dissolved in EtOH (15 mL) at 0° C. The resulting reaction mixture was allowed to warm to RT and was stirred overnight. The progress of the reaction was monitored by TLC (TLC system: 50% EtOAc/Pet ether, $R_f$ value: 0.3).

After completion of the reaction, reaction the pH was adjusted to 6 with $KHSO_4$ solution and extracted with MTBE (2×50 mL). The organic layer was dried over anhydrous sodium sulfate and the solvent was removed under reduced pressure to give (E)-1-(4-(1,1,1,3,3,3-hexafluoro-2-hydroxypropan-2-yl)benzyl)-6-(3-oxobut-1-en-1-yl)-3,4-dihydroquinolin-2(1H)-one, 19 as a white solid. $^1$H NMR (400 MHz, $CDCl_3$) δ: 7.67 (d, 2 H, J=8.4 Hz), 7.42 (d, 1 H, J=16.4 Hz), 7.39 (m, 1 H), 7.33-7.27 (m, 3 H), 6.85 (d, 1 H, J=8.4 Hz), 6.63 (d, 1 H, J=16.0 Hz), 5.21 (s, 2H), 3.03 (t, 2 H, J=8.4 Hz), 2.82 (t, 2 H, J=8.0 Hz), 2.35 (s, 3 H). LC-MS: 73.98% (m/z=472.1, [M+H]$^+$).

Reaction Step 3

Preparation of 1-(4-(1,1,1,3,3,3-hexafluoro-2-hydroxypropan-2-yl)benzyl)-6-(3-methyl-1H-pyrazol-5-yl)-3,4-dihydroquinolin-2(1H)-one, 20

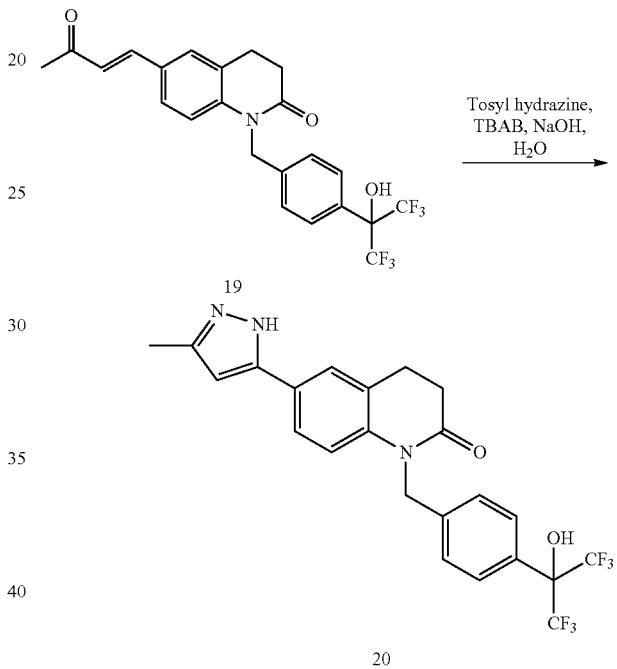

To a stirred solution of (E)-1-(4-(1,1,1,3,3,3-hexafluoro-2-hydroxypropan-2-yl)benzyl)-6-(3-oxobut-1-en-1-yl)-3,4-dihydroquinolin-2(1H)-one, 19 (0.15 g, 0.32 mmol) in water (5 mL) was added tosyl hydrazide (0.186 g, 0.38 mmol), TBAB (0.153 g, 0.48 mmol) and NaOH (0.019 g, 0.48 mmol) simultaneously at RT. The resulting reaction mixture was heated to 80° C. and stirred for 2 h. The progress of the reaction was monitored by TLC (TLC system: 50% EtOAc/Pet ether, $R_f$ value: 0.5).

After completion of reaction, brine solution was added to the reaction mixture and it was extracted with ethyl acetate (2×50 mL). The combined organic layers were dried over anhydrous sodium sulfate and the solvent was removed under reduced pressure. The crude product was purified over silica gel (100-200 mesh) column chromatography eluting with pure ethyl acetate to afford 1-(4-(1,1,1,3,3,3-hexafluoro-2-hydroxypropan-2-yl)benzyl)-6-(3-methyl-1H-pyrazol-5-yl)-3,4-dihydroquinolin-2(1H)-one, 20 as an off-while solid. $^1$H NMR (400 MHz, DMSO-$d_6$) δ: 12.44 (s, 1 H), 8.64 (s, 1 H), 7.62 (d, 3 H, J=8.0 Hz), 7.48 (d, 1 H, J=8.4 Hz), 7.37 (d, 2 H, J=8.4 Hz), 6.91 (d, 1 H, J=8.4 Hz), 6.35 (s, 1 H), 5.20 (s, 2 H), 3.00 (t, 2 H, J=7.2 Hz), 2.73 (t, 2 H, J=7.2 Hz), 2.23 (br s, 3 H), 1.23 (s, 1 H). LC-MS: 95.13% at 215 nm and 92.96% at 254 nm (m/z=484.1, [M+H]⁺).

Example 5

Preparation of 1-(4-(1,1,1,3,3,3-hexafluoro-2-hydroxypropan-2-yl)benzyl)-6-(1H-pyrazol-4-yl)-3,4-dihydroquinolin-2(1H)-one

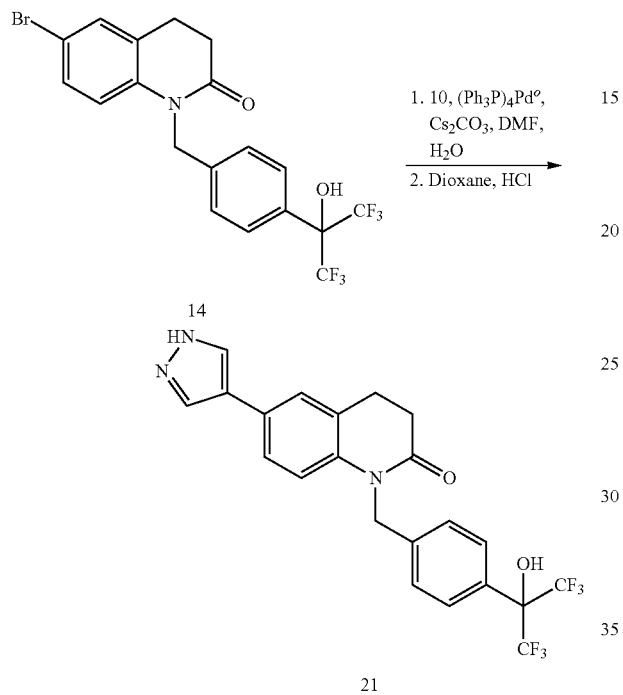

A suspension of 6-bromo-1-(4-(1,1,1,3,3,3-hexafluoro-2-hydroxypropan-2-yl)benzyl)-3,4-dihydroquinolin-2(1H)-one, 14 (0.5 g, 1.0 mmol) and tert-butyl 4-(4,4,5,5-tetramethyl-1,3,2-dioxaborolan-2-yl)-1H-pyrazole-1-carboxylate, 10 (0.44 g, 1.5 mmol) in DMF (5 mL) was deoxygenated by passage of argon for 20 min, PdCl$_2$ (dppf) (0.081 g, 0.1 mmol) and potassium acetate (0.30 g, 3.1 mmol) was added at RT. The resulting reaction mixture was heated to 60° C. for 4 h. The progress of the reaction was monitored by TLC (TLC system: 70% % EtOAc/Pet ether, R$_f$ value: 0.1)

After completion of the reaction, the reaction mixture was diluted with ethyl acetate and washed with ice cold water. The organic layer was dried over anhydrous sodium sulfate and the solvent was removed under reduced pressure to afford crude product. A solution of hydrochloric acid in dioxane (1 mL) was added to the crude product and the mixture was stirred for 30 min. The reaction mixture was concentrated under reduced pressure. The crude product was diluted with ethyl acetate and washed with saturated sodium bicarbonate solution. The organic layer was dried over sodium sulfate and concentrated under reduced pressure to afford a crude product that was titurated with diethyl ether to afford 1-(4-(1,1,1,3,3,3-hexafluoro-2-hydroxypropan-2-yl)benzyl)-6-(1H-pyrazol-4-yl)-3,4-dihydroquinolin-2(1H)-one, 21 as an off-white solid. ¹H NMR (400 MHz, DMSO d$_6$) δ: 12.9 (s, 1 H), 8.64 (s, 1 H), 8.08 (br, s, 1 H), 7.83 (br, s, 1 H), 7.61 (d, 2 H, J=8.4 Hz), 7.48 (d, 1 H, J=2.0 Hz) 7.40-7.30 (m, 3 H), 7.07 (br, s, 1 H), 6.88 (d, 1 H, J=6.6 Hz), 5.19 (s, 2 H), 2.98 (t, 2 H, J=7.6 Hz), 2.71 (t, 2 H, J=8.0 Hz). LC-MS: 97.46% at 215 nm and 97.12% at 254 nm (m/z=470.1, [M+H]⁺).

Example 6

Preparation of Preparation of 1-(4-(1,1,1,3,3,3-hexafluoro-2-hydroxypropan-2-yl)benzyl)-6-(3-methyl-1H-1,2,4-triazol-5-yl)-3,4-dihydroquinolin-2(1H)-one

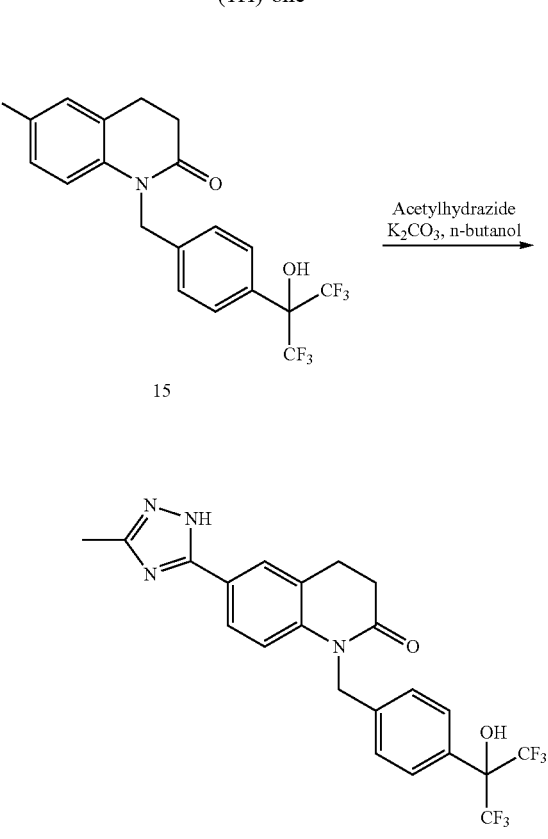

K$_2$CO$_3$ (0.97 g, 7.0 mmol) was added to a stirred solution of 1-(4-(1,1,1,3,3,3-hexafluoro-2-hydroxypropan-2-yl)benzyl)-2-oxo-1,2,3,4-tetrahydroquinoline-6-carbonitrile, 15 (0.3 g, 0.70 mmol) and acetylhydrazide (0.52 mL, 7.0 mmol) in n-butanol (25 mL) at RT. The resulting reaction mixture was heated to 125° C. and stirred for 3 days. The progress of the reaction was monitored by TLC (TLC system: 5% MeOH/dicloromethane, R$_f$ value: 0.15).

After completion of the reaction, the reaction mixture was concentrated under reduced pressure to afford the crude product. The crude product was purified over silica gel (60-120 mesh) column chromatography by eluting with 50% EtOAc/Pet ether to give 1-(4-(1,1,1,3,3,3-hexafluoro-2-hydroxypropan-2-yl)benzyl)-6-(3-methyl-1H-1,2,4-triazol-5-yl)-3,4-dihydroquinolin-2(1H)-one, 16 as an off-white solid. 1H NMR (400 MHz, DMSO-d6) δ: 13.56 (s, 1 H), 8.65 (s, 1 H), 7.84 (s, 1 H), 7.71 (d, 1 H, J=8.0 Hz), 7.62 (d, 2 H, J=8.0 Hz), 7.37 (d, 2 H, J=8.4 Hz), 6.97 (d, 1 H, J=8.4 Hz), 5.21 (s, 2 H), 3.03 (t, 2 H, J=7.6 Hz), 2.74 (t, 2 H, J=7.6 Hz), 2.37 (s, 3 H). LC-MS: 96.79% at 215 nm and 92.43% at 254 nm (m/z=485.1, [M+H]⁺).

Example 7

Preparation of 1,1,1,3,3,3-hexafluoro-2-(4-((5-(3-methyl-1H-pyrazol-5-yl)indolin-1-yl)methyl)phenyl)propan-2-ol

Reaction Step 1

Preparation of 2-(4-((5-bromoindolin-1-yl)methyl)phenyl)-1,1,1,3,3,3-hexafluoropropan-2-ol, 23

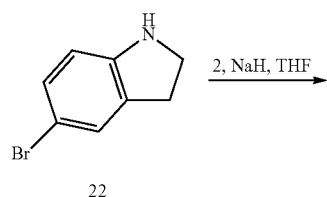

22

23

Reaction Step 2

Preparation of 1-(4-(1,1,1,3,3,3-hexafluoro-2-hydroxypropan-2-yl)benzyl)indoline-5-carbaldehyde, 24

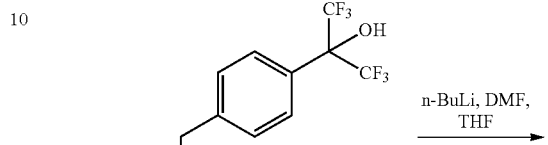

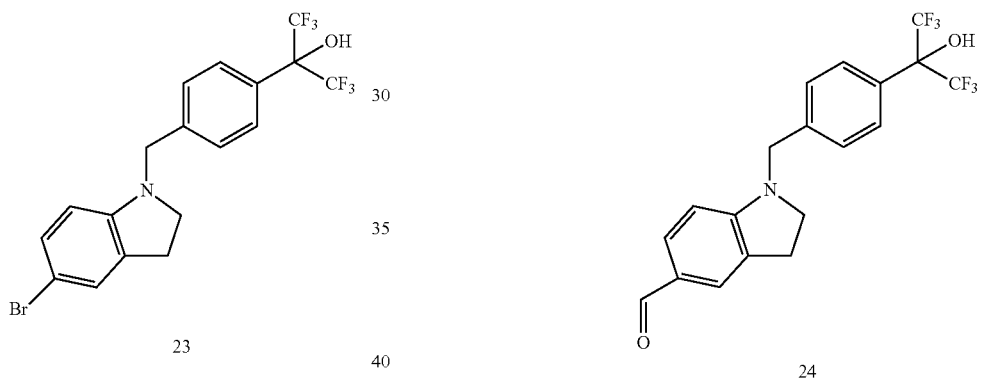

60% NaH (4.04 g, 101 mmol) was added to a stirred solution of 2-(4-(bromomethyl)phenyl)-1,1,1,3,3,3-hexafluoropropan-2-ol, 2 (5.0 g, 25.3 mmol) and 5-bromoindoline, 22 (11.02 g, 32.8 mmol) in THF (50 mL) at 0° C. The resulting reaction mixture was refluxed for 2 h. The progress of the reaction was monitored by TLC (TLC system: 20% EtOAc/Pet ether, $R_f$ value: 0.55).

After 70% completion of reaction, the reaction mixture was quenched with ice and extracted with ethyl acetate (2×300 mL). The combined organic layers were washed with brine, dried over anhydrous sodium sulfate and the solvent was removed under reduced pressure. The crude product was purified by column chromatography over silica gel (100-200 mesh) eluting with 10% EtOAc/Pet ether to give 2-(4-((5-bromoindolin-1-yl)methyl)phenyl)-1,1,1,3,3,3-hexafluoropropan-2-ol, 23 as a pale yellow liquid. $^1$H NMR (400 MHz, CDCl$_3$) δ: 7.68 (d, 2 H, J=8.8 Hz), 7.42 (d, 2 H J=8.4 Hz), 7.17 (s, 1 H), 7.14 (d, 1 H, J=8.4 Hz), 6.32 (d, 1 H, J=8.4 Hz), 4.25 (s, 2 H), 3.41 (s, 1 H) 3.35 (d, 2 H, J=8.0 Hz), 2.98 (t, 2 H, J=8.0 Hz).

To a stirred solution of 2-(4-((5-bromoindolin-1-yl)methyl)phenyl)-1,1,1,3,3,3-hexafluoropropan-2-ol, 23 (3.0 g, 6.6 mmol) in THF (15 mL) was added a solution of 1M n-BuLi in hexanes (13.2 mL, 13.2 mmol) at −78° C. and the mixture was stirred for 30 min. DMF (0.29 mL, 11.8 mmol) was added dropwise and the mixture was stirred for 15 min at the same temperature. The resulting reaction mixture was allowed warm to RT and stir for 3 h. The progress of the reaction was monitored by TLC (TLC system: 30% EtOAc/Pet ether, $R_f$ value: 0.3).

After completion of the reaction, the reaction mixture was quenched with saturated ammonium chloride solution and extracted with ethyl acetate (2×150 mL). The combined organic layers were dried over anhydrous sodium sulfate and the solvent was removed under reduced pressure to give crude 1-(4-(1,1,1,3,3,3-hexafluoro-2-hydroxypropan-2-yl)benzyl)indoline-5-carbaldehyde, 24 as a liquid. LC-MS: 71.77% at 215 nm (m/z=404.1 [M+H]$^+$).

Reaction Step 3

Preparation of (E)-4-(1-(4-(1,1,1,3,3,3-hexafluoro-2-hydroxypropan-2-yl)benzyl)indolin-5-yl)but-3-en-2-one, 25

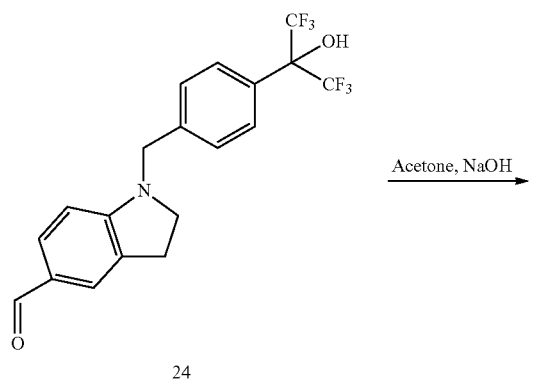

Reaction Step 5

Preparation of 1,1,1,3,3,3-hexafluoro-2-(4-((5-(3-methyl-1H-pyrazol-5-yl)indolin-1-yl)methyl)phenyl)propan-2-ol, 26

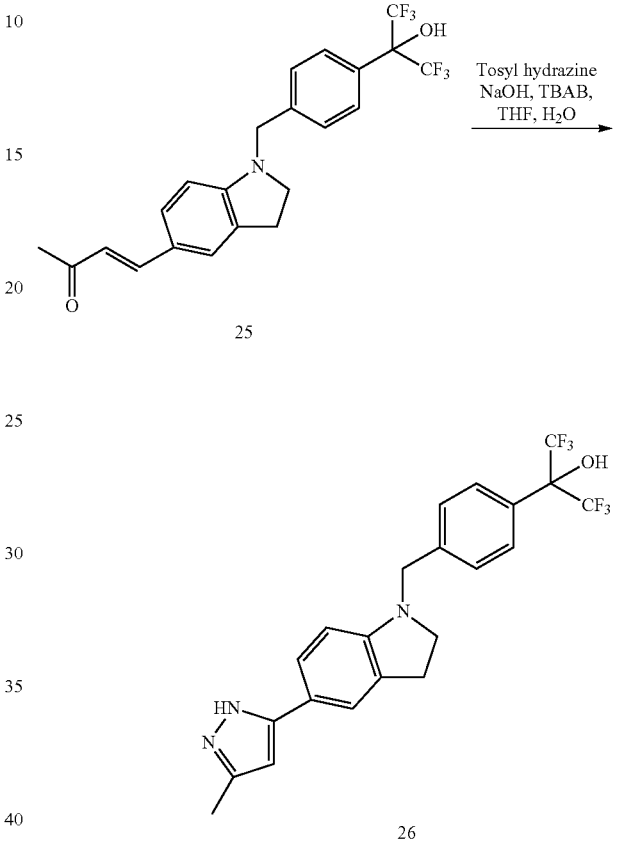

To a stirred solution of 1-(4-(1,1,1,3,3,3-hexafluoro-2-hydroxypropan-2-yl)benzyl)indoline-5-carbaldehyde 24 (0.3 g, 0.74 mmol) in H₂O (10 mL) was added acetone (0.18 mL, 2.2 mmol) dropwise at 0° C. and the mixture was stirred for 10 min. 10% NaOH (4 mL) was added dropwise at 0° C., the mixture was allowed to warm to RT and stir overnight. The progress of the reaction was monitored by TLC (TLC system: 30% EtOAc/Pet ether, $R_f$ value: 0.5).

After completion of the reaction, the reaction mixture was diluted with ethyl acetate, the organic layer was separated, dried over anhydrous sodium sulfate and the solvent was removed under reduced pressure to give (E)-4-(1-(4-(1,1,1,3,3,3-hexafluoro-2-hydroxypropan-2-yl)benzyl)indolin-5-yl)but-3-en-2-one, 25 as a yellow liquid. ¹H NMR (400 MHz, DMSO-d₆) δ: 7.69 (d, 2 H, J=7.6 Hz), 7.46-7.38 (m, 3 H), 7.30 (s, 1 H), 7.23 (s, 1 H), 6.52 (d, 1 H, J=15.6 Hz), 6.42 (d, 1H J=8.0 Hz), 4.35 (s, 2 H), 3.80 (bs, 1 H), 3.52-3.43 (m, 2 H), 3.05 (t, 2 H, J=8.4 Hz), 2.33 (s, 3 H).

A mixture of (E)-4-(1-(4-(1,1,1,3,3,3-hexafluoro-2-hydroxypropan-2-yl)benzyl)indolin-5-yl)but-3-en-2-one, 25 (0.5 g, 1.1 mmol), tosyl hydrazine (0.25 g, 1.3 mmol), TBAB (0.54 g, 1.6 mmol) in THF (50 mL) was added NaOH (0.067 g, 1.6 mmol) in water (4 mL) at RT. The reaction mixture was heated to 100° C. and stirred overnight. The progress of the reaction was monitored by TLC (TLC system: 50% EtOAc/Pet ether, $R_f$ value: 0.45).

After completion of the reaction, the reaction mixture was cooled to RT, diluted with ice cold water and extracted with ethyl acetate (2×80 mL). The combined organic layers were dried over anhydrous sodium sulfate and the solvent was removed under reduced pressure. The crude product was triturated with ethyl acetate (60 mL) to afford 1,1,1,3,3,3-hexafluoro-2-(4-((5-(3-methyl-1H-pyrazol-5-yl)indolin-1-yl)methyl)phenyl)propan-2-ol, 26 as a pale yellow solid. ¹H NMR (DMSO-d₆) δ: 12.20 (br, s, 1 H), 8.66 (s, 1 H), 8.31 (s, 1 H), 7.66 (d, 2 H, J=8.0 Hz), 7.49 (d, 2 H, J=8.4 Hz), 7.37 (br, s, 2 H), 6.58 (br, s, 1 H), 6.22 (s, 1 H), 4.35 (s, 2 H), 3.31 (s, 2 H), 2.95 (t, 2 H, J=8.0 Hz), 2.20 (br, s, 3 H). LC-MS: 99.04% at 215 nm (m/z=456.1, [M+H]⁺).

Example 8

Preparation of 2-(4-((5-(1H-pyrazol-4-yl)indolin-1-yl)methyl)phenyl)-1,1,1,3,3,3-hexafluoropropan-2-ol

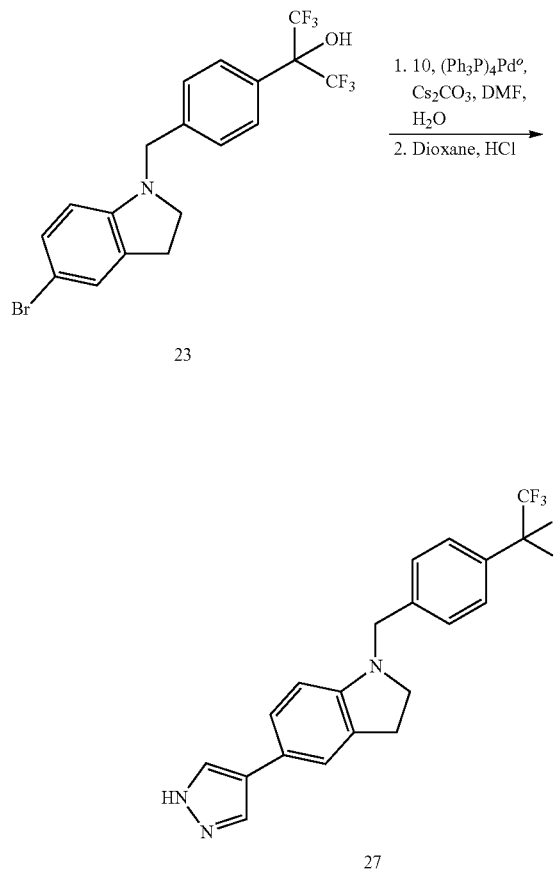

Example 9

Preparation of 1,1,1,3,3,3-hexafluoro-2-(4-((5-(5-methyl-1,3,4-oxadiazol-2-yl)indolin-1-yl)methyl)phenyl)propan-2-ol Reaction Step: 1

Preparation of methyl 1-(4-(1,1,1,3,3,3-hexafluoro-2-hydroxypropan-2-yl)benzyl)indoline-5-carboxylate, 28

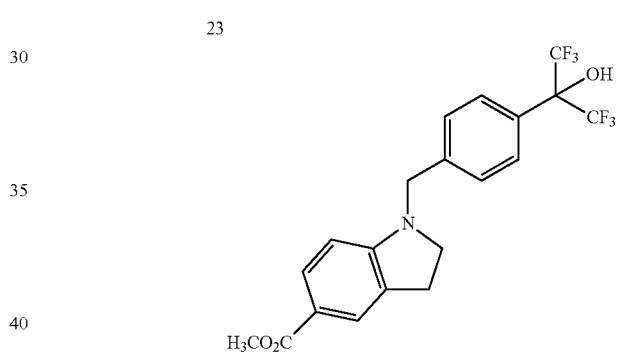

To a stirred solution of 2-(4-((5-bromoindolin-1-yl)methyl)phenyl)-1,1,1,3,3,3-hexafluoropropan-2-ol, 23 (0.4 g, 0.88 mol) and tert-butyl 4-(4,4,5,5-tetramethyl-1,3,2-dioxaborolan-2-yl)-1H-pyrazole-1-carboxylate 10 (0.336 g, 1.2 mmol) in DMF (4 mL) and water (2 mL) was added $Cs_2CO_3$ (0.800 g, 2.5 mmol) the mixture was deoxygenated by the passage of argon for 2 h. $Pd(PPh_3)_4$ (0.098 g, 0.084 mmol) was added and the mixture was heated to 100° C. for 2 h. The progress of the reaction was monitored by TLC (TLC system: 50% EtOAc/Pet ether, $R_f$ value: 0.22).

After completion of the reaction, the reaction mixture was concentrated under reduced pressure, diluted with ethyl acetate and washed with water. The organic layer was dried over anhydrous sodium sulfate and the solvent was removed under reduced pressure. After column purification the product was isolated with 60% purity to afford 2-(4-((5-(1H-pyrazol-4-yl)indolin-1-yl)methyl)phenyl)-1,1,1,3,3,3-hexafluoropropan-2-ol, 27 as a white solid. $^1$H NMR (400 MHz, DMSO-$d_6$) δ: 12.70 (br, s, 1 H), 8.66 (s, 1 H), 7.95 (s, 1 H), 7.74 (s, 1H), 7.66 (d, 2 H, J=8.0 Hz), 7.50 (d, 2 H, J=8.4 Hz), 7.30 (s, 1 H), 7.22 (d, 1 H, J=8.0 Hz), 6.56 (d, 1 H, J=8.0 Hz), 4.32 (s, 2 H), 3.28 (t, 2 H, J=8.0 Hz), 2.95-2.89 (m, 2 H). LC-MS: 96.32% at 215 nm and 86.20% 254 nm (m/z=440.1 [M–H]$^+$). HPLC: 97.58% 284 nm.

To a stirred solution of 2-(4-((5-bromoindolin-1-yl)methyl)phenyl)-1,1,1,3,3,3-hexafluoropropan-2-ol 23 (4.0 g, 8.8 mmol) in MeOH (32 mL) was added $Et_3N$ (3.5 mL, 26 mmol) and the solution was deoxygenated for 15 min. $Pd(dppf)Cl_2$ (0.36 g, 0.44 mmol) was added in steel bomb and the mixture was deoxygenated with nitrogen for 15 min in the autoclave vessel. CO gas was passed through the reaction mixture, the vessel sealed and was heated to 100° C., 150 psi overnight. The progress of the reaction was monitored by TLC (TLC system: 20% EtOAc/Pet ether, $R_f$ value: 0.35).

After completion of the reaction, the reaction mixture was filtered through a celite bed and the eluate extracted with ethyl acetate (2×150 mL). The combined organic layers were dried over anhydrous sodium sulfate and the solvent was removed under reduced pressure. The crude product was purified over silica gel (100-200 mesh) column chromatography eluting with 14% EtOAc/Pet ether to afford methyl 1-(4-(1,1,1,3,3,3-hexafluoro-2-hydroxypropan-2-yl)benzyl)indoline-5-carboxylate, 28 as a light brown liquid. $^1$H NMR (400 MHz, CDCl$_3$) δ: 7.80 (d, 1 H, J=7.2 Hz), 7.73 (s, 1 H), 7.68 (d, 2 H J=8.0 Hz), 7.39 (d, 2 H, J=8.0 Hz), 6.41

(d, 1 H, J=8.4 Hz), 4.40 (s, 2 H), 3.84 (s, 3 H) 3.55-3.48 (m, 2 H), 3.06 (t, 2 H, J=8.8 Hz). LC-MS: 83.99% at (m/z=434.1, [M+H]+).

Reaction Step 2

Preparation of 1-(4-(1,1,1,3,3,3-hexafluoro-2-hydroxypropan-2-yl)benzyl)indoline-5-carboxylic acid, 29

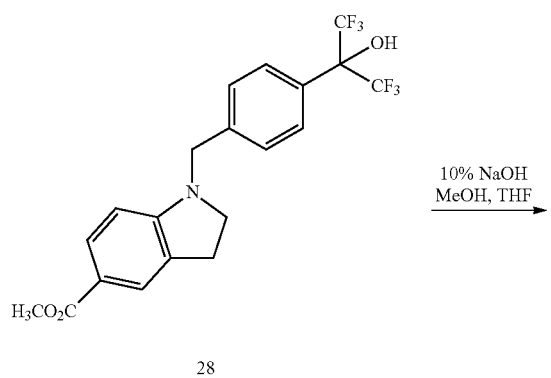

Reaction Step 3

Preparation of N'-acetyl-1-(4-(1,1,1,3,3,3-hexafluoro-2-hydroxypropan-2-yl)benzyl)indoline-5-carbohydrazide, 30

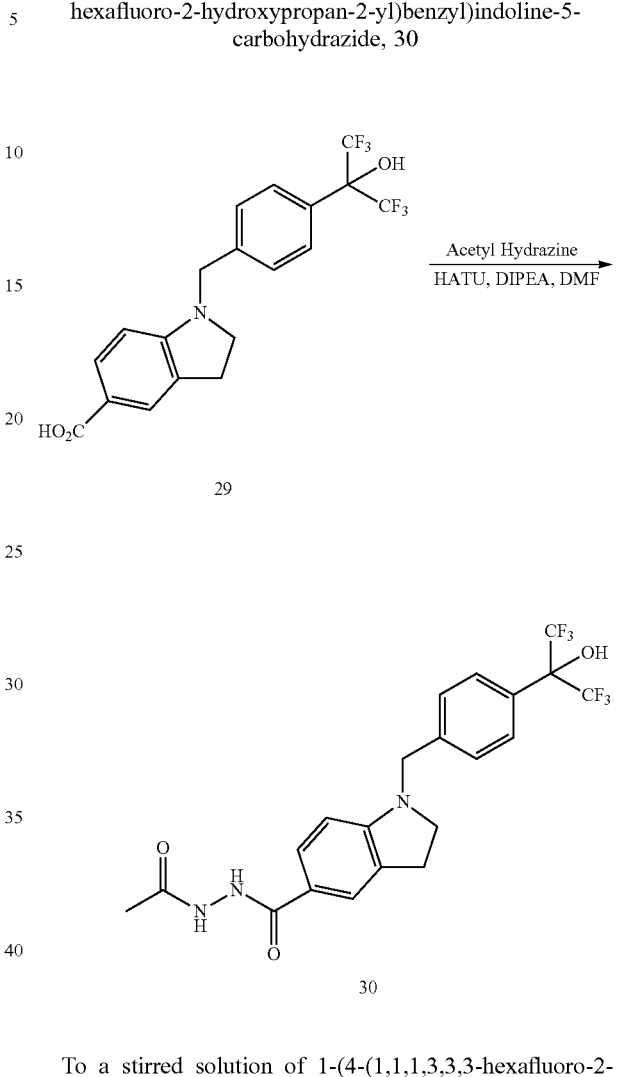

To a stirred solution of methyl 1-(4-(1,1,1,3,3,3-hexafluoro-2-hydroxypropan-2-yl)benzyl)indoline-5-carboxylate, 28 (1.0 g, 2.3 mmol) in THF (5.0 mL) and methanol (5.0 mL) was added 10% NaOH (3 mL) at RT. The resulting reaction mixture was heated to 70° C. for 2 h. The progress of the reaction was monitored by TLC (TLC system: 80% EtOAc/Pet ether, R$_f$ value: 0.2)

After completion of reaction, the reaction mixture was evaporated under reduced pressure, the residue was diluted with cold water, acidified to pH 2 with 2N HCl solution and extracted with ethyl acetate (2×50 mL). The combined organic layers were washed with water and brine solution, dried over anhydrous sodium sulfate and the solvent was removed under reduced pressure to give 1-(4-(1,1,1,3,3,3-hexafluoro-2-hydroxypropan-2-yl)benzyl)indoline-5-carboxylic acid as an off white solid.

To a stirred solution of 1-(4-(1,1,1,3,3,3-hexafluoro-2-hydroxypropan-2-yl)benzyl)indoline-5-carboxylic acid, 29 (0.2 g, 0.4 mmol) in DMF (4 mL) was added acetyl hydrazine (0.103 g, 1.4 mmol), HATU (0.27 g, 0.7 mmol) at 0° C. and the mixture was stirred for 20 min. DIPEA (0.314 g, 2.0 mmol) was added dropwise and the mixture allowed warm to RT and stir overnight. The progress of the reaction was monitored by TLC (TLC system: 100% EtOAc (UV & KMnO$_4$), R$_f$ value: 0.01).

After completion of reaction, the reaction mixture was diluted with water and extracted with ethyl acetate (4×50 mL). The organic layer was dried over sodium sulfate and evaporated under reduced pressure. The crude product was purified over silica gel (100-200 mesh) column chromatography by eluting with 80% ethyl acetate/pet ether to afford N-acetyl-1-(4-(1,1,1,3,3,3-hexafluoro-2-hydroxypropan-2-yl)benzyl)indoline-5-carbohydrazide, 30 as a colorless liquid. $^1$H NMR (400 MHz, DMSO-d$_6$) δ: 10.80 (s, 1 H), 9.83 (s, 1 H), 9.721 (s, 1 H), 8.70 (s, 1 H), 7.66 (d, 2 H, J=8.4 Hz), 7.60 (d, 2 H, J=8.4 Hz), 7.46 (d, 1 H, J=4.8 Hz), 7.29 (dd, 1 H, J$_1$=10.8, J$_2$=5.2 Hz), 6.60 (dd, 1 H, J$_1$=8.4, J$_2$=4.0 Hz), 4.45 (s, 2 H), 3.42-3.34 (m, 3.0 Hz), 2.97-2.89 (m, 2 H), 2.78-2.68 (m, 2 H), 2.50-2.20 (m, 2 H).

Reaction Step 4

Preparation of 1,1,1,3,3,3-hexafluoro-2-(4-((5-(5-methyl-1,3,4-oxadiazol-2-yl)indolin-1-yl)methyl)phenyl)propan-2-ol, 31

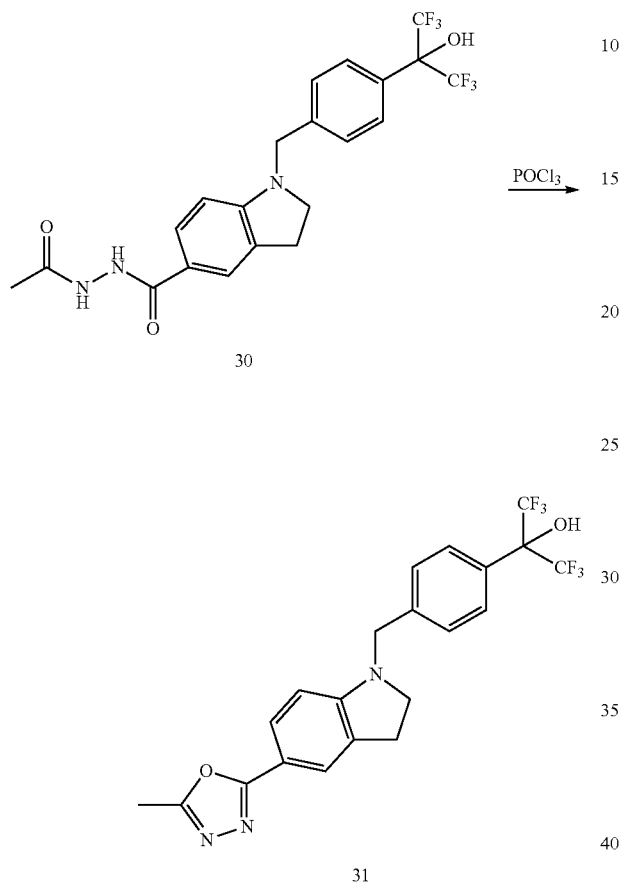

A mixture of N'-acetyl-1-(4-(1,1,1,3,3,3-hexafluoro-2-hydroxypropan-2-yl)benzyl)indoline-5-carbohydrazide, 30 (0.180 g, 0.37 mmol) and POCl$_3$ (4 mL) was heated to 130° C. for 6 h. The progress of the reaction was monitored by TLC (TLC system: 70% EtOAc/Pet ether, R$_f$ value: 0.4)

After completion of the reaction, the reaction mixture was evaporated under reduced pressure. The crude product was washed with saturated NaHCO$_3$ and extracted with ethyl acetate (3×80 mL). The combined organic layers were dried over anhydrous sodium sulfate and the solvent was removed under reduced pressure to afford the crude product. The crude product was purified by prep HPLC to afford 1,1,1,3,3,3-hexafluoro-2-(4-((5-(5-methyl-1,3,4-oxadiazol-2-yl)indolin-1-yl)methyl)phenyl)propan-2-ol, 31 as an off-while solid. $^1$H NMR (400 MHz, DMSO-d$_6$) δ: 8.70 (br, s, 1 H), 7.67 (d, 2 H, J=8.0 Hz), 7.60 (d, 2 H, J=6.8 Hz), 7.47 (d, 2 H, J=8.4 Hz), 6.68 (t, 1 H, J=6.0 Hz), 4.48 (s, 2 H), 3.49 (t, 2 H, J=8.4 Hz), 3.04 (t, 2 H, J=8.0 Hz), 2.5 (s, 3 H). LC-MS: 99.60% at 215 nm (m/z=458.1 [M+H]$^+$).

Example 10

Preparation of 4-((5-(1H-pyrazol-4-yl)indolin-1-yl)methyl)benzamide

Step 1

Preparation of methyl 4-((5-bromoindolin-1-yl)methyl)benzoate, 32

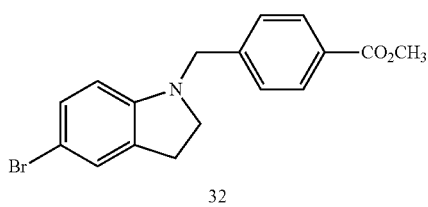

Methyl 4-((5-bromoindolin-1-yl)methyl)benzoate can be prepared by alkylation of 5-bromoindoline with methyl (4-bromomethyl)benzoate in the presence of NaH in THF using the general procedure described in Example 7, step 1.

Step 2

Preparation of 4-((5-bromoindolin-1-yl)methyl)benzamide, 33

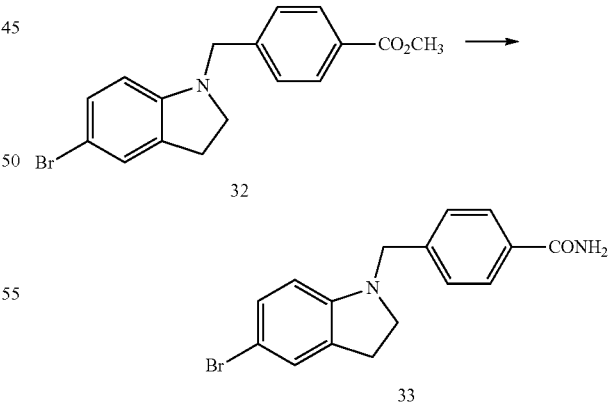

4-((5-bromoindolin-1-yl)methyl)benzamide, 33 can be prepared by hydrolysis of the methyl ester of 32 by treatment with NaOH in EtOH until hydrolysis is complete followed by activation of the resulting acid with isobutyl chloroformate in the presence of NMP in THF at −50° C. for 30 min and the gradual introduction of a solution of NH$_3$ in THR.

Step 3

Preparation of 4-((5-(1H-pyrazol-4-yl)indolin-1-yl)methyl)benzamide, 34

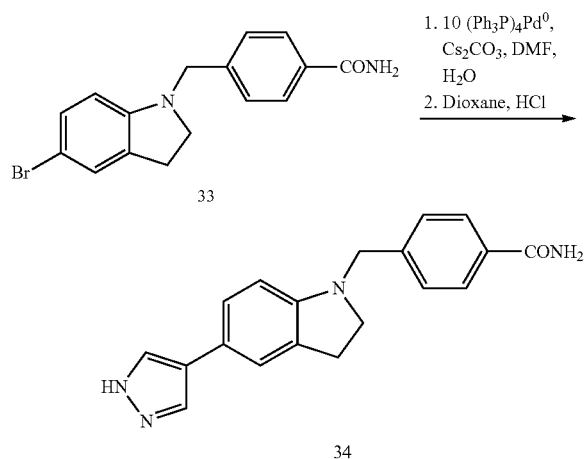

4-((5-(1H-pyrazol-4-yl)indolin-1-yl)methyl)benzamide, 34 can be prepared by deoxygenation of a solution of 4-((5-bromoindolin-1-yl)methyl)benzamide, 33, tert-butyl 4-(4,4,5,5-tetramethyl-1,3,2-dioxaborolan-2-yl)-1H-pyrazole-1-carboxylate, 10 and $Cs_2CO_3$ in DMF:water 2:1 by the passage of argon for 20 min followed by the introduction of $Pd(PPh_3)_4$ and heating the mixture to 100° C. for 2 h. Treatment of the crude product with HCl in dioxane then can provide 4-((5-(1H-pyrazol-4-yl)indolin-1-yl)methyl)benzamide, 34.

Example 11

Preparation of 4-((5-(1H-pyrazol-4-yl)indolin-1-yl)methyl)-N-methylbenzamide

Preparation of methyl 4-((5-bromoindolin-1-yl)methyl)benzoate, 32

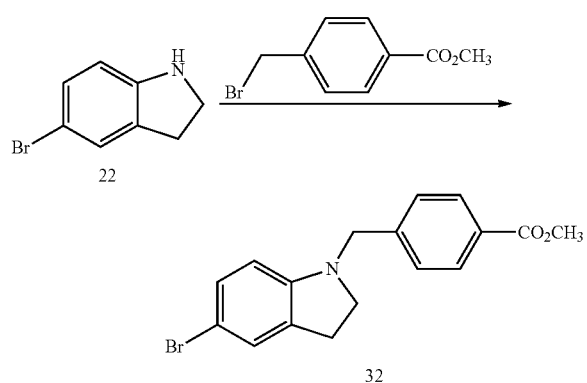

Methyl 4-((5-bromoindolin-1-yl)methyl)benzoate can be prepared by alkylation of 5-bromoindoline with methyl (4-bromomethyl)benzoate in the presence of NaH in THF using the general procedure described in Example 7, step 1.

Step 2

Preparation of 4-((5-bromoindolin-1-yl)methyl)-N-methylbenzamide, 35

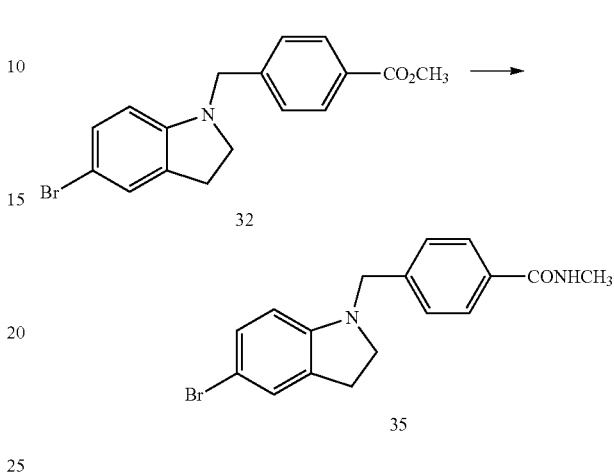

4-((5-bromoindolin-1-yl)methyl)-N-methylbenzamide, 35 can be prepared by hydrolysis of the methyl ester of 32 by treatment with NaOH in EtOH until hydrolysis is complete followed by treating a DMF solution of resulting acid with $CH_3NH_2 \cdot HCl$ and HATU with DIPEA at 0° C. and allowing the mixture to stir over night at room temperature.

Step 3

Preparation of 4-((5-(1H-pyrazol-4-yl)indolin-1-yl)methyl)-N-methylbenzamide, 36

4-((5-(1H-pyrazol-4-yl)indolin-1-yl)methyl)benzamide, 36 can be prepared by deoxygenation of a solution of 4((5-bromoindolin-1-yl)methyl)-N-methylbenzamide, 35, tert-butyl 4-(4,4,5,5-tetramethyl-1,3,2-dioxaborolan-2-yl)-1H-pyrazole-1-carboxylate, 10 and $Cs_2CO_3$ in DMF:water 2:1 by the passage of argon for 20 min followed by the introduction of $Pd(PPh_3)_4$ and heating the mixture to 100° C. for 2 h. Treatment of the crude product with HCl in dioxane then can provide 4-((5-(1H-pyrazol-4-yl)indolin-1-yl)methyl)-N-methylbenzamide, 36.

Example 12

Synthesis of N-(1-(4-(1-hydroxycyclobutyl)benzyl)indolin-5-yl), 42

Reaction Step 1

Preparation of 1-(p-tolyl)cyclobutanol, 39

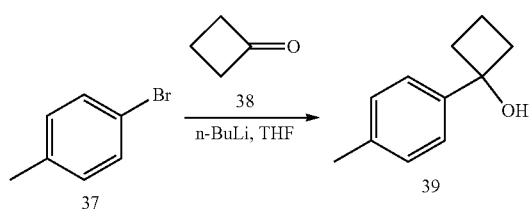

To a stirred solution of 4-bromotoluene, 37 (5.0 g, 29 mmol) in THF (70 mL) was added 2.5 M n-BuLi (17 mL, 35 mmol) dropwise at −75° C. and the reaction mixture was stirred for 30 min. Cyclobutanone, 38 (2.6 mL, 35 mmol) was added at the same temperature and the reaction mixture was stirred for 1 h. The progress of the reaction was monitored by TLC (TLC system: 10% EtOAc/Pet ether, $R_f$ value: 0.25)

After completion of the reaction, the reaction mixture was quenched with saturated ammonium chloride solution at −70° C. and diluted with water. The aqueous solution was extracted with ethyl acetate (2×150 mL). The combined organic layers were dried over anhydrous sodium sulphate and evaporated under reduced pressure. The crude product was purified over silica gel (100-200 mesh) column chromatography eluting with 5% EtOAc/Pet ether to give 1-(p-tolyl)cyclobutanol, 39 as a colorless liquid.

Reaction Step 2

Preparation of 1-(4-(bromomethyl)phenyl)cyclobutanol, 40

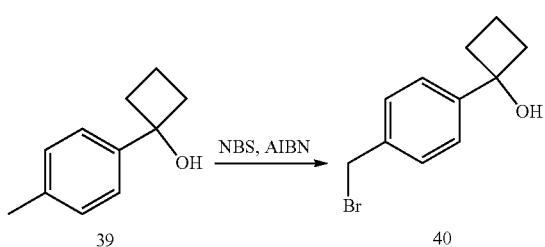

To stirred solution of 1-(p-tolyl)cyclobutanol, 39 (3.0 g, 18 mmol) in $CCl_4$ (50 mL) was added NBS (3.2 g, 18 mmol) and AIBN (0.03 g, 0.18 mmol) at RT. The resulting reaction mixture was heated to reflux overnight. The progress of the reaction was monitored by TLC (TLC system: 10% EtOAc/Pet ether, $R_f$ value: 0.2)

After completion of the reaction, the reaction mixture was cooled, poured into ice cold water and extracted with dichloromethane (2×200 mL). The combined organic layers were dried over anhydrous sodium sulfate and the solvent was evaporated under reduced pressure. The crude product was purified over silica gel (100-200 mesh) column chromatography eluting with 7% EtOAc/Pet ether to give 1-(4-(bromomethyl)phenyl)cyclobutanol, 40 as a colorless liquid.

Step 3

Preparation of 1-(4-((5-bromoindolin-1-yl)methyl)phenyl)cyclobutanol, 41 1-(4-(bromomethyl)phenyl)cyclobutanol

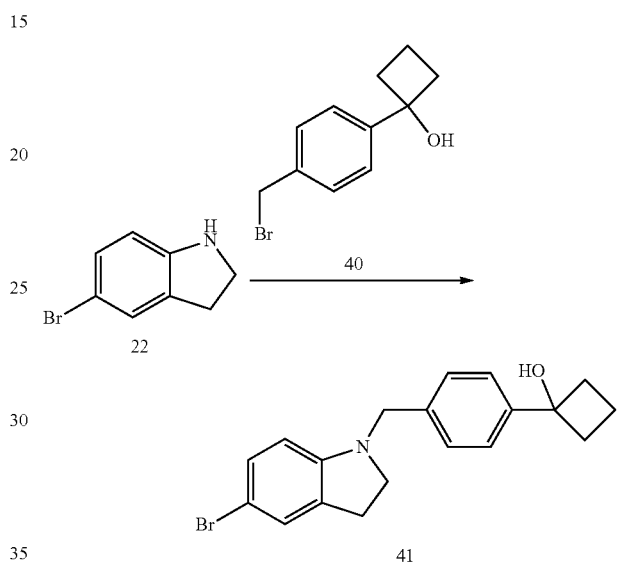

1-(4-((5-bromoindolin-1-yl)methyl)phenyl)cyclobutanol, 41 can be prepared by the alkylation of 5-bromo indoline with 1-(4-(bromomethyl)phenyl)cyclobutanol, 40 in the presence of NaH in THF using the procedure described in Example 7, step 1.

Step 4

Preparation of 1-(4-((5-(1H-pyrazol-4-yl)indolin-1-yl)methyl)phenyl)cyclobutanol, 42

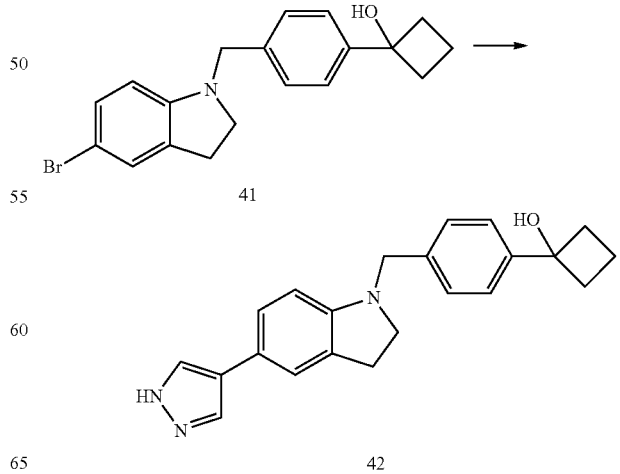

1-(4-((5-(1H-pyrazol-4-yl)indolin-1-yl)methyl)phenyl) cyclobutanol, 42 can be prepared by coupling of 1-(4-((5-bromoindolin-1-yl)methyl)phenyl)cyclobutanol, 41 with tert-butyl 4-(4,4,5,5-tetramethyl-1,3,2-dioxaborolan-2-yl)-1H-pyrazole-1-carboxylate, 10 followed by deprotection by treatment with HCl in dioxane using the general procedure described in Example 8.

Example 13

Preparation of 5-(1H-pyrazol-4-yl)-1-(4-(1,1,1-trifluoro-2-methylpropan-2-yl)benzyl)indoline Preparation of (4-(1,1,1-trifluoro-2-methylpropan-2-yl)phenyl)methanol, 44

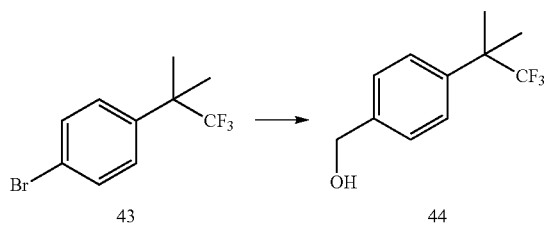

(4-(1,1,1-Trifluoro-2-methylpropan-2-yl)phenyl)methanol, 44 can be prepared from 1-bromo-4-(1,1,1-trifluoro-2-methylpropan-2-yl)benzene, 43 by palladium catalyzed carbonylation by deoxygenating a solution of 1-bromo-4-(1,1,1-trifluoro-2-methylpropan-2-yl)benzene, 43, and an excess of Et₃N in MeOH DMF 2:1 by the passage of argon for 20 min contained in an autoclave vessel. Pd(PPh₃)₄ can be added and the mixture further deoxygenated with argon for 20 min. Passage of CO gas through the reaction mixture, and adjustment of the CO pressure to 150 psi prior to heating to 100° C. overnight can then lead to methyl 4-(1,1,1-trifluoro-2-methylpropan-2-yl)benzoate, which can be treated with LAH in THF solution to afford, after an aqueous workup, (4-(1,1,1-trifluoro-2-methylpropan-2-yl)phenyl)methanol, 44.

Step 2

Preparation of 1-bromo-4-(1,1,1-trifluoro-2-methylpropan-2-yl)benzene, 45

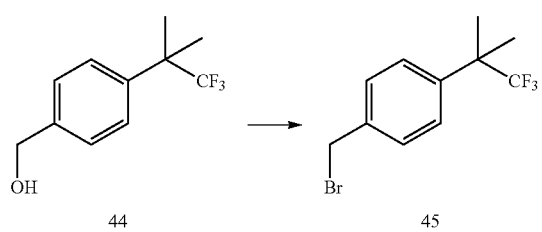

1-Bromo-4-(1,1,1-trifluoro-2-methylpropan-2-yl)benzene, 45 can be prepared by treatment of a solution of (4-(1,1,1-trifluoro-2-methylpropan-2-yl)phenyl)methanol, 44, in ether with PBr₃ at room temperature for 4 h, followed by quenching and aqueous workup.

Step 3

Preparation of 5-bromo-1-(4-(1,1,1-trifluoro-2-methylpropan-2-yl)benzyl)indoline, 46

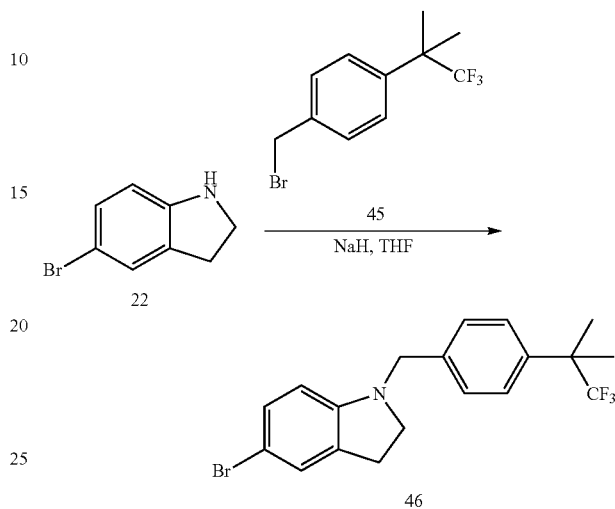

5-Bromo-1-(4-(1,1,1-trifluoro-2-methylpropan-2-yl)benzyl)indoline, 46 can be prepared from 5-bromoindoline, 22 and 1-bromo-4-(1,1,1-trifluoro-2-methylpropan-2-yl)benzene, 45 using the general method described in Example 7, step 1.

Step 4

Preparation of 5-(1H-pyrazol-4-yl)-1-(4-(1,1,1-trifluoro-2-methylpropan-2-yl)benzyl)indoline, 47

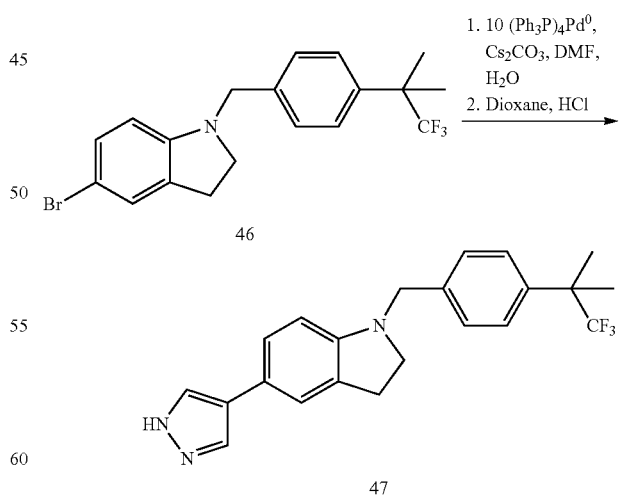

5-(1H-Pyrazol-4-yl)-1-(4-(1,1,1-trifluoro-2-methylpropan-2-yl)benzyl)indoline, 47 can be prepared from 5-bromo-1-(4-(1,1,1-trifluoro-2-methylpropan-2-yl)benzyl)indoline, 46 using the general method described in Example 8.

Example 14

Preparation of 5-(1H-pyrazol-4-yl)-1-(4-(trifluoromethyl)benzyl)indoline

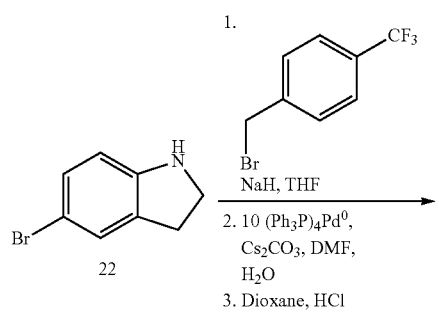

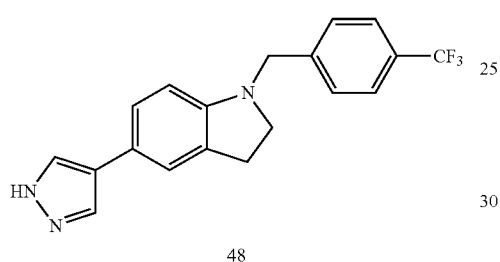

48

5-(1H-Pyrazol-4-yl)-1-(4-(trifluoromethyl)benzyl)indoline, 48 can be prepared by alkylation of 5-bromoindoline, 22 with 1-bromomethyl-4-trifluoromethylbenzene using the conditions described in Example 7, part 1 followed by palladium catalyzed coupling of the alkylation product with tert-butyl 4-(4,4,5,5-tetramethyl-1,3,2-dioxaborolan-2-yl)-1H-pyrazole-1-carboxylate, 10 followed by hydrolysis using the reaction conditions described in Example 8

Example 15

Preparation of 1-(4-isopropylbenzyl)-5-(1H-pyrazol-4-yl)indoline

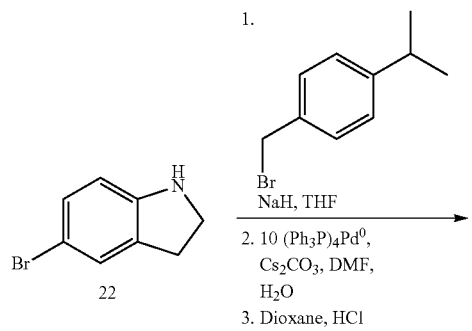

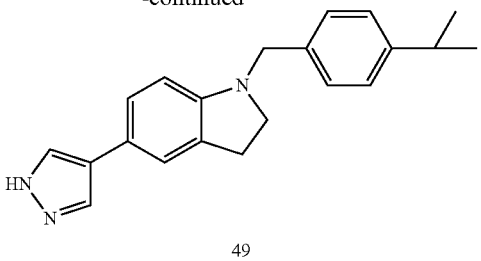

49

1-(4-Isopropylbenzyl)-5-(1H-pyrazol-4-yl)indoline, 49 can be prepared by alkylation of 5-bromoindoline, 22 with 1-bromomethyl-4-isopropylbenzene using the conditions described in Example 7, part 1 followed by palladium catalyzed coupling of the alkylation product with tert-butyl 4-(4,4,5,5-tetramethyl-1,3,2-dioxaborolan-2-yl)-1H-pyrazole-1-carboxylate, 10 followed by hydrolysis using the reaction conditions described in Example 8.

Example 16

1-(4-(tert-butyl)benzyl)-5-(1H-pyrazol-4-yl)indoline, 50

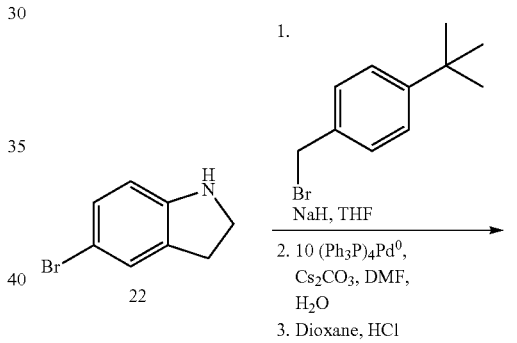

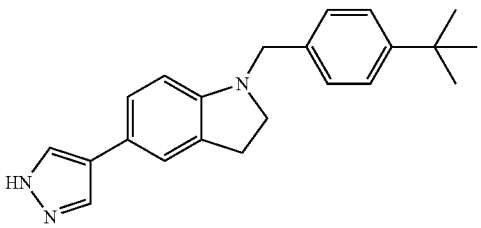

50

1-(4-Isopropylbenzyl)-5-(1H-pyrazol-4-yl)indoline, 50 can be prepared by alkylation of 5-bromoindoline, 22 with 1-(bromomethyl)-4-(tert-butyl)benzene using the conditions described in Example 7, part 1 followed by palladium catalyzed coupling of the alkylation product with tert-butyl 4-(4,4,5,5-tetramethyl-1,3,2-dioxaborolan-2-yl)-1H-pyrazole-1-carboxylate, 10 followed by hydrolysis using the reaction conditions described in Example 8.

Example 17

Preparation of 2-(4-((5-(1H-pyrazol-4-yl)indolin-1-yl)methyl)phenyl)-1,1,1,3,3,3-hexafluoropropan-2-ol

Step 1

Preparation of 5-bromoindoline, 29

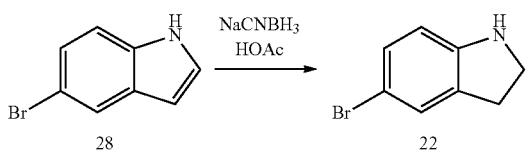 [SMILES: Brc1ccc2[nH]ccc2c1 ; Brc1ccc2c(c1)CCN2]

NaCNBH₃ (213.2 g, 3.38 mol) was added portion wise to a stirred solution of 5-bromoindole (200.0 g, 1.03 mol) in acetic acid (2.0 L) at 10° C. and the mixture was stirred for 2 h. The progress of the reaction was monitored by TLC (TLC system: 20% EtOAc/pet ether, $R_f$ value: 0.4).

After completion of the reaction, the reaction mixture was evaporated under reduced pressure. The crude product was basified with 10% NaOH solution and extracted with ethyl acetate (2×1.0 L). The combined organic layers were dried over sodium sulfate and evaporated under reduced pressure. The crude compound was purified over silica gel (100-200 mesh) column chromatography by eluting with 10% EtOAc/Pet ether to afford 5-bromoindoline, 22 as a thick yellow liquid. ¹H NMR (400 MHz, CDCl₃) δ: 7.18 (s, 1 H), 7.08 (d, J=8.0 Hz, 1H), 6.48 (d, J=8.4 Hz, 1 H), 3.55 (t, J=8.4 Hz, 2 H), 3.01 (t, J=8.4 Hz, 2 H). LC-MS: 96.26% (m/z=198.1, [M+H]⁺).

Step 2

Preparation of 2-(4-((5-bromoindolin-1-yl)methyl)phenyl)-1,1,1,3,3,3-hexafluoropropan-2-ol, 23

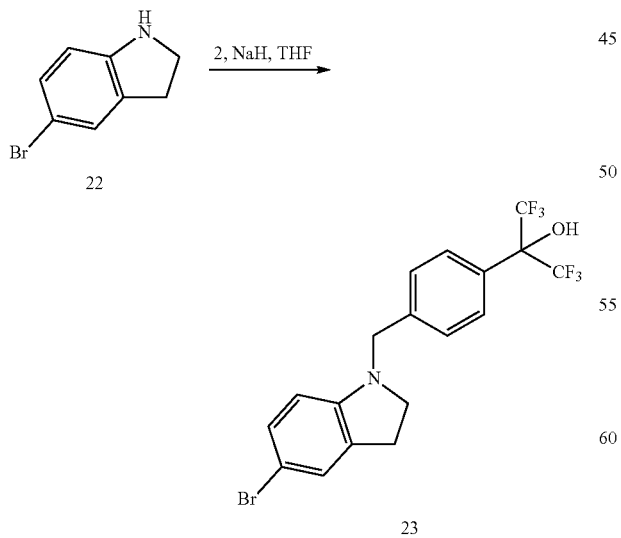

60% NaH (60.0 g, 1.52 mol) was added portion wise to a stirred solution of 2-(4-(bromomethyl)phenyl)-1,1,1,3,3,3-hexafluoropropan-2-ol (221.7 g, 1.3 mol) and 2-bromoindoline (100.0 g, 0.507 mol) in THF (1.0 L) at 0° C. The resulting reaction mixture was heated to 80° C. for 3 h. The progress of the reaction was monitored by TLC (TLC system: 30% EtOAc/Pet ether, $R_f$ value: 0.65).

The reaction mixture was quenched with ice cold water and extracted with ethyl acetate (2×1.0 L). The combined organic layers were washed with water and brine. The organic layer was dried over anhydrous sodium sulfate and the solvent was removed under reduced pressure. The crude compound was purified over silica gel (230-400 mesh) column chromatography eluting with 5% EtOAc/Pet ether to afford 2-(4-((5-bromoindolin-1-yl)methyl)phenyl)-1,1,1,3,3,3-hexafluoropropan-2-ol, 23 as a thick yellow liquid. ¹H NMR (400 MHz, CDCl₃) δ: 7.67 (d, J=8.0 Hz, 2H), 7.42 (d, J=8.0 Hz, 2H), 7.17 (s, 1H), 7.12 (d, J=8.4 Hz, 1H), 6.31 (d, J=8.0 Hz, 1H), 4.25 (s, 2H), 3.35 (t, J=8.0 Hz, 2H), 2.98 (t, J=8.0 Hz, 2H); LC-MS: 99.28% (m/z=454.1, [M+H]⁺).

Step 3

Preparation of 2-(4-((5-bromoindolin-1-yl)methyl)phenyl)-1,1,1,3,3,3-hexafluoropropan-2-ol, 23

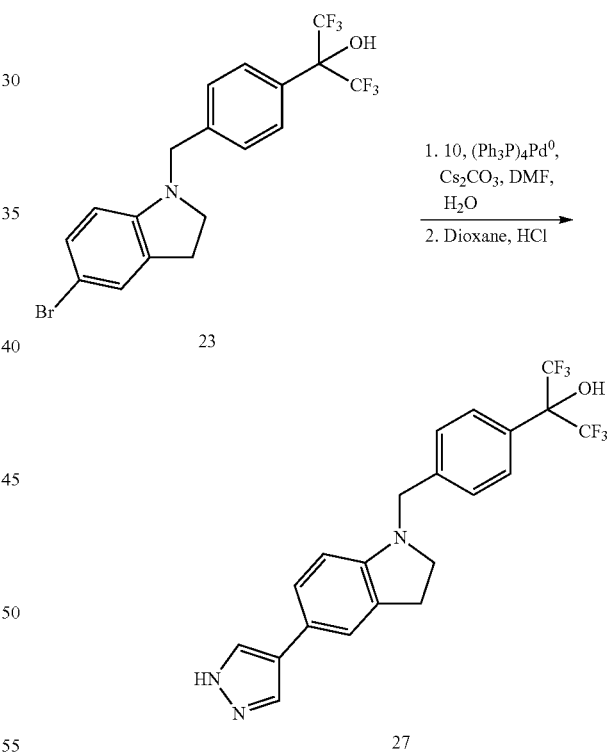

To a stirred solution of 2-(4-((5-bromoindolin-1-yl)methyl)phenyl)-1,1,1,3,3,3-hexafluoropropan-2-ol, 23 (25.0 g, 55.2 mmol) and tert-butyl 4-(4,4,5,5-tetramethyl-1,3,2-dioxaborolan-2-yl)-1H-pyrazole-1-carboxylate 10 (21.08 g, 71.7 mmol) in DMF (250 mL) and water (75 mL) was added Cs₂CO₃ (53.9 g, 166 mmol) under a nitrogen atmosphere. The reaction mixture was de-oxygenated by purging argon gas into the reaction mixture for 30 min. PdCl₂(dppf). dichloromethane (4.5 g, 5.5 mmol) was added to the reaction mixture and the mixture was heated to 100° C. overnight.

The progress of the reaction was monitored by TLC (TLC system: 40% EtOAc/Pet ether, $R_f$ value: 0.01).

After completion of the reaction, the reaction mixture was filtered through a celite bed. The filtrate was extracted with ethyl acetate (2×500 mL). The combined organic layers were washed with brine and dried over anhydrous sodium sulfate. The solvent was removed under reduced pressure to afford crude compound. This procedure was repeated on an additional 3×25 g batches and the crude products were combined for purification. The combined crude product was purified by chromatography over neutral alumina eluting with 50% EtOAc/Pet ether to afford 2-(4-((5-(1H-pyrazol-4-yl)indolin-1-yl)methyl)phenyl)-1,1,1,3,3,3-hexafluoro-propan-2-ol, 27, mp 191-195° C. after crystallization from hot ethyl acetate and diethyl ether. $^1$H NMR (400 MHz, CDCl$_3$) δ: 12.68 (bs, 1H), 8.63 (s, 1H), 7.95 (s, 1H), 7.66 (d, J=8.0 Hz, 2H), 7.50 (d, J=8.8 Hz, 2H), 7.29 (s, 1H), 7.21 (dd, $J_1$=8.0 Hz, $J_2$=1.6 Hz, 1H), 6.55 (d, J=8.0 Hz, 1H), 4.32 (s, 2H), 3.30 (t, J=8.4 Hz, 2H), 2.93 (t, J=8.4 Hz, 2H). LC-MS: 98.05% at 215 nm and 92.29% at 254 nm (m/z=441.8, [M+H]$^+$).

Biological Examples

The compounds according to Formula 1 are RORα and/or RORγ modulators, and are useful in the treatment of RORα- and/or RORγ-regulated diseases. The biological activities of the compounds according to Formula 1 can be determined using any suitable assay for determining the activity of a candidate compound as a RORα and/or RORγ modulator, as well as in tissue and in vivo models.

Example 18

TH17 Cell Differentiation

Peripheral blood mononuclear cells (PBMCs) were sourced from freshly prepared leukocyte enriched plasma (buffy coat) from healthy volunteers from which PBMCs were isolated by density gradient centrifugation using Ficoll-Paque™ PLUS (GE Healthcare). Naïve CD4+ T cells were isolated using the Naïve CD4+ T cell Isolation Kit II (Miltenyi Biotec) as per manufacturer's instructions. CD4+ T cells were plated at 5×10$^4$ cells/well in 96 well plates pre-coated with immobilized human (h)-αCD3 antibody (eBioscience) then differentiated to $T_H17$ cells using h-αCD28, h-αIFN-γ, h-αIL-4, h-IL-6, h-IL-23, h-IL-1β, h-TGF-β1 (eBioscience) and maintained in a cell culture incubator at 37° C. with 5% CO$_2$ in TexMACS Medium (Miltenyi Biotec) supplemented with 1% Penicillin/Streptomycin (Lonza) over 5 days.

Example 19

TH17 Cytokine Inhibition as Measured by ELISA

Human CD4+ T cells were differentiated to $T_H17$ cells as described in the presence or absence of various concentrations of compounds in a final concentration of 0.1% DMSO in TexMACS medium. Supernatants were collected and stored at −20° C. until they were to be assayed for IL-17A, IL-17F, IL-17AF, IL-21 and/or IL-22 levels as determined by Ready-Set-Go ELISA kits (eBioscience) as per manufacturer's instructions. Endpoint absorbance was read at 450 nm and 570 nm according to manufacturer's instructions (eBioscience) using a microplate reader (Perkin Elmer). The percentage of cytokine inhibition was calculated with reference to DMSO treated cells and the IC$_{50}$s were determined by GraphPad Prism software and presented in the table below.

| Compound from Example | IL-17A IC$_{50}$ [uM] | IL-17F IC$_{50}$ [uM] | IL-17AF IC$_{50}$ [uM] | IL-22 IC$_{50}$ [uM] | IL-21 IC$_{50}$ [uM] |
|---|---|---|---|---|---|
| 1 | <10 | <10 | <10 | <10 | <10 |
| 2 | <10 | <10 | <10 | <10 | <10 |
| 3 | <10 | <10 | <10 | <10 | <10 |
| 4 | <10 | <10 |  | <10 |  |
| 5 | <10 | <10 | <10 | <10 | <10 |
| 6 | <10 | >10 |  | <10 |  |
| 7 | <10 | <10 | <10 | <10 | <10 |
| 8 | <10 | <10 | <10 | <10 | <10 |
| 9 | <10 | <10 | >10 | <10 | <10 |

Example 20

TH17 Cell Viability and Proliferation

Cells were assayed for viability in the presence or absence of 1 μM compound using Prestoblue® Cell Viability Reagent (Life Technologies) as per manufacturer's instructions after 30 minutes incubation of $T_H17$ cells with reagent. Absorbance was measured at 570 nm and 600 nm using a microplate reader (Perkin Elmer) and data were analyzed as per manufacturer's instructions. Cell viability was determined after 5 days and expressed as a percentage of DMSO treated cells. The percentage (%) cell viability of compound treated $T_H17$ cells are presented in the table below.

| Compound from Example | % viability of compound treated $T_H17$ cells |
|---|---|
| 1 | >80 |
| 2 | >80 |
| 3 | >80 |
| 4 | >80 |
| 5 | <80 |
| 6 | >80 |
| 7 | >80 |
| 8 | >80 |
| 9 | >80 |

Cellular proliferation was assessed in the presence or absence of 3 μM compound using Prestoblue® Cell Viability Reagent (Life Technologies) as per manufacturer's instructions using absorbance as the output measured by a microplate reader (Perkin Elmer) after 30 minutes of incubation. A standard curve developed by plotting varying cell numbers versus absorbance was used to assess differences in cellular proliferation between compound treated or untreated cells after the 5 day $T_H17$ differentiation period. Percentage (%) change in $T_H17$ cell number in the presence of compound are presented in the table below.

| Compound from Example | % change in $T_H17$ cell number |
|---|---|
| 1 | A |
| 2 | A |
| 3 | A |
| 4 | B |
| 5 | B |
| 6 | B |
| 7 | A |

-continued

| Compound from Example | % change in $T_H17$ cell number |
|---|---|
| 8 | A |
| 9 | A |

A: >50% decrease in cell proliferation relative to DMSO treated $T_H17$ cells
B: ≤50% decrease in cell proliferation relative to DMSO treated $T_H17$ cells Example 21

Real Time quantitative Reverse Transcription PCR
(Real-Time qRT-PCR)

RNA was isolated from $T_H17$ cells and cDNA was synthesized using the Verso cDNA kit (Thermo Scientific) as per manufacturer's instructions. IL-17A, IL-17F, IL-21, IL-22, G-CSF, IL-23R and FOXP3 gene expression were determined for compound treated and untreated $T_H17$ cell samples using Solaris qPCR Gene expression assays (Thermo Scientific) with an iCycler iQ Real-Time PCR Detection System (Bio-Rad). Individual gene expression was normalized to a panel of six reference genes (ACTB, TBP, HPRT1, PGK1, TFRC and PPIA) (Thermo Scientific) and analyzed by REST 2009 (Qiagen) in accordance to MIQE guidelines (Bustin et al. (2009) *Clin. Chem,* 55:611-622). The effects of compounds on $T_H17$ cytokine gene expression are presented as fold change in mRNA levels of compound treated $T_H17$ cells relative to DMSO treated cells in the table below.

| Compound from | Fold change in mRNA levels of compound treated $T_H17$ cells relative to DMSO treated cells | | | | | |
|---|---|---|---|---|---|---|
| Example | IL-17A | IL-17F | IL-22 | IL-21 | IL-23R | FOXP3 |
| 1 | A | B | B | B | A | C |
| 2 | B | B | B | B | A | C |
| 3 | B | B | B | B | A | A |
| 4 | B | B | B | B | A | A |
| 5 | A | A | A | A | A | A |
| 6 | B | B | B | A | C | C |

A: No change in gene expression observed relative to DMSO treated Th17 cells
B: Decreased gene expression observed relative to DMSO treated Th17 cells
C: Increased gene expression observed relative to DMSO treated Th17 cells Example 22

RORγ LBD Binding

Compound binding to the human RORγ LBD was assessed using the Human RORγ Assay System (INDIGO Biosciences Inc.) as per manufacturer's instructions. Binding to the RORγ LBD was assessed using gradient concentrations of the indicated compounds in a final concentration of 0.5% DMSO, where $IC_{50}$s were generated using Graphpad Prism and presented in the table below.

| Compound from Example | RORγ LBD Binding $IC_{50}$ [μM] |
|---|---|
| 1 | >10 |
| 2 | >10 |
| 3 | >10 |
| 4 | <10 |
| 5 | >10 |
| 6 | >10 |

Example 23

Co-Activator and Co-Repressor Protein Interaction
with Human ROR and RORα LBDs

The Time-Resolved Fluorescence Resonance Energy Transfer (TR-FRET) assay kit (Life Technologies) was used to measure compound efficacy to disrupt or enhance ligand-mediated interaction of the co-activator and co-repressor peptides with the purified GST-tagged (i) RORγ LBD or (ii) RORα LBD. The RORγ LBD and RORα LBD each have a basal level of interaction with the co-activator D22 or co-repressor NCoR1-D2 in the absence of ligand, thus it is possible to identify compounds that inhibit or induce RORγ and/or RORα co-activator/co-repressor interactions, thus determining RORα, RORγ, or RORα/RORγ compound selectivity. The assay was performed as per manufacturer's instructions and TR-FRET was assessed 2 and 20 hours post-assay initiation. Compounds were identified to (i) have no impact on either co-activator displacement or co-activator recruitment from the assessed LBD (ii) promote co-activator displacement from the assessed LBD (iii) promote co-repressor recruitment to the assessed LBD or (iv) concurrently promote co-activator displacement from the assessed LBD and co-repressor recruitment to the assessed LBD. The $EC_{50}$ potency of compounds tested for co-activator displacement and co-repressor recruitment to RORγ and RORα are presented in the table below.

| | RORγ $EC_{50}$ [μM] | | | | RORα $EC_{50}$ [μM] | | | |
|---|---|---|---|---|---|---|---|---|
| Compound from Example | $D22^Δ$ 2 hr | $D22^Δ$ 20 hr | NCoR1-$D2^\&$ 2 hr | NCoR1-$D2^\&$ 20 hr | $D22^Δ$ 2 hr | $D22^Δ$ 20 hr | NCoR1-$D2^\&$ 2 hr | NCoR1-$D2^\&$ 20 hr |
| 1 | <30 | <30 | >30 | <30 | >30 | <30 | <30 | <30 |
| 2 | <30 | <30 | <30 | <30 | <30 | <30 | <30 | <30 |
| 3 | <30 | >30 | >30 | <30 | >30 | >30 | >30 | <30 |
| 4 | >30 | >30 | >30 | <30 | >30 | >30 | >30 | <30 |
| 5 | >30 | <30 | >30 | <30 | >30 | <30 | >30 | >30 |
| 6 | <30 | <30 | >30 | <30 | >30 | <30 | >30 | >30 |
| 7 | <30 | <30 | >30 | <30 | <30 | <30 | >30 | <30 |

-continued

| Compound from Example | RORγ EC$_{50}$ [μM] | | | | RORα EC$_{50}$ [μM] | | | |
|---|---|---|---|---|---|---|---|---|
| | D22$^\Delta$ 2 hr | D22$^\Delta$ 20 hr | NCoR1-D2$^\&$ 2 hr | NCoR1-D2$^\&$ 20 hr | D22$^\Delta$ 2 hr | D22$^\Delta$ 20 hr | NCoR1-D2$^\&$ 2 hr | NCoR1-D2$^\&$ 20 hr |
| 8 | <30 | <30 | <30 | >30 | >30 | <30 | <30 | >30 |
| 9 | >30 | >30 | <30 | >30 | >30 | <30 | >30 | <30 |

$^\Delta$- Values represent EC$_{50}$ [μM] of D22 co-activator displacement from the respective ROR LBD
$^\&$- Values represent EC$_{50}$ [μM] of NCoR1-D2 co-repressor recruitment to the respective ROR LBD The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. All patents, patent applications, and publications cited herein are hereby incorporated by reference in their entireties.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula I:

wherein
A is aryl or heteroaryl optionally substituted with C1-C4 alkyl, halogen, OH, CN, or N(R$_4$)$_2$;
R$_1$ is absent, H, OH, halogen, N(R$_4$)$_2$, or C1-C4 alkyl optionally substituted with halogen, OH, O-alkyl, CN, or N(R$_4$)$_2$;
R$_2$ and R$_3$ are independently H, halogen, or C1-C4 alkyl optionally substituted with halogen, OH, CN, N(R$_4$)$_2$, or R$_2$ and R$_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or N(R$_4$)$_2$, or R$_2$ and R$_3$, can be taken together to form a carbonyl;
Each R$_4$ is independently H, alkyl, or aryl, or two R$_4$ can be taken together to form a 4-7 membered ring, optionally incorporating 0-3 N, O, S atoms; wherein the 4-7 membered ring is optionally substituted with C1-C4 alkyl, halogen, OH, CN, halogen, or N(R$_4$)$_2$;
Each R$_5$ is independently H or alkyl, or both R5 can be taken together to form a carbonyl;
Y is 5-7 membered heteroaromatic ring linked via a carbon atom and optionally substituted, selected from unsubstituted thienyl, substituted or unsubstituted oxazolyl, substituted or unsubstituted thiazolyl, substituted or unsubstituted isoxazolyl, substituted or unsubstituted isothiazolyl, substituted or unsubstituted imidazolyl, substituted or unsubstituted pyrazolyl, substituted or unsubstituted oxadiazolyl, substituted or unsubstituted thiadiazolyl, substituted or unsubstituted triazolyl, substituted or unsubstituted pyridinyl, substituted or unsubstituted pyrimidinyl, substituted or unsubstituted pyrazinyl, substituted or unsubstituted pyridazinyl, and substituted or unsubstituted triazinyl;
n is 0, or 1;
o is 0 or 1;
p is 1 or 2; and
wherein the symbol ═══ indicates a single or double bond;
or a pharmaceutically acceptable salt, hydrate, solvate, prodrug, and tautomer thereof.

2. The compound of claim 1, wherein Y is substituted or unsubstituted pyrazolyl.
3. The compound of claim 1, wherein Y is substituted or unsubstituted triazolyl.
4. The compound of claim 1, wherein Y is substituted or unsubstituted oxadiazolyl.
5. The compound of claim 1, wherein Y is substituted or unsubstituted pyrimidinyl.
6. The compound of claim 1, wherein Y is substituted or unsubstituted pyridinyl.
7. The compound or claim 1, wherein Y is substituted or unsubstituted pyrazinyl.
8. The compound of claim 1 wherein the compound is selected from the group consisting of:

81
-continued
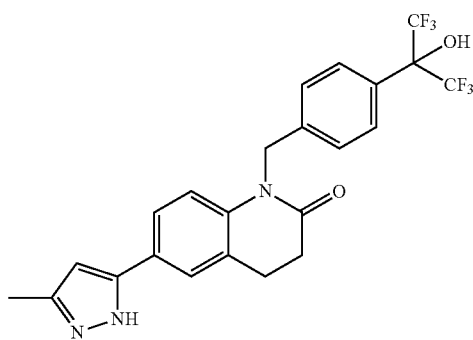
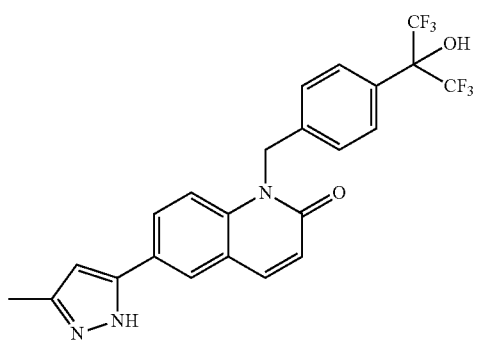
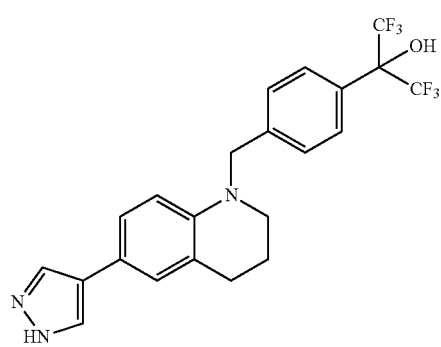
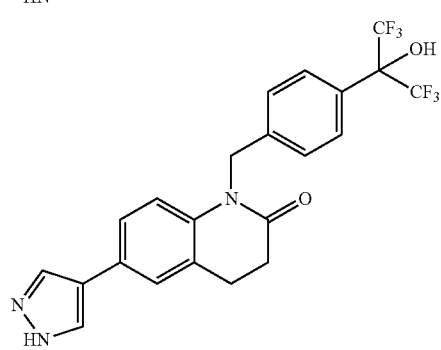
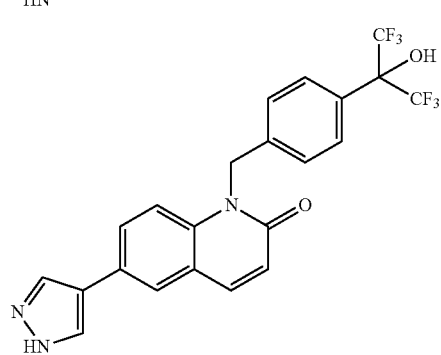
82
-continued
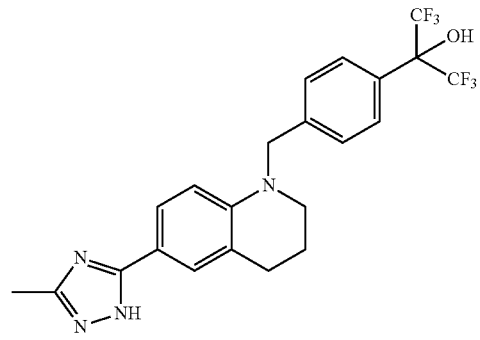
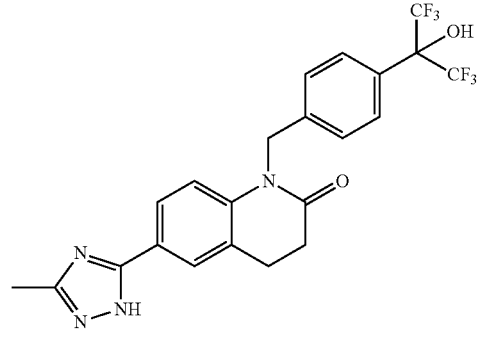
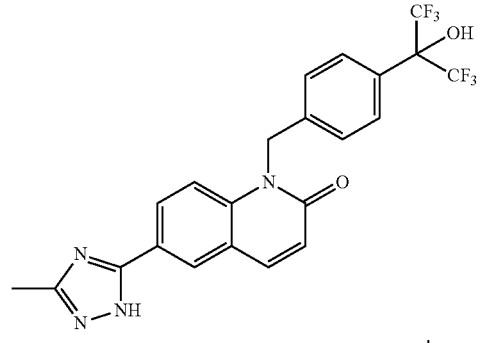
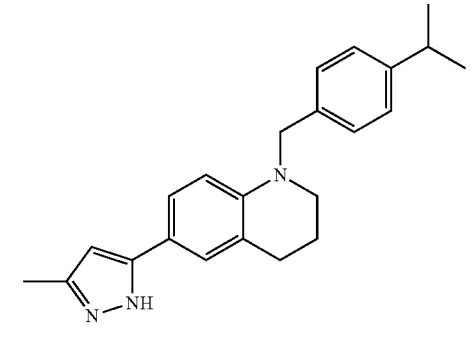
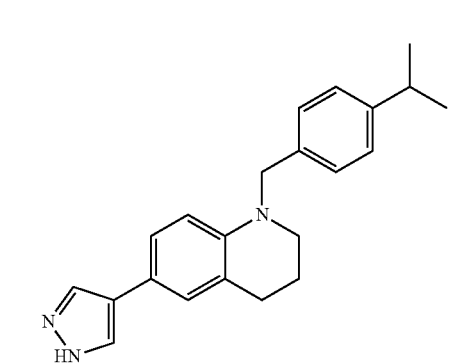

83
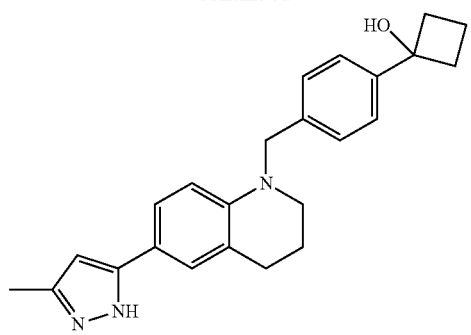
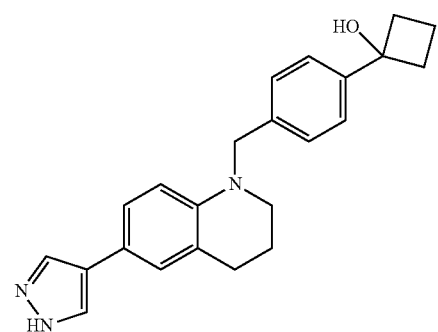
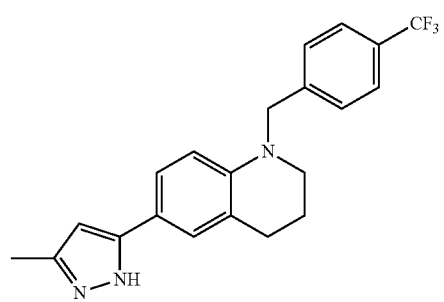
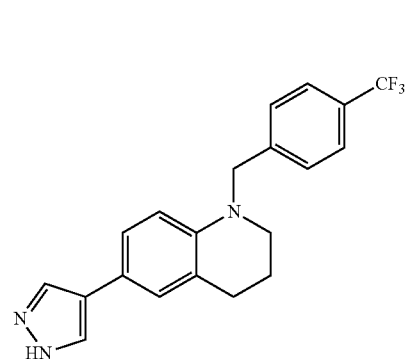
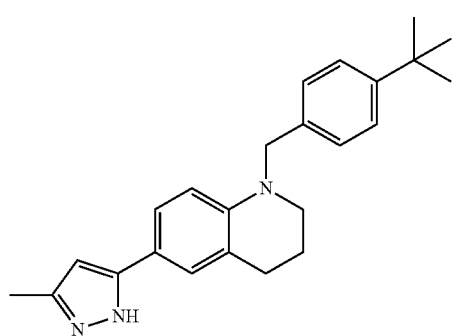
84
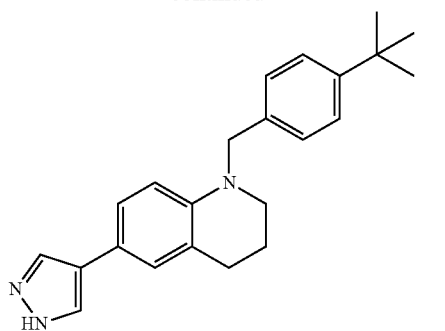
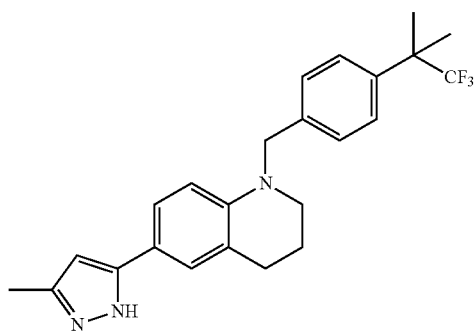
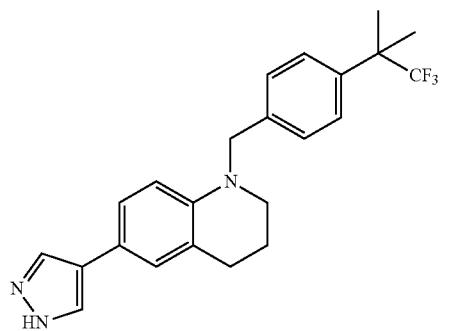
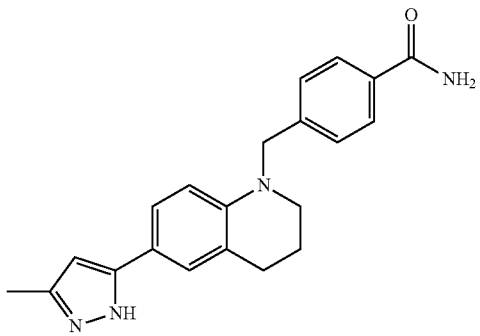
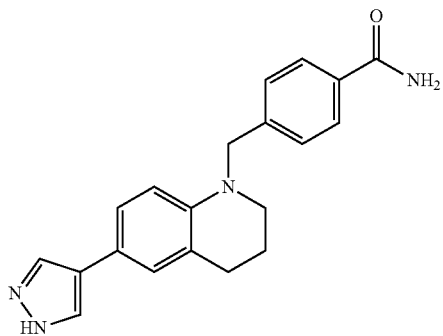

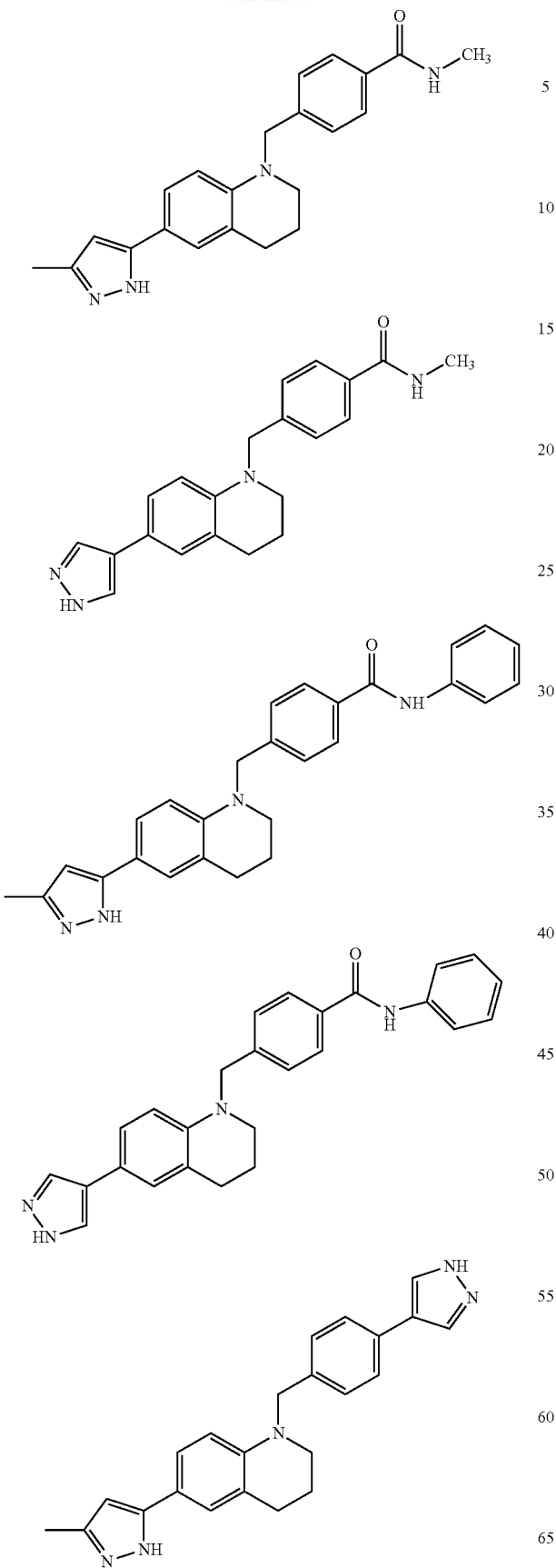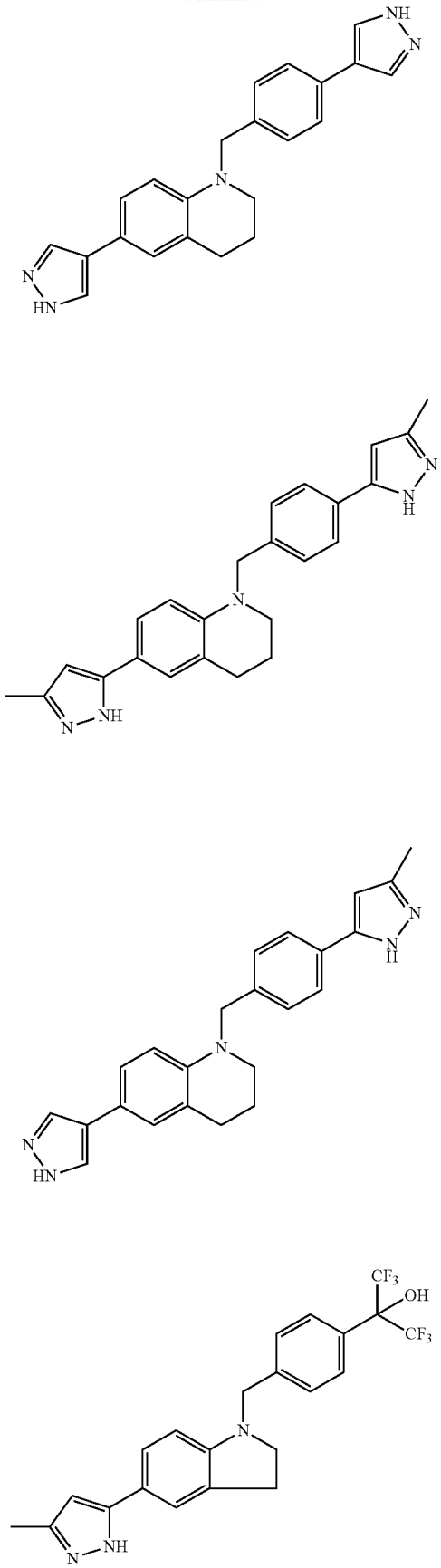

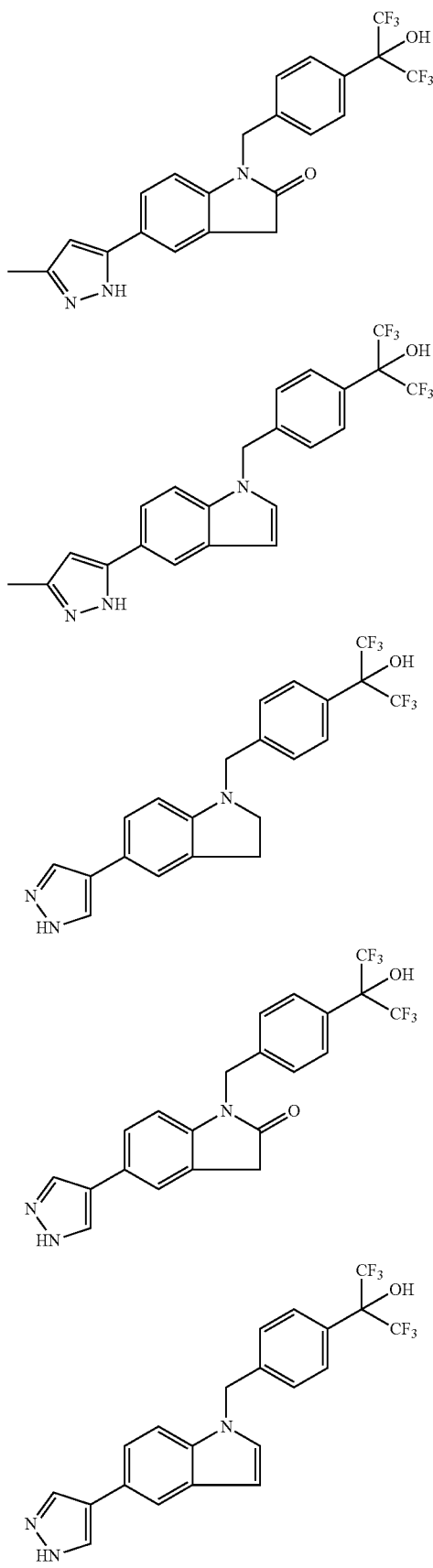
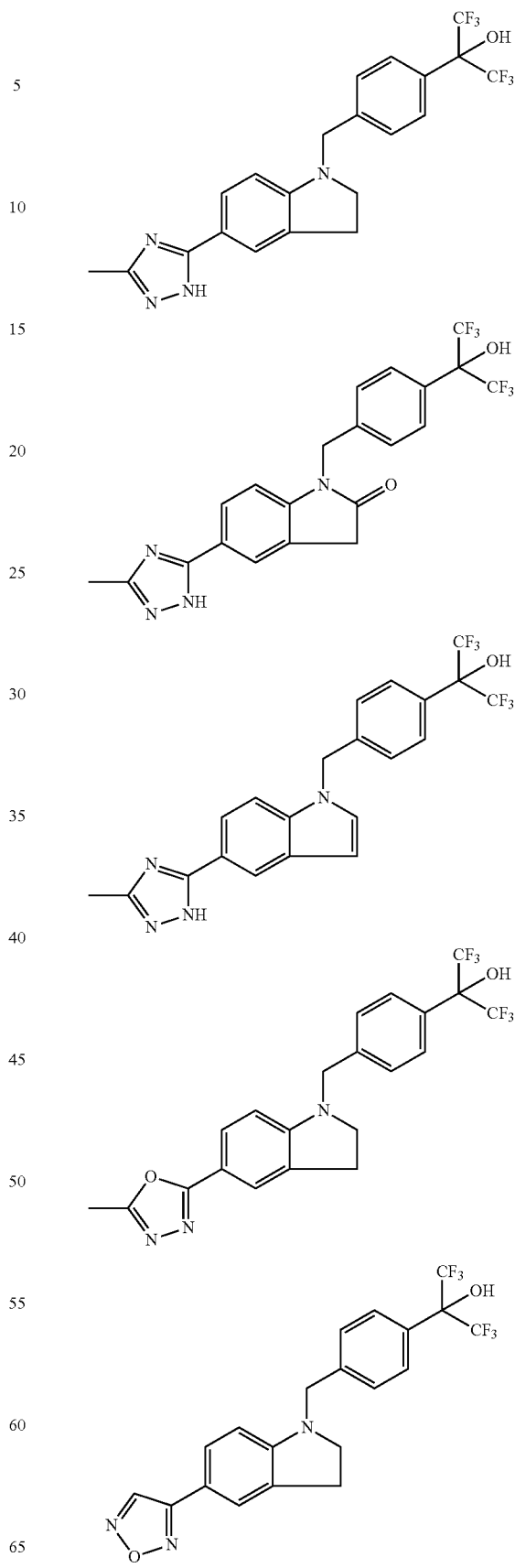

89
-continued
90
-continued
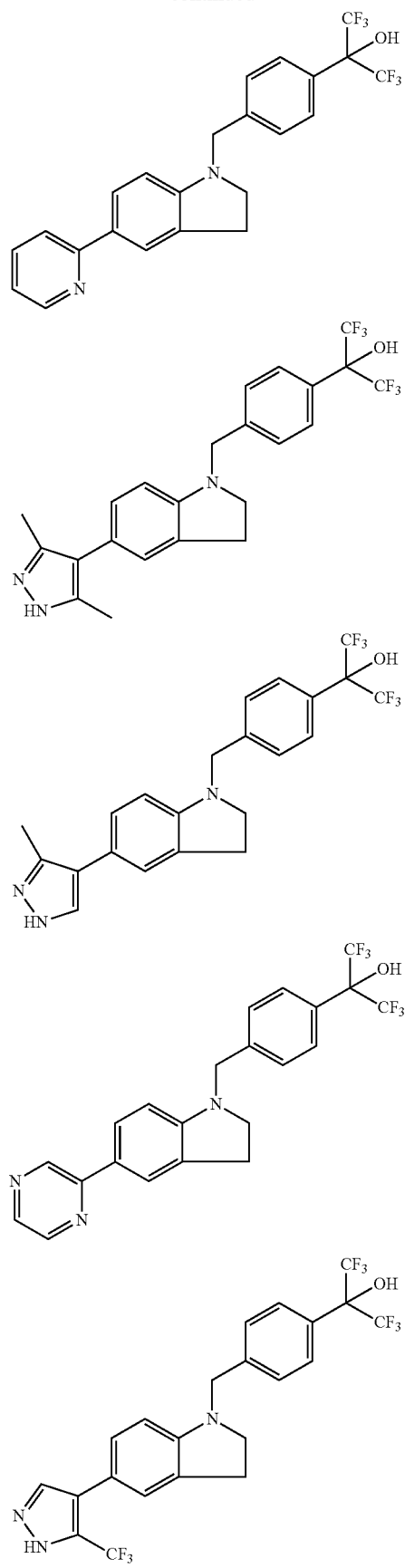 [SMILES: OC(c1ccc(CN2CCc3cc(-c4ccccn4)ccc32)cc1)(C(F)(F)F)C(F)(F)F ; Cc1n[nH]c(C)c1-c1ccc2c(c1)CCN2Cc1ccc(C(O)(C(F)(F)F)C(F)(F)F)cc1 ; Cc1n[nH]cc1-c1ccc2c(c1)CCN2Cc1ccc(C(O)(C(F)(F)F)C(F)(F)F)cc1 ; OC(c1ccc(CN2CCc3cc(-c4cnccn4)ccc32)cc1)(C(F)(F)F)C(F)(F)F ; OC(c1ccc(CN2CCc3cc(-c4cn[nH]c4C(F)(F)F)ccc32)cc1)(C(F)(F)F)C(F)(F)F]
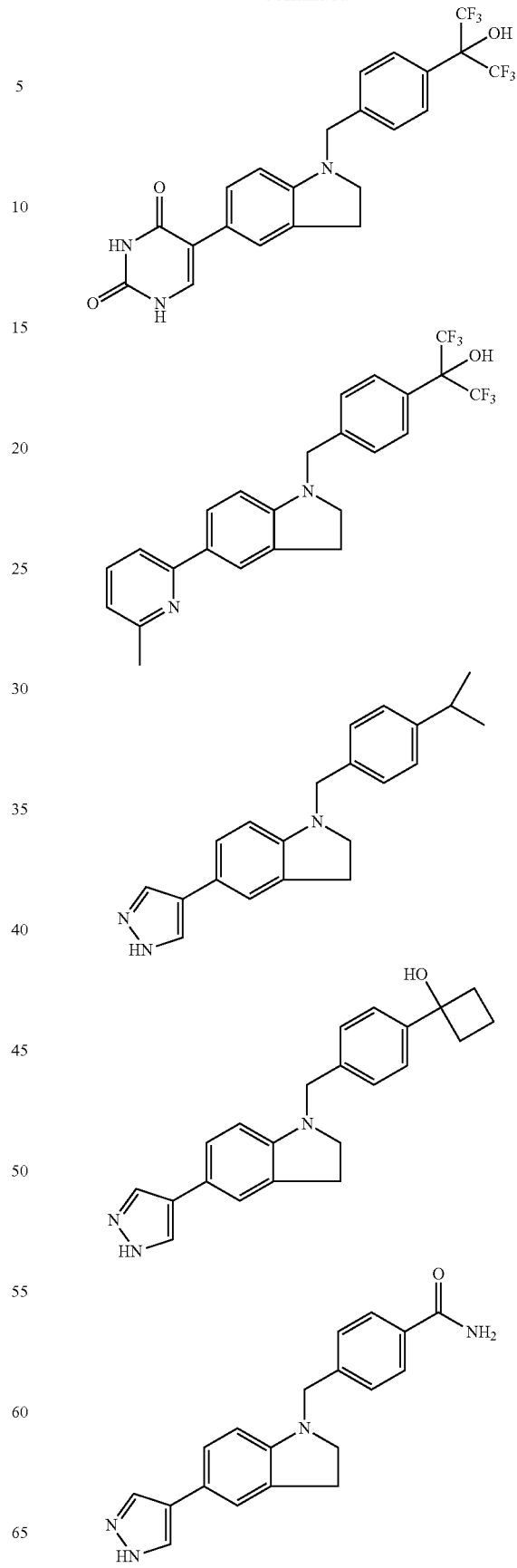

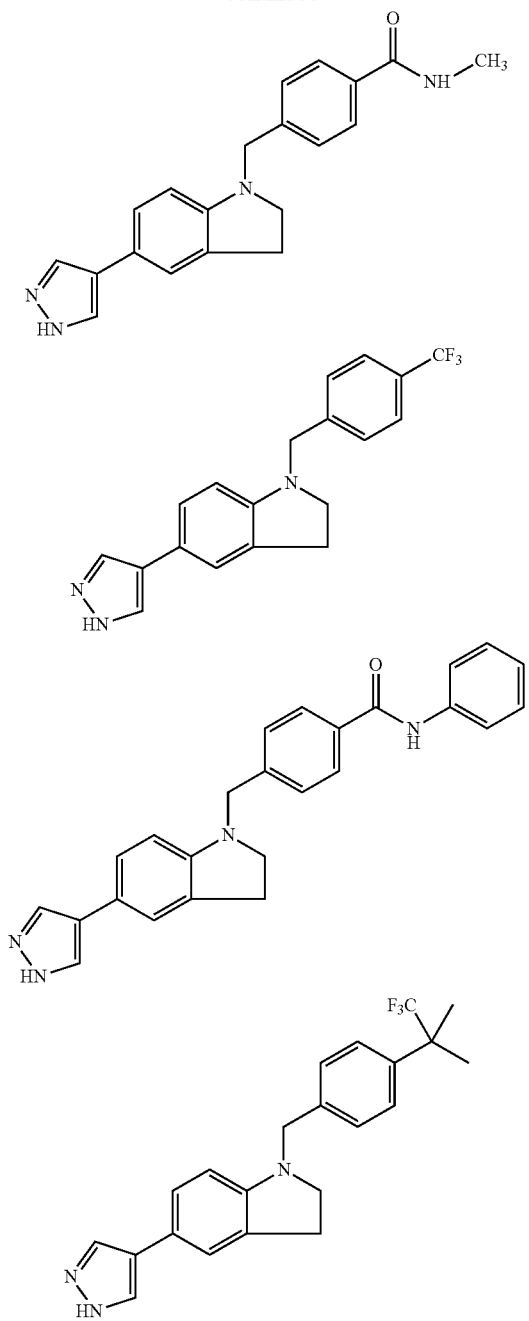
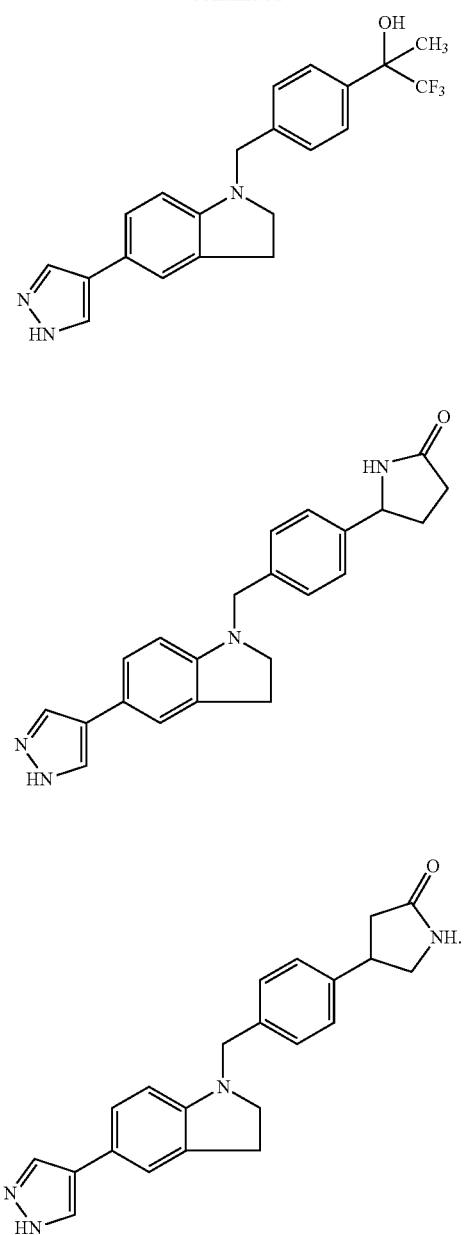
9. The compound of claim 1, wherein the compound is selected from the group consisting of:
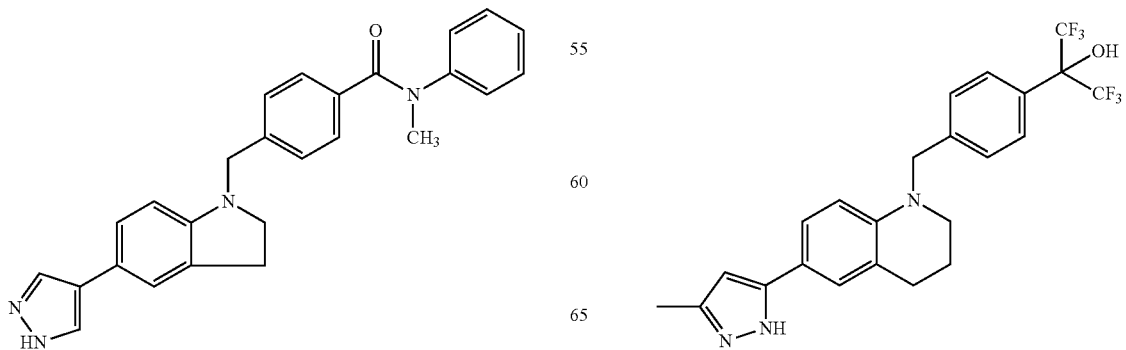

93
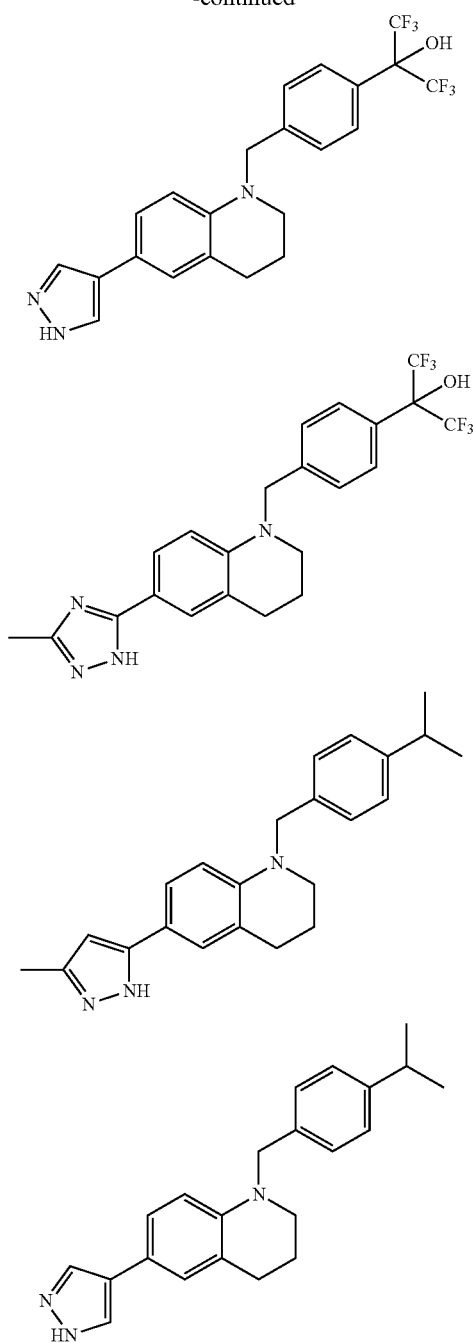
94
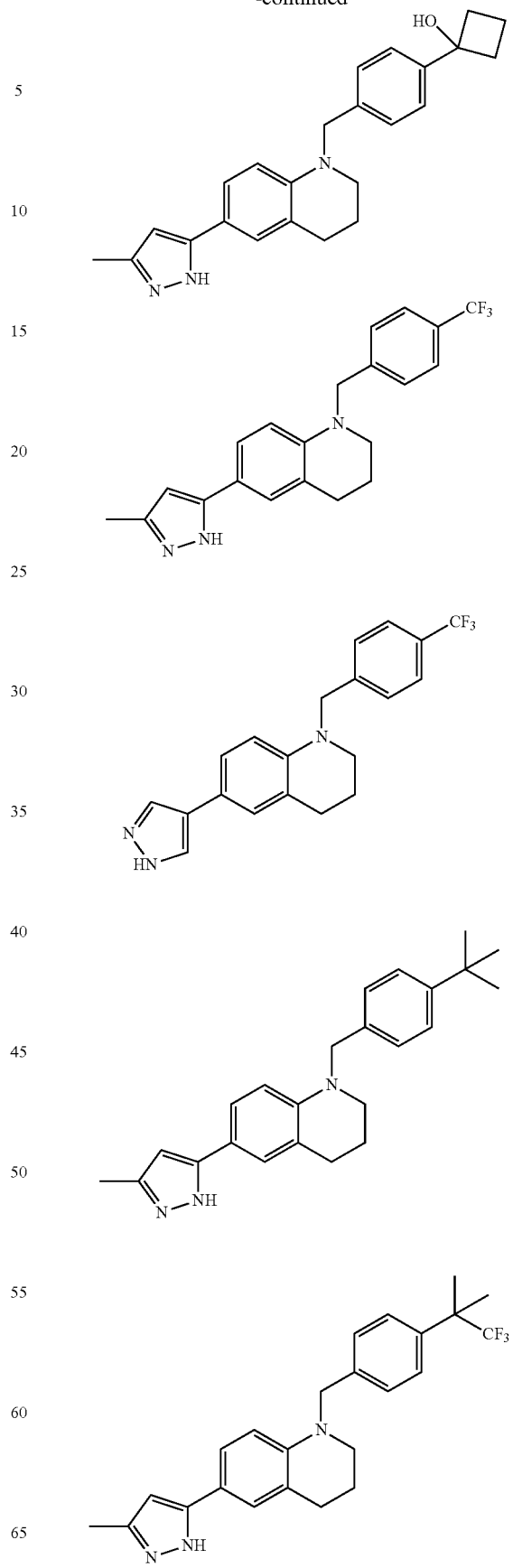

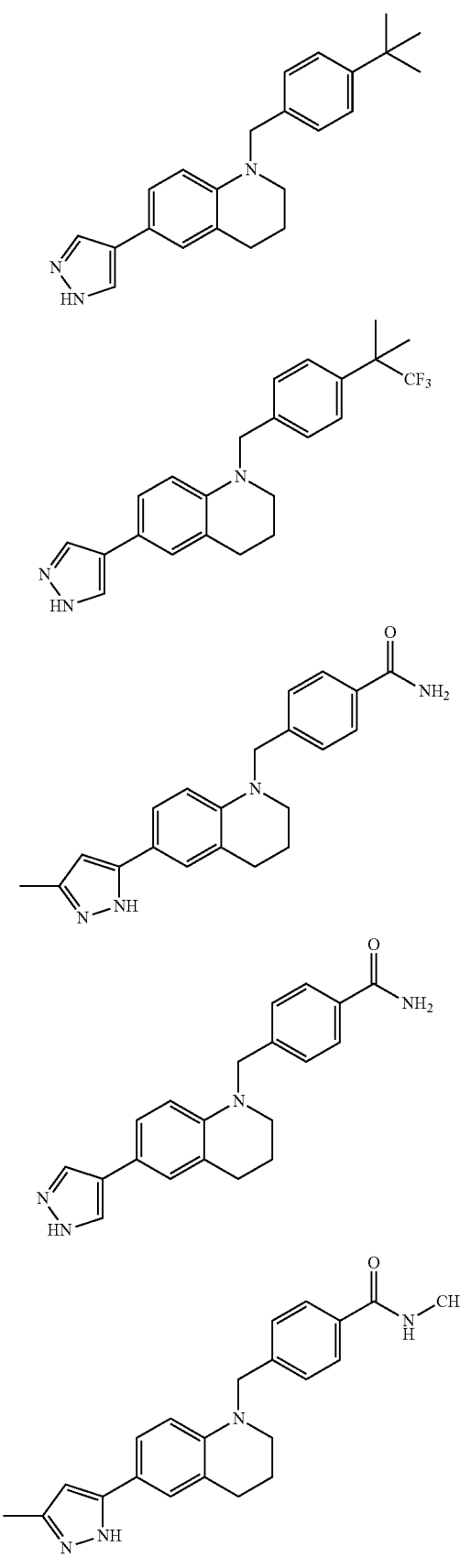
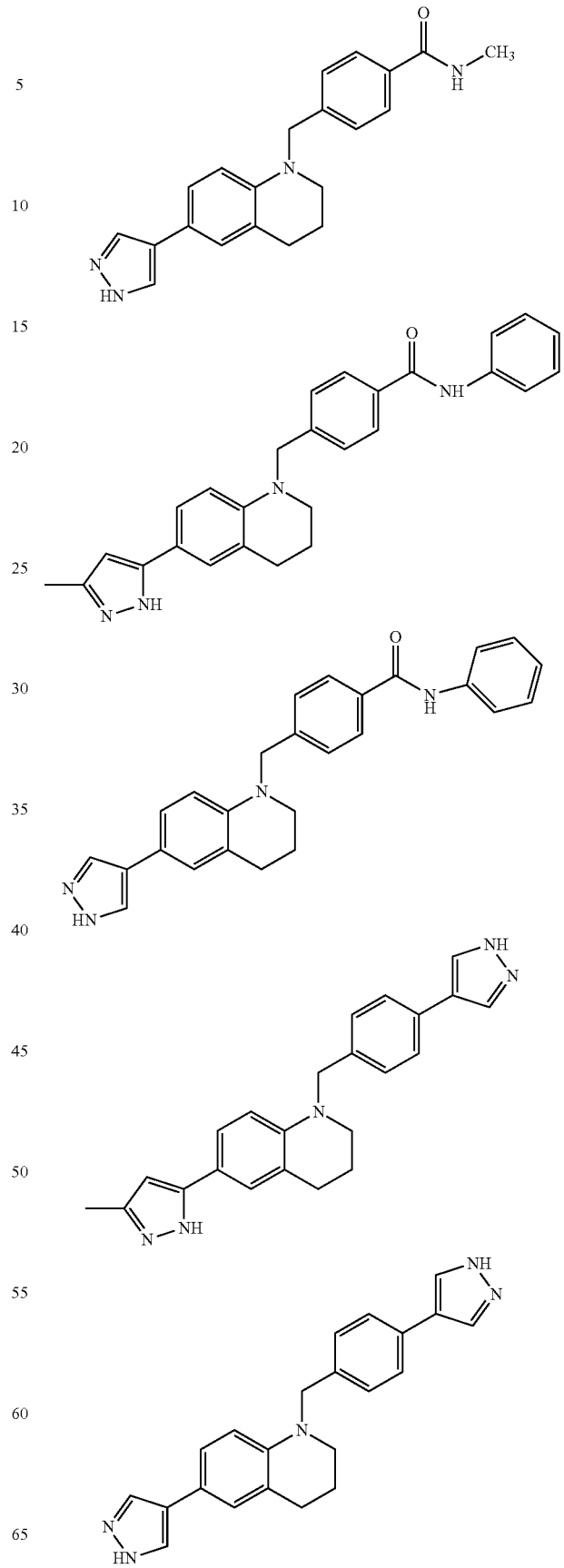

-continued

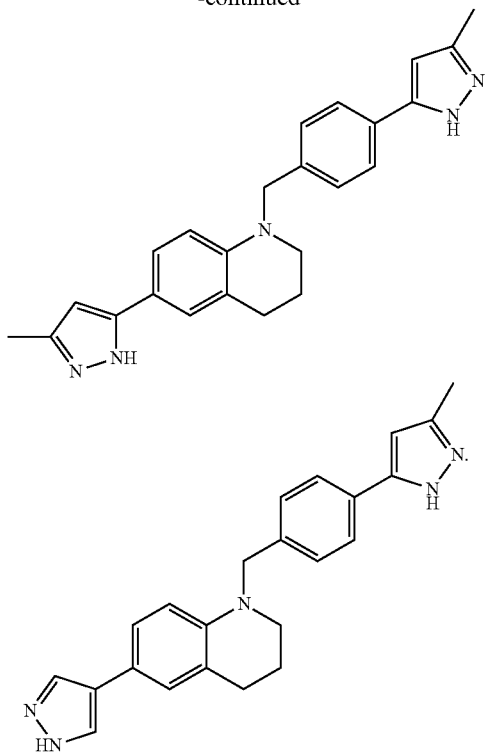

10. A compound of formula Ib:

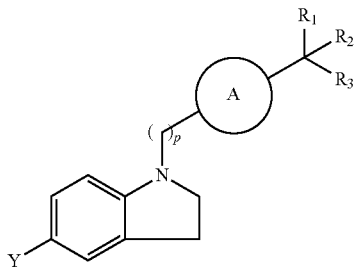

wherein
A is aryl or heteroaryl is optionally substituted with C1-C4 alkyl, halogen, OH, CN, or N(R$_4$)$_2$;
R$_1$ is absent, H, OH, halogen, N(R)$_2$, or C1-C4 alkyl optionally substituted with halogen, OH, O-alkyl, CN, or N(R$_4$)$_2$;
R$_2$ and R$_3$ are independently selected from H, halogen, or C1-C4 alkyl optionally substituted with halogen, OH, CN, N(R$_4$)$_2$, or R$_2$ and R$_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or N(R-i)$_2$, or R$_2$ and R$_3$, can be taken together to form a carbonyl;
Each R$_4$ is independently H, alkyl, or aryl, or two R$_4$ can be taken together to form a 4-7 membered ring, optionally incorporating an 0-3 atoms; wherein the 4-7 membered ring is optionally substituted with C1-C4 alkyl, halogen, OH, CN, halogen, or N(R$_4$)$_2$;
Y is 5-7 membered heteroaryl linked via a carbon atom and optionally substituted; and p is 1 or 2;
or a pharmaceutically acceptable salt, hydrate, solvate, prodrug, and tautomer thereof.

11. The compound of claim 10, wherein the compound is selected from the group consisting of:

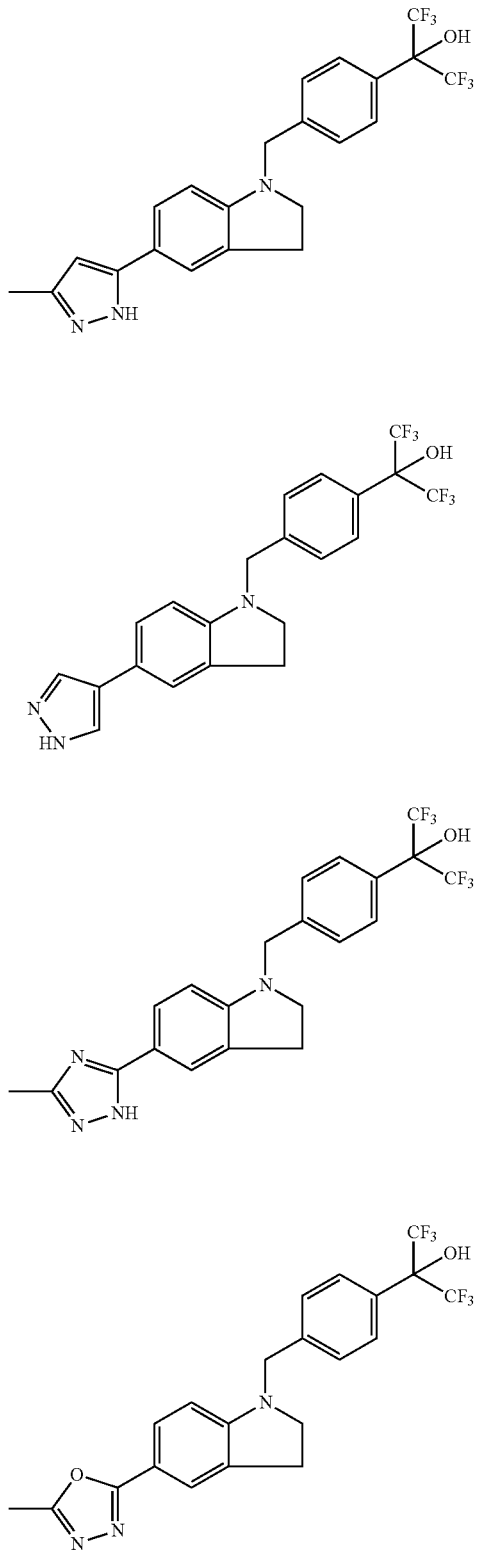

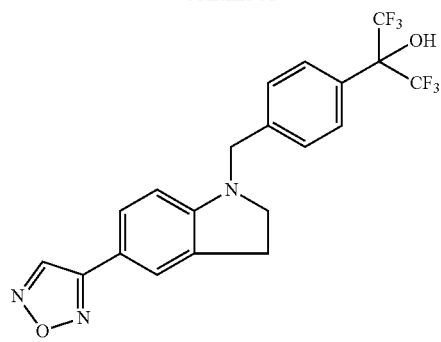
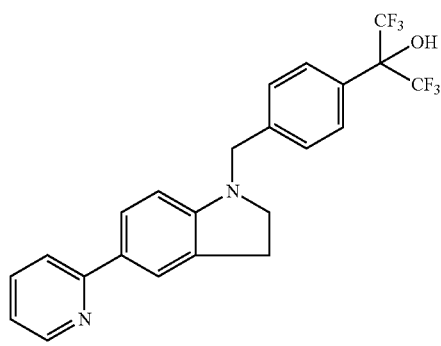
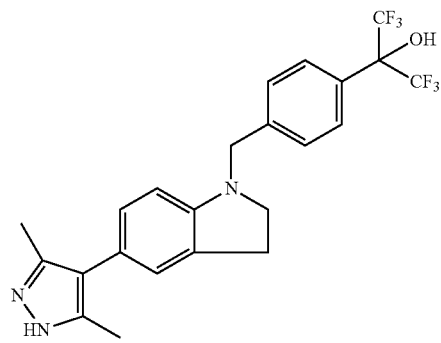
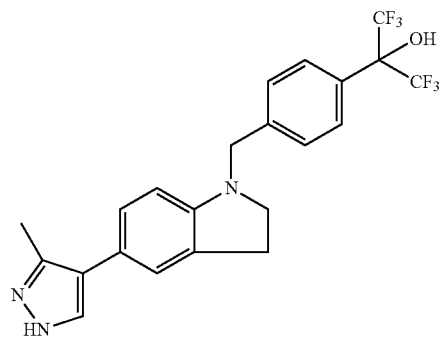
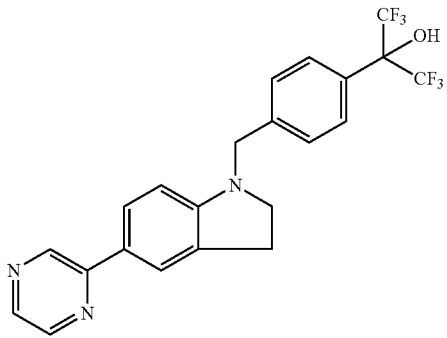
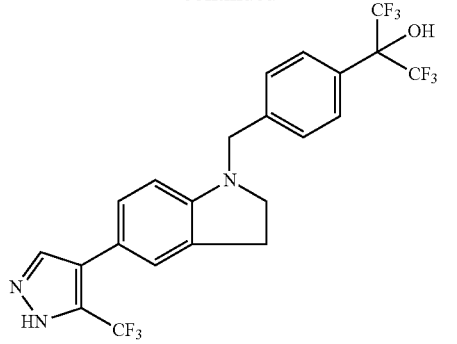
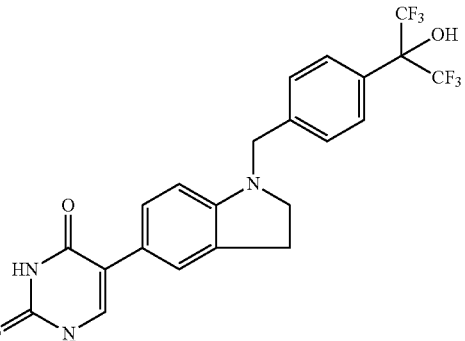
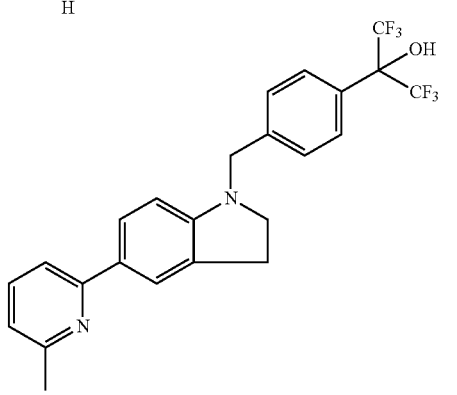
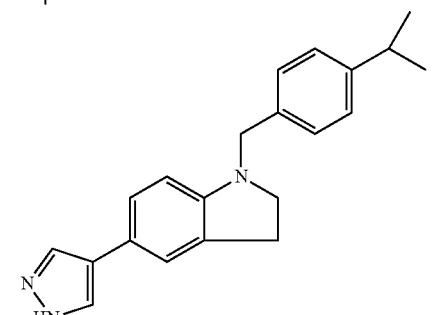
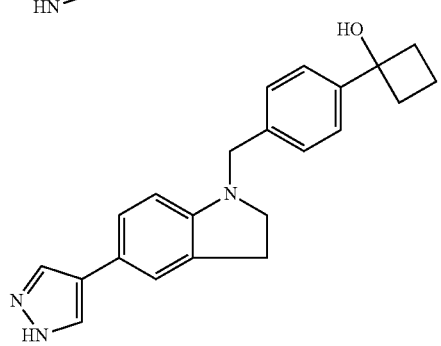

-continued

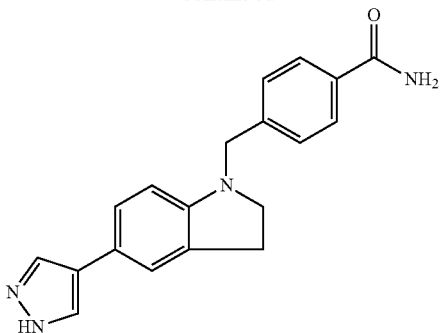

12. A compound of formula Ic:

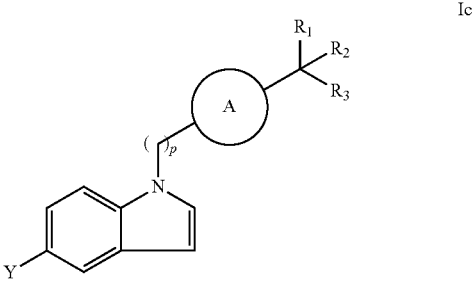

wherein
A is aryl or heteroaryl; optionally substituted with C1-C4 alkyl, halogen, OH, CN, and N(R4)$_2$;
R$_1$ is absent, H, OH, halogen, N(R$_4$)$_2$, or C1-C4 alkyl optionally substituted with halogen, OH, O-alkyl, CN, or N(R$_4$)$_2$;
R$_2$ and R$_3$ are independently selected from H, halogen, or C1-C4 alkyl optionally substituted with halogen, OH, CN, N(R$_4$)$_2$, or R$_2$ and R$_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or N(R$_4$)$_2$, or R$_2$ and R$_3$, can be taken together to form a carbonyl;
Each R$_4$ is independently H, alkyl, or aryl, or two R$_4$ can be taken together to form a 4-7 membered ring, optionally incorporating 0-3 N, O, S atoms; wherein the 4-7 membered ring is optionally substituted with C1-C4 alkyl, halogen, OH, CN, halogen, or N(R$_4$)$_2$;
Y is 5-7 membered heteroaryl linked via a carbon atom and optionally substituted, selected from substituted or unsubstituted thienyl, substituted or unsubstituted oxazolyl, substituted or unsubsthuted thiazolyl, substituted or unsubstituted isoxazolyl, substituted or unsubstituted isothiazolyl, substituted or unsubstituted imidazolyl, substituted or unsubstituted pyrazolyl, substituted or unsubstituted oxadiazolyl, substituted or unsubstituted thiadiazolyl, substituted or unsubstited triazolyl, substituted or unsubstituted pyridinyl, substituted or unsubstituted pyrimidinyl, substituted or unsubstituted pyrazinyl, substituted or unsubstituted pyridazinyl, and substituted or unsubstituted triazinyl; and
p is 1 or 2;
or a pharmaceutically acceptable salt, hydrate, solvate, prodrug, and tautomer thereof.

13. The compound of claim 12, wherein the compound is selected from the group

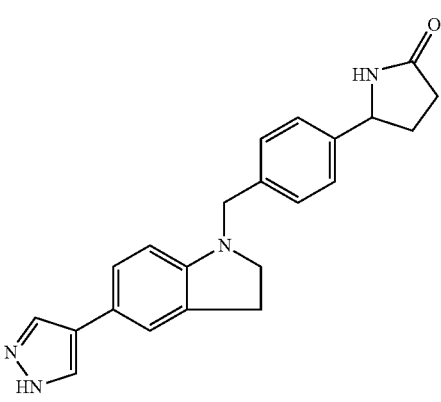

-continued

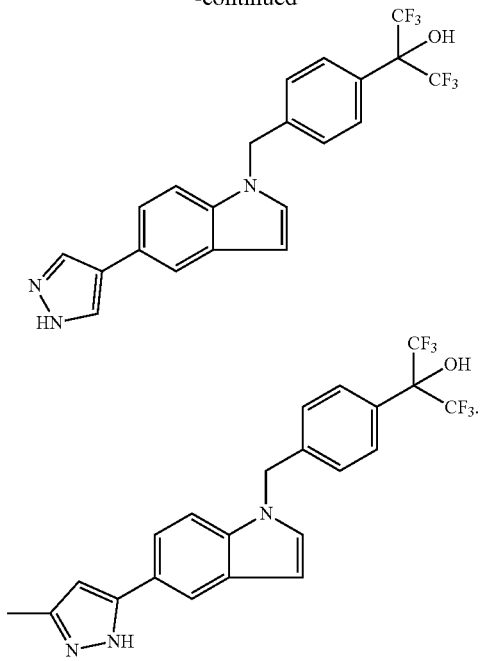

14. A compound of formula Id:

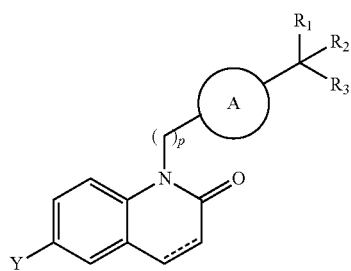

wherein
A is aryl or heteroaryl optionally substituted with C1-C4 alkyl, halogen, OH, CN, and N(R4)2;
$R_1$ is absent, H, OH, halogen, $N(R)_2$, or C1-C4 alkyl optionally substituted with halogen, OH, O-alkyl, CN, or $N(R_4)_2$;
$R_2$ and $R_3$ are independently selected from H or C1-C4 alkyl optionally substituted with halogen, OH, CN, $N(R_4)_2$, or $R_2$ and $R_3$, taken together may form a 4-7 membered saturated or unsaturated ring, optionally incorporating 0-3 N, O, or S atoms; wherein the 4-7 membered ring is optionally substituted with C1-C4 alkyl, halogen, OH, carbonyl, CN, halogen, or $N(R_4)_2$, or $R_2$ and $R_3$, can be taken together to form a carbonyl;
Each $R_4$ is independently H, alkyl, or aryl, or two can be taken together to form a 4-7 membered ring, optionally incorporating an additional N, O, S atom; wherein the 4-7 membered ring is optionally substituted with C1-C4 alkyl, halogen, OH, CN, halogen, or $N(R_4)_2$;
Y is 5-7 membered heteroaryl linked via a carbon atom and optionally substituted;
p is 1 or 2; and
wherein the symbol ≡ indicates a single or double bond;

or a pharmaceutically acceptable salt, hydrate, solvate, prodrug, and tautomer thereof.

15. The compound of claim 12, wherein the compound is selected from the group consisting of:

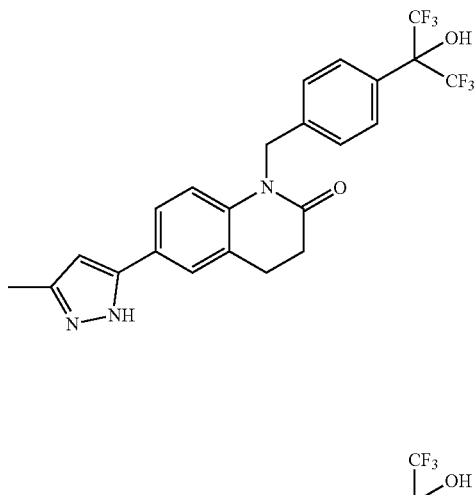

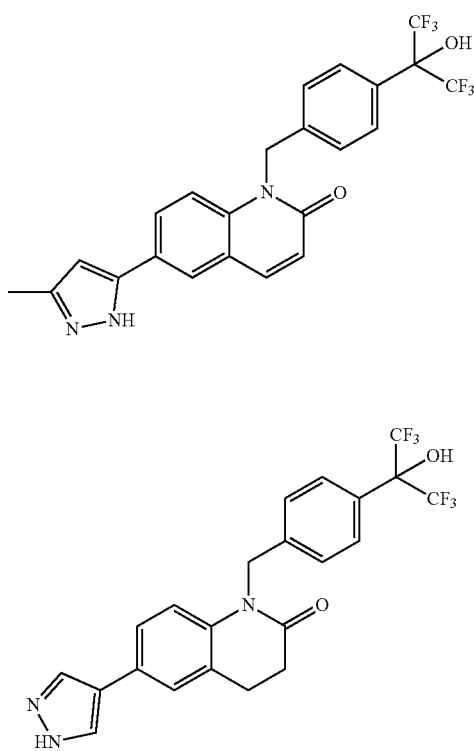

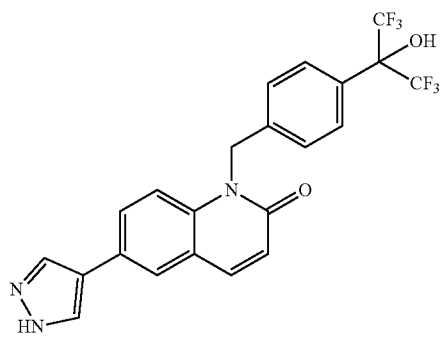

-continued
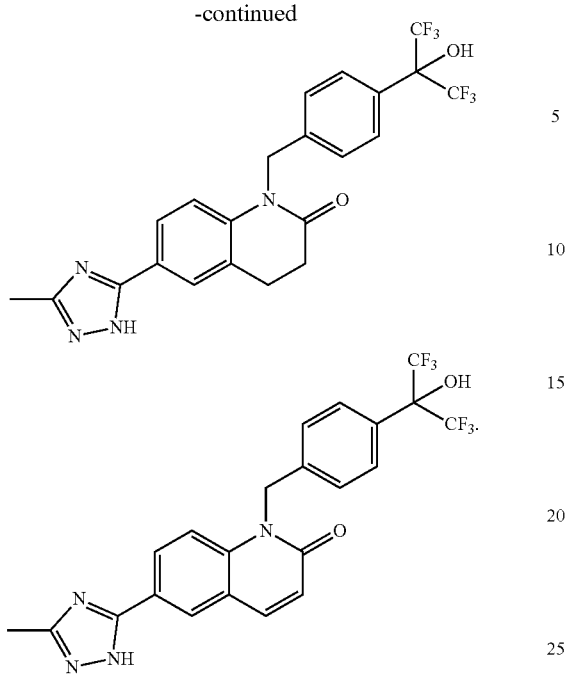
16. A pharmaceutical composition comprising a compound of claim 1 and a pharmaceutically acceptable carrier.
* * * * *